US006514985B1

(12) United States Patent
Gerster et al.

(10) Patent No.: US 6,514,985 B1
(45) Date of Patent: Feb. 4, 2003

(54) IMIDAZONAPHTHYRIDINES

(75) Inventors: John F. Gerster, Woodbury, MN (US); Kyle J. Lindstrom, Houlton, WI (US); Stephen L. Crooks, Mahtomedi, MN (US); Philip D. Heppner, Woodbury, MN (US); Gregory J. Marszalek; Peter V. Maye, both of St. Paul, MN (US); Bryon A. Merrill, River Falls, WI (US); John W. Mickelson, North St. Paul; Michael J. Rice, Oakdale, both of MN (US)

(73) Assignee: 3M Innovative Properties Company, St. Paul, MN (US)

( * ) Notice: Subject to any disclaimer, the term of this patent is extended or adjusted under 35 U.S.C. 154(b) by 31 days.

(21) Appl. No.: 09/706,990

(22) Filed: Nov. 6, 2000

Related U.S. Application Data

(62) Division of application No. 09/210,114, filed on Dec. 11, 1998, now Pat. No. 6,194,425.
(60) Provisional application No. 60/069,276, filed on Dec. 11, 1997.

(51) Int. Cl.[7] .................. A61K 31/4353; C07D 471/12
(52) U.S. Cl. ........................................ 514/293; 546/82
(58) Field of Search ............................ 514/293; 546/82

(56) References Cited

U.S. PATENT DOCUMENTS

| | | | |
|---|---|---|---|
| 3,314,941 A | 4/1967 | Littell et al. | |
| 4,689,338 A | * 8/1987 | Gerster | ........................ 514/293 |
| 4,698,348 A | 10/1987 | Gerster | |
| 4,929,624 A | 5/1990 | Gerster et al. | |
| 5,037,986 A | 8/1991 | Gerster | |
| 5,238,944 A | 8/1993 | Wick et al. | |
| 5,266,575 A | 11/1993 | Gerster | |
| 5,268,376 A | 12/1993 | Gerster | |
| 5,346,905 A | 9/1994 | Gerster | |
| 5,352,784 A | 10/1994 | Nikolaides et al. | |
| 5,389,640 A | 2/1995 | Gerster et al. | |
| 5,444,065 A | 8/1995 | Nikolaides et al. | |
| 5,446,153 A | 8/1995 | Lindstrom et al. | |
| 5,482,936 A | 1/1996 | Lindstrom | |
| 5,494,916 A | 2/1996 | Lindstrom et al. | |
| 5,525,612 A | 6/1996 | Gerster | |
| 5,605,899 A | 2/1997 | Gerster et al. | |
| 5,627,281 A | 5/1997 | Nikolaides et al. | |
| 5,644,063 A | 7/1997 | Lindstrom et al. | |
| 5,648,516 A | 7/1997 | Nikolaides et al. | |
| 5,714,608 A | 2/1998 | Gerster | |
| 5,741,909 A | 4/1998 | Gerster et al. | |
| 5,756,747 A | 5/1998 | Gerster et al. | |
| 5,886,006 A | 3/1999 | Nikolaides et al. | |
| 5,939,090 A | 8/1999 | Beaurline et al. | |
| 5,977,366 A | 11/1999 | Gerster et al. | |
| 6,039,969 A | 3/2000 | Tomai et al. | |
| 6,069,149 A | 5/2000 | Nanba et al. | |
| 6,083,505 A | 7/2000 | Miller et al. | |
| 6,110,929 A | 8/2000 | Gerster et al. | |
| 6,194,425 B1 | 2/2001 | Gerster et al. | |
| 6,323,200 B1 | 11/2001 | Gerster et al. | |
| 6,331,539 B1 | 12/2001 | Crooks et al. | |
| 6,348,462 B1 | 2/2002 | Gerster et al. | |
| 6,365,166 B2 | 4/2002 | Beaurline et al. | |

FOREIGN PATENT DOCUMENTS

| | | |
|---|---|---|
| JP | 9-208584 | 8/1997 |
| JP | 9-255926 | 3/1999 |
| WO | WO 93/09119 | 5/1993 |
| WO | WO 97/48704 | 12/1997 |
| WO | WO 00/09506 | 2/2000 |
| WO | WO 00/76505 | 12/2000 |
| WO | WO 00/76518 | 12/2000 |

OTHER PUBLICATIONS

Hart, E.P. "Napthyridines. Hydroxynaphthyridines", *Journal of Chemical Society*, Part III, pp. 212–214 (1956).
Wozniak, et al, "The Amination of 3–nitro–1,5–naphthyridines by Liquid Ammonia/Potassium Permanganate[1,2]. A New and Convenient Amination Method.", *Journal of the Royal Netherlands Chemical Society*, 102, pp. 511–513, Dec. 12, 1983.
Brennan, et al, "Automated Bioassay of Interferons in Micro–test Plates", *Biotechniques*, Jun./Jul., 78, 1983.
Testerman, et al, "Cytokine Induction by the Immunomodulators Imiquimod and S–27609", *Journal of Leukocyte Biology*, vol. 58, pp. 365–372, Sep. 1995.
Bachman, et al, "Synthesis of Substituted Quinolylamines. Derivatives of 4–Amino–7–Chloroquinoline", *J. Org. Chem*, 15, pp. 1278–1284 (1950).
Jain, et al, "Chemical and Pharmacological Investigations of Some ω–Substituted Alkylamino–3–aminopyridines", *J. Med. Chem.*, 11, pp. 87–92 (1968).
Baranov, et al., *Chem. Abs.* 85, 94371, (1976).
Berényi, et al, "Ring Transformation of Condensed Dihydro–as–triazines", *J. Heterocyclic Chem.*, 18, pp. 1537–1540 (1981).

\* cited by examiner

*Primary Examiner*—Charanjit S. Aulakh
(74) *Attorney, Agent, or Firm*—Dean A. Ersfeld

(57) ABSTRACT

Imidazonaphthyridine and tetrahydroimidazonaphthyridine compounds induce the biosynthesis of cytokines such as interferon and tumor necrosis factor. The compounds exhibit antiviral and antitumor properties. Methods of preparing the compounds and intermediates useful in the preparation of the compounds are also disclosed.

16 Claims, No Drawings

IMIDAZONAPHTHYRIDINES

This application is a Division of Ser. No. 09/210,114 filed Dec. 11, 1998, now U.S. Pat. No. 6,194,425, which claims the benefit of U.S. Provisional Application No. 60/069,276 filed Dec. 11, 1997.

FIELD OF THE INVENTION

This invention relates to imidazonaphthyridine and tetrahydroimidazonaphthyridine compounds, processes for making these compounds and intermediates used in their preparation. This invention additionally relates to pharmaceutical compositions containing imidazonaphthyridine and tetrahydroimidazonaphthyridine compounds. A further aspect of this invention relates to the use of these compounds as immunomodulators and for inducing cytokine biosynthesis in animals.

BACKGROUND OF THE INVENTION

The first reliable report on the 1H-imidazo[4,5-c] quinoline ring system, Backman et al., *J. Org. Chem.* 15, 1278–1284 (1950) describes the synthesis of 1-(6-methoxy-8-quinolinyl)-2-methyl-1H-imidazo[4,5-c]quinoline for possible use as an antimalarial agent. Subsequently, syntheses of various substituted 1H-imidazo[4,5-c]quinolines were reported. For example, Jain et al., *J. Med. Chem.* 11, pp. 87–92 (1968), synthesized the compound 1-[2-(4-piperidyl)ethyl]-1H-imidazo[4,5-c]quinoline as a possible anticonvulsant and cardiovascular agent. Also, Baranov et al., *Chem. Abs.* 85, 94362 (1976), have reported several 2-oxoimidazo [4,5-c]quinolines, and Berenyi et al., *J. Heterocyclic Chem.* 18, 1537–1540 (1981), have reported certain 2-oxoimidazo [4,5-c]quinolines.

Certain 1H-imidazo[4,5-c]quinolin-4-amines and 1- and 2-substituted derivatives thereof were later found to be useful as antiviral agents, bronchodilators and immunomodulators. These are described in, inter alia, U.S. Pat. Nos. 4,689,338; 4,698,348; 4,929,624; 5,037,986; 5,268,376; 5,346,905; and 5,389,640, all of which are incorporated herein by reference. Although there continues to be interest in the imidazoquinoline ring system, as seen for example in WO 98/30562, there is a continuing need for compounds that have the ability to modulate the immune response, by induction of cytokine biosynthesis or other mechanisms.

SUMMARY OF THE INVENTION

We have found a new class of compounds that are useful in inducing cytokine biosynthesis in animals. Accordingly, this invention provides imidazonaphthyridine compounds of Formula I:

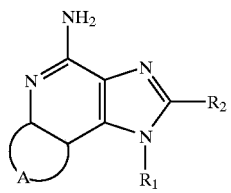

wherein A, $R_1$ and $R_2$ are as defined hereinafter.

The invention also provides tetrahydroimidazonaphthyridine compounds of Formula II:

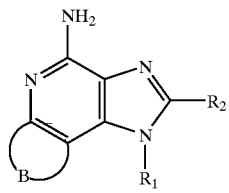

wherein B, $R_1$ and $R_2$ are as defined hereinafter.

The compounds of Formula I and Formula II are useful as immune response modifiers due to their ability to induce cytokine biosynthesis and otherwise modulate the immune response when administered to animals. This ability makes the compounds useful in the treatment of a variety of conditions, e.g. viral diseases and tumors that are responsive to such changes in the immune response.

The invention further provides pharmaceutial compositions containing a compound of Formula I or Formula II and methods of inducing cytokine biosynthesis in an animal and/or treating a viral infection in an animal by administering a compound of Formula I or Formula II to the animal.

In addition. methods of synthesizing compounds of Formula I and Formula II, and intermediates useful in the synthesis of these compounds are provided.

Further the invention provides a method of inducing interferon biosynthesis in an animal comprising the step of administering to said animal a compound of Formula I or Formula II in an amount effective to induce said interferon biosynthesis, and a method of treating a viral infection in an animal comprising the step of administering to said animal a compound of Formula I or Formula II in an amount effective to inhibit the viral infection.

DETAILED DESCRIPTION OF THE INVENTION

As mentioned earlier, the invention provides compounds of Formula I:

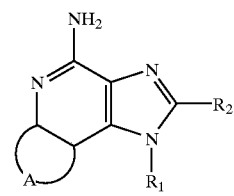

wherein
  A is =N—CR=CR—CR=; =CR—N=CR—CR=; =CR—CR=N—CR=; or =CR—CR=CR—N=;
  $R_1$ is selected from the group consisting of:
    -hydrogen;
    —$C_{1-20}$ alkyl or $C_{2-20}$ alkenyl that is unsubstituted or substituted by one or more substituents selected from the group consisting of:
      -aryl;
      -heteroaryl;
      -heterocyclyl;
      —O—$C_{1-20}$ alkyl,
      —O—($C_{1-20}$ alkyl)$_{0-1}$-aryl;
      —O—($C_{1-20}$ alkyl)$_{0-1}$heteroaryl;
      —O—($C_{1-20}$ alkyl)$_{0-1}$-heterocyclyl;
      —$C_{1-20}$ alkoxycarbonyl;
      —S(O)$_{0-2}$—$C_{1-20}$ alkyl;

—S(O)$_{0-2}$—(C$_{1-20}$ alkyl)$_{0-1}$aryl;
—S(O)$_{0-2}$—(C$_{1-20}$ alkyl)$_{0-1}$-heteroaryl;
—S(O)$_{0-2}$—C$_{1-20}$ alkyl)$_{0-1}$heterocyclyl;
—N(R$_3$)$_2$;
—N$_3$;
oxo;
-halogen;
—NO$_2$;
—OH; and
—SH; and
—C$_{1-20}$ alkyl—NR$_3$—Q—X—R$_4$ or —C$_{2-20}$ alkenyl—NR$_3$—Q—X—R$_4$ wherein Q is —CO— or —SO$_2$—; X is a bond, —O— or —NR$_3$— and R$_4$ is aryl; heteroaryl; heterocyclyl; or —C$_{1-20}$ alkyl or C$_{2-20}$ alkenyl that is unsubstituted or substituted by one or more substituents selected from the group consisting of:
-aryl;
-heteroaryl;
-heterocyclyl;
—O—C$_{1-20}$ alkyl,
—O—(C$_{1-20}$ alkyl)$_{0-1}$-aryl;
—O—(C$_{1-20}$ alkyl)$_{0-1}$-heteroaryl;
—O—(C$_{1-20}$ alkyl)$_{0-1}$-heterocyclyl;
—C$_{1-20}$ alkoxycarbonyl;
—S(O)$_{0-2}$—C$_{1-20}$ alkyl;
—S(O)$_{0-2}$—(C$_{1-20}$ alkyl)$_{0-1}$-aryl;
—S(O)$_{0-2}$—C$_{1-20}$ alkyl)$_{0-1}$-heteroaryl;
—S(O)$_{0-2}$—C$_{1-20}$ alkyl)$_{0-1}$-heterocyclyl;
—N(R$_3$)$_2$;
—NR$_3$—CO—O—C$_{1-20}$ alkyl;
—N$_3$;
oxo;
-halogen;
—NO$_2$;
—OH; and
—SH; or R$_4$ is

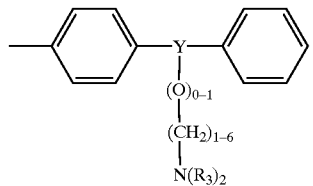

wherein Y is —N— or —CR—;
R$_2$ is selected from the group consisting of:
-hydrogen;
—C$_{1-10}$ alkyl;
—C$_{2-10}$ alkenyl;
-aryl;
—C$_{1-10}$ alkyl—O—C$_{1-10}$-alkyl;
—C$_{1-10}$ alkyl—O—C$_{2-10}$ alkenyl; and
—C$_{1-10}$ alkyl or C$_{2-10}$ alkenyl substituted by one or more substituents selected from the group consisting of:
—OH;
-halogen;
—N(R$_3$)$_2$;
—CO—N(R$_3$)$_2$;
—CO—C$_{1-10}$ alkyl;
—N$_3$;
-aryl;
-heteroaryl;
-heterocyclyl;
—CO-aryl; and
—CO-heteroaryl;
each R$_3$ is independently selected from the group consisting of hydrogen and C$_{1-10}$ alkyl; and each R is independently selected from the group consisting of hydrogen, C$_{1-10}$ alkyl, C$_{1-10}$ alkoxy, halogen and trifluoromethyl,
or a pharmaceutically acceptable salt thereof.
This invention also provides compounds of Formula II

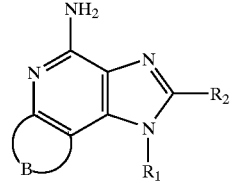

wherein
B is —NR—C(R)$_2$—C(R)$_2$—C(R)$_2$—; —C(R)$_2$—NR—C(R)$_2$—C(R)$_2$—; —C(R)$_2$—C(R)$_2$—NR—C(R)$_2$— or —C(R)$_2$—C(R)$_2$—C(R)$_2$—NR—;
R$_1$ is selected from the group consisting of:
-hydrogen;
—C$_{1-20}$ alkyl or C$_{2-20}$ alkenyl that is unsubstituted or substituted by one or more substituents selected from the group consisting of:
-aryl;
-heteroaryl;
-heterocyclyl;
—O—C$_{1-20}$ alkyl;
—O—(C$_{1-20}$ alkyl)$_{0-1}$-aryl;
—O—(C$_{1-20}$ alkyl)$_{0-1}$-heteroaryl;
—O—(C$_{1-20}$ alkyl)$_{0-1}$-heterocyclyl;
—C$_{1-20}$ alkoxycarbonyl;
—S(O)$_{0-2}$—C$_{1-20}$ alkyl;
—S(O)$_{0-2}$—(C$_{1-20}$ alkyl)$_{0-1}$-aryl;
—S(O)$_{0-2}$—(C$_{1-20}$ alkyl)$_{0-1}$-heteroaryl;
—S(O)$_{0-2}$—(C$_{1-20}$ alkyl)$_{0-1}$-heterocyclyl;
—N(R$_3$)$_2$;
—N$_3$;
oxo;
-halogen;
—NO$_2$;
—OH; and
—SH; and
—C$_{1-20}$ alkyl—NR$_3$—Q—X—R$_4$ or —C$_{2-20}$ alkenyl—NR$_3$—Q—X—R$_4$ wherein Q is —CO— or —SO$_2$—; X is a bond, —O— or —NR$_3$— and R$_4$ is aryl; heteroaryl; heterocyclyl; or —C$_{1-20}$ alkyl or C$_{2-20}$ alkenyl that is unsubstituted or substituted by one or more substituents selected from the group consisting of:
-aryl;
-heteroaryl;
-heterocyclyl;
—O—C$_{1-20}$ alkyl,
—O—(C$_{1-20}$ alkyl)$_{0-1}$-aryl;
—O—(C$_{1-20}$ alkyl)$_{0-1}$-heteroaryl;
—O—(C$_{1-20}$ alkyl)$_{0-1}$-heterocyclyl;
—C$_{1-20}$ alkoxycarbonyl;
—S(O)$_{0-2}$—C$_{1-20}$ alkyl;
—S(O)$_{0-2}$—C$_{1-20}$ alkyl)$_{0-1}$-aryl;
—S(O)$_{0-2}$—C$_{1-20}$ alkyl)$_{0-1}$-heteroaryl;
—S(O)$_{0-2}$—C$_{1-20}$ alkyl)$_{0-1}$-heterocyclyl;
—N(R$_3$)$_2$;
—NR$_3$—CO—O—C$_{1-20}$ alkyl;
—N$_3$;
oxo;
-halogen;

—NO$_2$;
—OH; and
—SH; or R$_4$ is

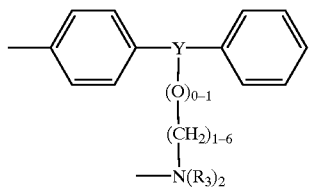

wherein Y is —N— or —CR—;
R$_2$ is selected from the group consisting of:
-hydrogen;
—C$_{1-10}$ alkyl;
—C$_{2-10}$ alkenyl;
-aryl
—C$_{1-10}$ alkyl —O—C$_{1-10}$-alkyl;
—C$_{1-10}$ alkyl—O—C$_{2-10}$ alkenyl; and
—C$_{1-10}$ alkyl or C$_{2-10}$ alkenyl substituted by one or more substituents selected from the group consisting of:
    —OH;
    -halogen;
    —N(R$_3$)$_2$;
    —CO—N(R$_3$)$_2$;
    —CO—C$_{1-10}$ alkyl;
    —N$_3$;
    -aryl;
    -heteroaryl;
    -heterocyclyl;
    —CO-aryl; and
    —CO-heteroaryl;
each R$_3$ is independently selected from the group consisting of hydrogen and C$_{1-10}$ alkyl; and
each R is independently selected from the group consisting of hydrogen, C$_{1-10}$ to alkyl, C$_{1-10}$ alkoxy, halogen and trifluoromethyl,
or a pharmaceutically acceptable salt thereof.

As used herein, the terms "alkyl", "alkenyl", and the prefix "-alk" are inclusive of both straight chain and branched chain groups and of cyclic groups, i.e. cycloalkyl and cycloalkenyl. These cyclic groups can be monocyclic or polycyclic and preferably have from 3 to 10 ring carbon atoms. Exemplary cyclic groups include cyclopropyl, cyclopentyl, cyclohexyl and adamantyl.

The term "aryl" as used herein includes carbocyclic aromatic rings or ring systems. Examples of aryl groups include phenyl, naphthyl, biphenyl, fluorenyl and indenyl. The term "heteroaryl" includes aromatic rings or ring systems that contain at least one ring hetero atom (e.g., O, S, N). Suitable heteroaryl groups include furyl, thienyl, pyridyl, quinolinyl, tetrazolyl, imidazo, and so on.

"Heterocyclyl" includes non-aromatic rings or ring systems that contain at least one ring hetero atom (e.g., O, S, N). Exemplary heterocyclic groups include pyrrolidinyl, tetrahydrofuranyl, morpholinyl, thiazolidinyl, and imidazolidinyl.

The aryl, heteroaryl and heterocyclyl groups may be unsubstituted or substituted by one or more substituents selected from the group consisting of C$_{1-20}$ alkyl, hydroxy, halogen, N(R$_3$)$_2$, NO$_2$, C$_{1-20}$ alkoxy, C$_{1-20}$ alkylthio, trihalomethyl, C$_{1-20}$ acyl, arylcarbonyl, heteroarylcarbonyl, (C$_{1-10}$ alkyl)$_{0-1}$-aryl, (C$_{1-10}$ alkyl)$_{0-1}$-heteroaryl, nitrile, C$_{1-20}$ alkoxycarbonyl, oxo, arylalkyl wherein the alkyl group has from 1 to 10 carbon atoms, and heteroarylalkyl wherein the alkyl group has from 1 to 10 carbon atoms.

The invention is inclusive of the compounds described herein in any of their pharmaceutically acceptable forms, including isomers such as diastereomers and enantiomers, salts, solvates, polymorphs, and the like.

PREPARATION OF THE COMPOUNDS

Compounds of Formulas I and II wherein A is =N—CR=CR—CR= or B is —NR—C(R)$_2$—C(R)$_2$—C(R)$_2$— and R, R$_1$ and R$_2$ are as defined above can be prepared according to Reaction Scheme I:

Reaction Scheme I

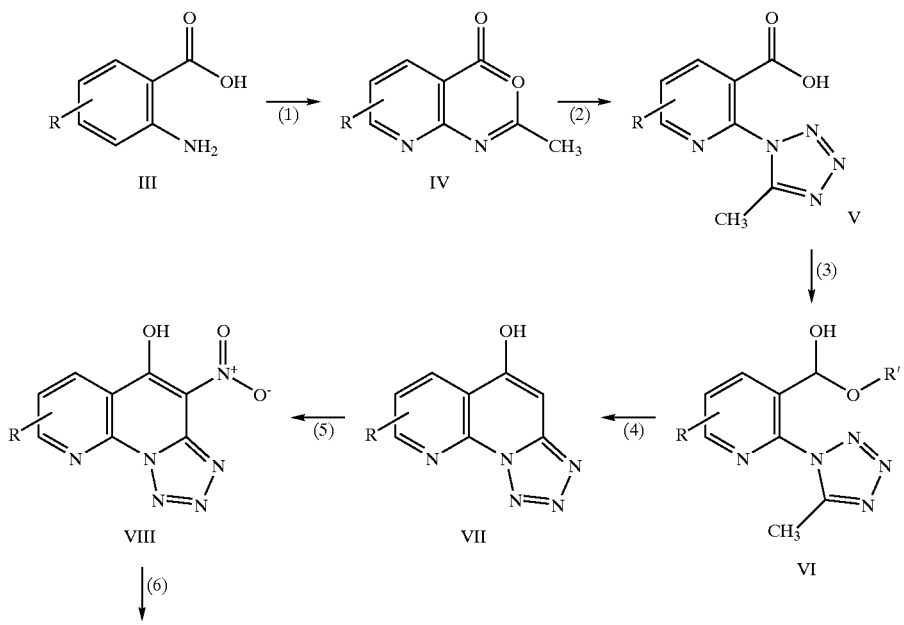

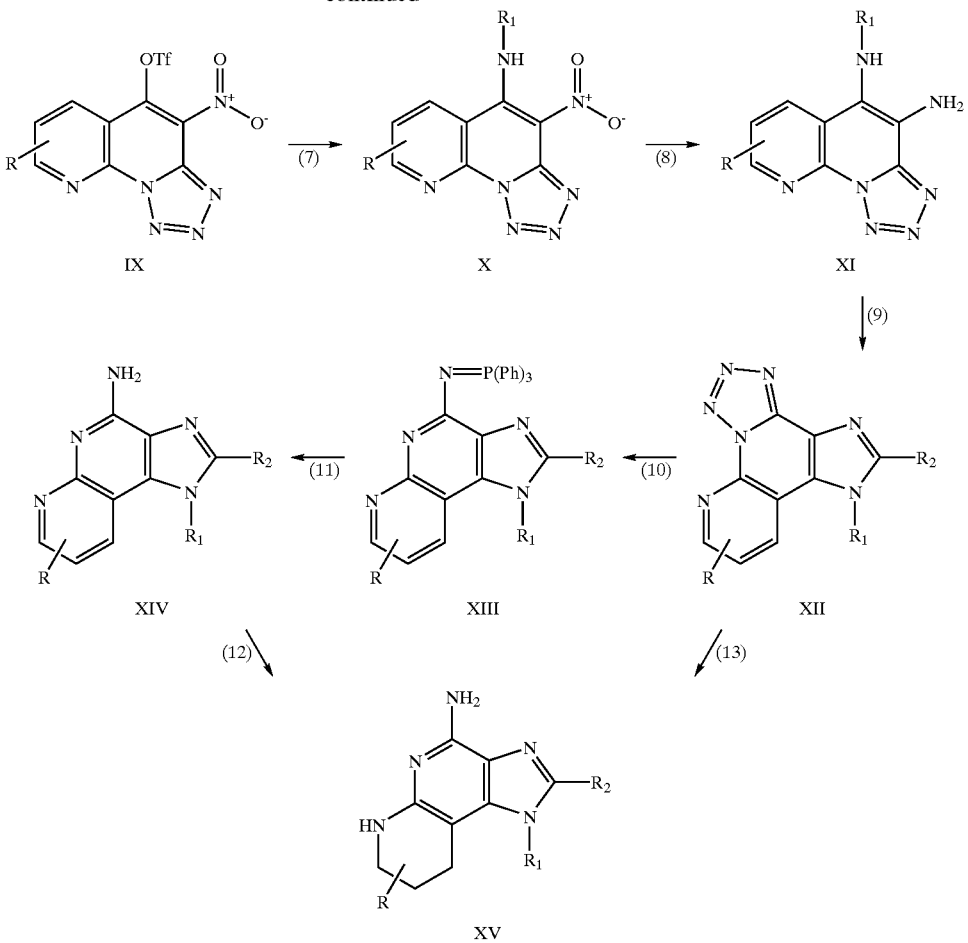

Many 2-aminonicotinic acids of Formula III are known (see, for example, U.S. Pat. No. 3,917,624). The compound where R is hydrogen is commercially available. In step (1) of Reaction Scheme I a 2-aminonicotinic acid of Formula III is reacted with acetic anhydride by heating to provide a 2-methyl-4H-pyrido[2,3-d][1,3]oxazin-4-one of Formula IV. The compound of Formula IV where R is hydrogen is known and its preparation has been disclosed in U.S. Pat. No. 3,314,941 (Littell), the disclosure of which is incorporated herein by reference.

In step (2) of Reaction Scheme I a compound of Formula IV is reacted with sodium azide in a suitable solvent such as acetic acid to provide a tetrazolyl nicotinic acid of Formula V. The reaction conveniently may be run at ambient conditions.

In step (3) of Reaction Scheme I an acid of Formula V is esterified to provide a compound of Formula VI. The esterification may be carried out using conventional methods. For example, the acid may be esterified in acetone using potassium carbonate and ethyl iodide.

In step (4) of Reaction Scheme I a compound of Formula VI is cyclized to provide a tetrazolo[1,5-a][1,8]naphthyridin-5-ol of Formula VII. The reaction may be carried out by reacting the compound of Formula VI with an alkoxide in a suitable solvent, e.g., potassium ethoxide in N,N-dimethylformamide, at ambient conditions.

In step (5) of Reaction Scheme I a compound of Formula VII is nitrated using a suitable nitrating agent such as nitric acid to provide a 4-nitrotetrazolo[1,5-a][1,8]naphthyridin-5-ol of Formula VIII.

In step (6) of Reaction Scheme I a compound of Formula VIII is converted to a triflate of Formula IX. The reaction is preferably carried out by combining a compound of Formula VIII with a base, preferably a tertiary amine such as triethyl amine, in a suitable solvent such as dichloromethane and then adding trifluoromethanesulfonic anhydride. The addition is preferably carried out in a controlled manner, e.g., adding dropwise at a reduced temperature such as, for example, at about 0° C. The product can be isolated by conventional methods or it can be carried on without isolation as described below in connection with step (7).

In step (7) of Reaction Scheme I a compound of Formula IX is reacted with an amine of formula $R_1NH_2$ where $R_1$ is as defined above to provide a 4-nitrotetrazolo[1,5-a][1,8]naphthyridin-5-amine of Formula X. The reaction can be carried out by adding the amine to the reaction mixture resulting from step (6). The reaction can also be carried out by adding the amine to a solution of the compound of Formula IX and a tertiary amine in a suitable solvent such as dichloromethiane.

In step (8) of Reaction Scheme I a compound of Formula X is reduced to provide a tetrazolo[1,5-a][1,8]naphthyridin-4,5-diamine of Formula XI. Preferably, the reduction is carried out using a conventional heterogeneous hydrogenation catalyst such as platinum on carbon or palladium on carbon. The reaction can conveniently be carried out on a Parr apparatus in a suitable solvent such as ethanol.

In step (9) of Reaction Scheme I a compound of Formula XI is reacted with a carboxylic acid or an equivalent thereof to provide a 1H-tetrazolo[1,5-a]imidazo[4,5-c][1,8]naphthyridine of Formula XII. Suitable equivalents to carboxylic acid include acid halides, orthoesters, and 1,1-dialkoxyalkyl alkanoates. The carboxylic acid or equivalent is selected such that it will provide the desired $R_2$ substituent in a compound of Formula XII. For example, diethoxymethylacetate will provide a compound where $R_2$ is hydrogen and valeryl chloride will provide a compound where $R_2$ is butyl. The reaction can be run in the absence of solvent, in a carboxylic acid such as acetic acid, or in an inert solvent in the presence of a carboxylic acid. The reaction is run with sufficient heating to drive off any alcohol or water formed as a byproduct of the reaction.

In step (10) of Reaction Scheme I a compound of Formula XII is reacted with triphenylphosphine to provide a N-triphenylphosphinyl-1H-imidazo[4,5-c][1,8]naphthyridin-4-amine of Formula XIII. The reaction can be carried out by combining a compound of Formula XII with triphenylphosphine in a suitable solvent such as 1,2-dichlorobenzene and heating.

In step (11) of Reaction Scheme I a compound of Formula XIII is hydrolyzed to provide a 1H-imidazo[4,5-c][1,8]naphthyridin-4-amine of Formula XIV which is a subgenus of Formula I. The hydrolysis can be carried out by conventional methods such as by heating in a lower alkanol in the presence of an acid. The product or a pharmaceutically acceptable salt thereof can be isolated using conventional methods.

In step (12) of Reaction Scheme I a compound of Formula XIV is reduced to provide a 6,7,8,9-tetrahydro-1H-imidazo[4,5-c][1,8]naphthyridin-4-amine of Formula XV which is a subgenus of Formula II. The reduction is carried out by suspending or dissolving a compound of Formula XIV in trifluoroacetic acid, adding a catalytic amount of platinum (IV)oxide, and then subjecting the mixture to hydrogen pressure. The reaction can be conveniently carried out in a Parr apparatus. The product or a pharmaceutically acceptable salt thereof can be isolated using conventional methods.

Alternatively, as illustrated in step (13) of Reaction Scheme I, a 6,7,8,9-tetrahydro-1H-imidazo[4,5-c][1,8]naphthyridin-4-amine of Formula XV can be prepared by reduction of a compound of Formula XII. The reduction is carried out by suspending or dissolving a compound of Formula XII in trifluoroacetic acid, adding a catalytic amount of platinum (IV)oxide, and then subjecting the mixture to hydrogen pressure. The reaction can be conveniently carried out in a Parr apparatus. As above, the product or a pharmaceutically acceptable salt thereof can be isolated using conventional methods.

Compounds of Formulas I and II wherein A is =CR—N=CR—CR= or B is —C(R)$_2$—NR—C(R)$_2$—C(R)$_2$—; R, $R_1$ and $R_2$ are as defined above can be prepared according to Reaction Scheme II.

Reaction Scheme II

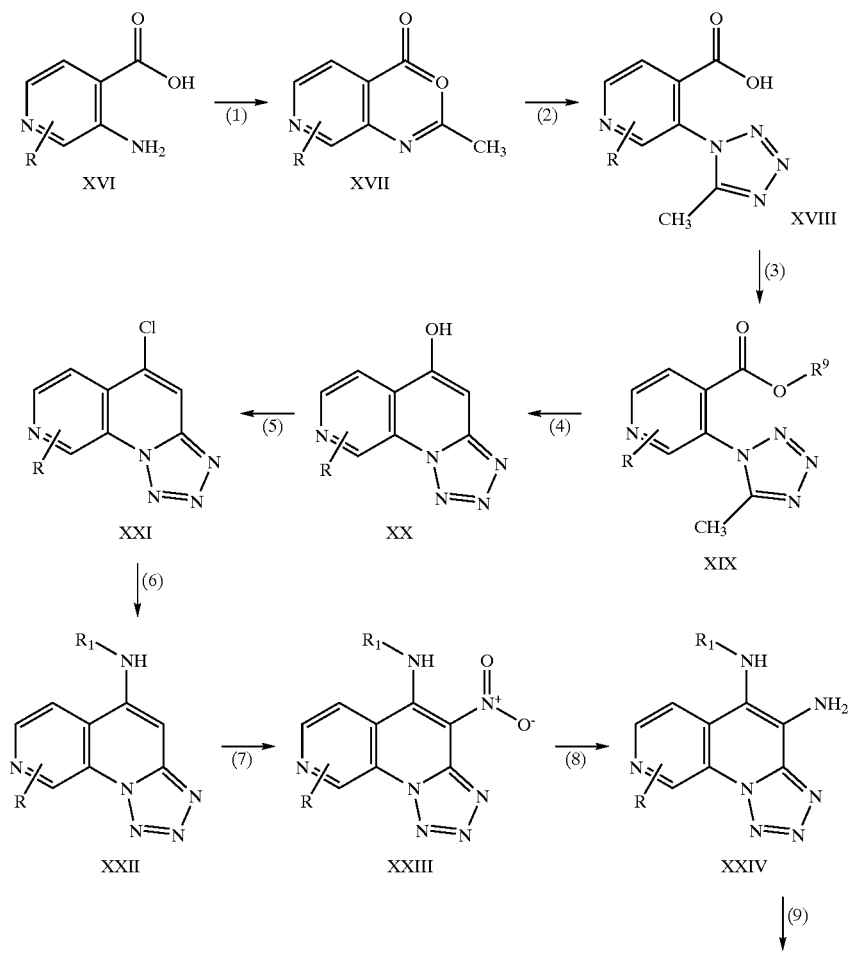

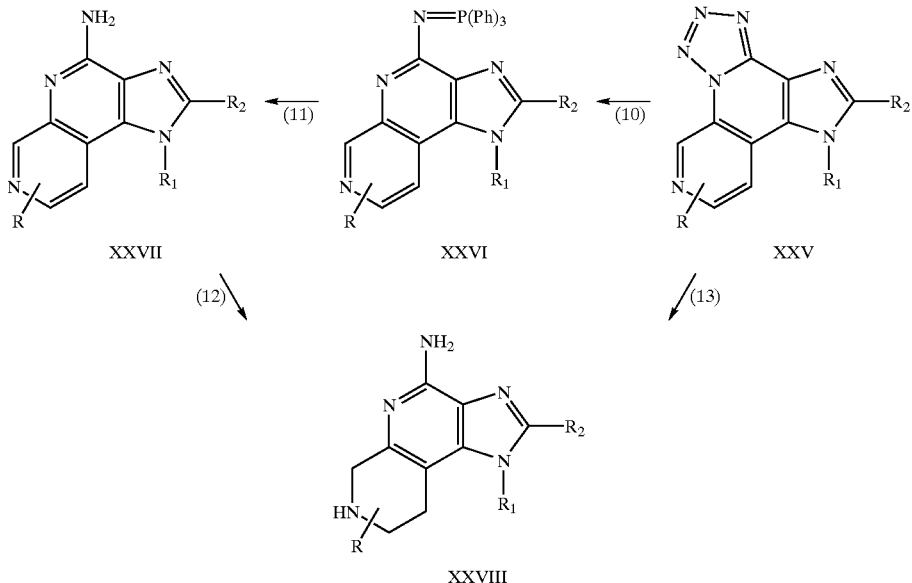

In step (1) of Reaction Scheme II a 3-aminoisonicotinic acid of Formula XVI is reacted with acetic anhydride by heating to provide a 2-methyl-4H-pyrido[3,4-d][1,3]oxazin-4-one of Formula XVII. The compound of Formula XVII where R is hydrogen is known and its preparation has been disclosed in Littell cited above.

In step (2) of Reaction Scheme II a compound of Formula XVII is reacted with sodium azide in a suitable solvent such as acetic acid to provide a tetrazolyl isonicotinic acid of Formula XVIII. The reaction conveniently may be run at ambient conditions.

In step (3) of Reaction Scheme II an acid of Formula XVIII is esterified to provide a compound of Formula XIX. The esterification may be carried out using conventional methods. For example, the acid may be esterified in acetone using potassium carbonate and ethyl iodide or by reacting with dimethylformamide diethyl acetal in a suitable solvent such as dichloromethane.

In step (4) of Reaction Scheme II a compound of Formula XIX is cyclized to provide a tetrazolo[1,5-a][1,7] naphthyridin-5-ol of Formula XX. The reaction may be carried out by reacting the compound of Formula XIX with an alkoxide in a suitable solvent, e.g., potassium ethoxide in N,N-dimethylformamide, at ambient conditions.

In step (5) of Reaction Scheme II a compound of Formula XX is chlorinated using a suitable chlorinating agent such as thionyl chloride, oxalyl chloride, phosphorus pentachloride or preferably phosphorus oxychloride to provide a 5-chlorotetrazolo[1,5-a][1,7]naphthyridine of Formula XXI. The reaction can be carried out in an inert solvent or if appropriate in neat chlorinating agent. Preferred reaction conditions involve reaction in neat phosphorus oxychloride with heating at about 90° C.

In step (6) of Reaction Scheme II a compound of Formula XXI is reacted with an amine of formula $R_1NH_2$ where $R_1$ is as defined above to provide a tetrazolo[1,5-a][1,7] naphthyridin-5-amine of Formula XXII. The reaction can be carried out by heating with an excess of the amine.

In step (7) of Reaction Scheme II a compound of Formula XXII is nitrated using a suitable nitrating agent such as nitric acid to provide a 4-nitrotetrazolo[1,5-a][1,7]naphthyridin-5-amine of Formula XXIII. Preferably the reaction is carried out in acetic acid with mild heating and an excess of nitric acid.

In step (8) of Reaction Scheme II a compound of Formula XXIII is reduced to provide a tetrazolo[1,5-a][1,7] naphthyridin-4,5-diamine of Formula XXIV. Preferably the reduction is carried out using an excess of sodium hydrogensulfide in a suitable solvent such as acetic acid.

In step (9) of Reaction Scheme II a compound of Formula XXIV is reacted with a carboxylic acid or an equivalent thereof to provide a 1H-tetrazolo[1,5-a]imidazo[4,5-c][1.7] naphthyridine of Formula XXV. Suitable equivalents to carboxylic acid include acid halides, orthoesters, and 1,1-dialkoxyalkyl alkanoates. The carboxylic acid or equivalent is selected such that it will provide the desired $R_2$ substituent in a compound of Formula XXV. For example, diethoxymethylacetate will provide a compound where $R_2$ is hydrogen and valeryl chloride will provide a compound where $R_2$ is butyl. The reaction can be run in the absence of solvent, in a carboxylic acid such as acetic acid, or in an inert solvent in the presence of a carboxylic acid. The reaction is run with sufficient heating to drive off any alcohol or water formed as a byproduct of the reaction.

In step (10) of Reaction Scheme II a compound of Formula XXV is reacted with triphenylphosphine to provide a N-triphenylphosphinyl-1H-imidazo[4,5-c][1,7] naphthyridin-4-amine of Formula XXVI. The reaction can be carried out by combining a compound of Formula XXV with triphenylphosphine in a suitable solvent such as 1,2-dichlorobenzene and heating.

In step (11) of Reaction Scheme II a compound of Formula XXVI is hydrolyzed to provide a 1H-imidazo[4,5-c][1,7]naphthyridin-4-amine of Formula XXVII which is a subgenus of Formula I. The hydrolysis can be carried out by conventional methods such as by heating in a lower alkanol in the presence of an acid. The product or a pharmaceutically acceptable salt thereof can be isolated using conventional methods.

In step (12) of Reaction Scheme II a compound of Formula XXVII is reduced to provide a 6,7,8,9-tetrahydro-1H-imidazo[4,5-c][1,7]naphthyridin-4-amine of Formula XXVIII which is a subgenus of Formula II. The reduction is carried out by suspending or dissolving a compound of Formula XXVII in trifluoroacetic acid, adding a catalytic amount of platinum (IV)oxide, and then subjecting the mixture to hydrogen pressure. The reaction can be conveniently carried out in a Parr apparatus. The product or a pharmaceutically acceptable salt thereof can be isolated using conventional methods.

Alternatively, as illustrated in step (13) of Reaction Scheme II, a 6,7,8,9-tetrahydro-1H-imidazo[4,5-c][1,7] naphthyridin-4-amine of Formula XXVIII can be prepared by reduction of a compound of Formula XXV. The reduction is carried out by suspending or dissolving a compound of Formula XXV in trifluoroacetic acid, adding a catalytic amount of platinum (IV)oxide, and then subjecting the mixture to hydrogen pressure. The reaction can be conveniently carried out in a Parr apparatus. The product or a pharmaceutically acceptable salt thereof can be isolated using conventional methods.

Compounds of Formulas I and II wherein A is =CR—CR=CR—N= or B is —C(R)$_2$—C(R)$_2$—C(R)$_2$—NR— and R, R$_1$ and R$_2$ are as defined above can be prepared according to Reaction Scheme III.

conventional methods or it can be carried on without isolation as described below in connection with step (2). The compound of Formula XXIX where R is hydrogen is known and its preparation has been disclosed in Hart, *Journal of the Chemical Society* pp. 212–214, (1956).

In step (2) of Reaction Scheme III a 4-chloro-3-nitro[1, 5]naphthyridine of Formula XXX is reacted with an amine of Formula R$_1$NH$_2$ where R$_1$ is as defined above to provide a 3-nitro[1,5]naphthyridin-4-amine of Formula XXXI. The reaction can be carried out by adding water then excess amine to the reaction mixture resulting from step (1) then heating on a steam bath. The reaction can also be carried out by adding excess amine to a solution of a compound of Formula XXX in a suitable solvent such as dichloromethane and optionally heating. The compound of Formula XXXI where R$_1$ is hydrogen is known and its preparation has been disclosed in Wozniak et al, *J. R. Neth. Chem. Soc.* 102 (12), pp. 511–13 (1983).

In step (3) of Reaction Scheme III a 3-nitro[1,5] naphthyridin-4-amine of Formula XXXI is reduced to provide a [1,5]naphthyridine-3,4-diamine of Formula XXXII. Preferably, the reduction is carried out using a conventional heterogeneous hydrogenation catalyst such as platinum on

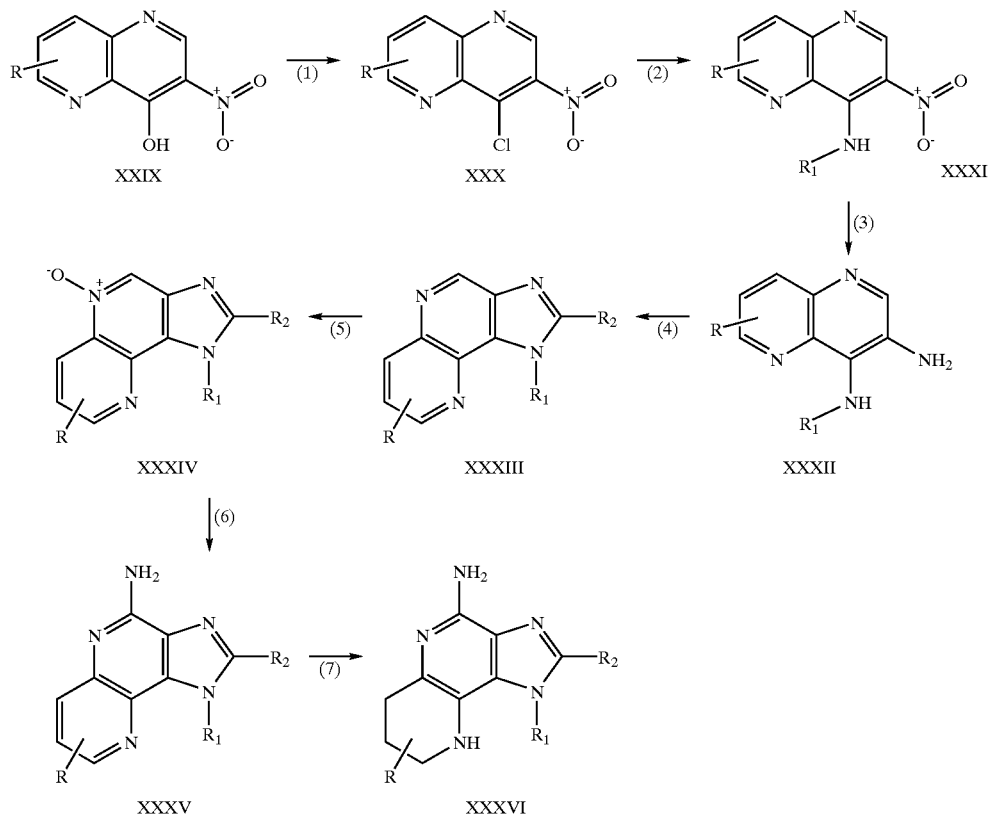

Reaction Scheme III

In step (1) of Reaction Scheme III a 3-mitro[1,5] naphthyridin-4-ol of Formula XXIX is chlorinated using a suitable chlorinating agent such as phosphorus oxychloride to provide a 4-chloro-3-nitro[1,5]naphthyridine of Formula XXX. The reaction can be carried out by reacting a compound of Formula XXIX with phosphorus oxychloride in a suitable solvent such as N,N-dimethylformamide with mild heating (~55° C.). The compound may be isolated by carbon or palladium on carbon. The reaction can conveniently be carried out on a Parr apparatus in a suitable solvent such as ethyl acetate.

In step (4) of Reaction Scheme III a compound of Formula XXXII is reacted with a carboxylic acid or an equivalent thereof to provide a 1H-imidazo[4,5-c][1,5] naphthyridine of Formula XXXIII. Suitable equivalents to carboxylic acid include acid halides, orthoesters, and 1,1- dialkoxyalkyl alkanoates. The carboxylic acid or equivalent is selected such that it will provide the desired $R_2$ substituent in a compound of Formula XXXIII. For example, diethoxymethylacetate will provide a compound where $R_2$ is hydrogen and trimethylorthovalerate will provide a compound where $R_2$ is butyl. The reaction can be run in the absence of solvent, in a carboxylic acid such as acetic acid, or in an inert solvent in the presence of an acid. The reaction is run with sufficient heating to drive off any alcohol or water formed as a byproduct of the reaction.

Alternatively, step (4) may be carried out by (i) reacting a compound of Formula XX,XII with an acylating agent; and then (ii) cyclizing the product. Part (i) involves reacting a compound of Formula XXXII with an acyl halide of formula $R_2C(O)X$ wherein $R_2$ is as defined above and X is chloro or bromo. The reaction can be carried out by adding the acyl halide in a controlled fashion (e.g. dropwise) to a solution of a compound of Formula XXXII in a suitable solvent such as dichloromethane at a reduced temperature (e.g., 0° C.). The resulting amide intermediate can be isolated by removal of the solvent. Part (ii) involves cyclizing the product of part (i) by reacting it with methanolic ammonia at an elevated temperature (e.g. 150° C.) and pressure.

In step (5) of Reaction Scheme III a compound of Formula XXXIII is oxidized to provide a 1H-imidazo[4,5-c][1,5]naphthyridine-5N-oxide of Formula XXXIV using a conventional oxidizing agent that is capable of forming N-oxides. Preferred reaction conditions involve reacting a solution of a compound of Formula XXXIII in chloroform with 3-chloroperoxybenzoic acid at ambient conditions.

In step (6) of Reaction Scheme III a compound of Formula XXXIV is aminated to provide a 1H-imidazo[4,5-c][1,5]naphthyridin-4-amine of Formula XXXV which is a subgenus of Formula I. Step (6) involves (i) reacting a compound of formula XXXIV with an acylating agent; and then (ii) reacting the product with an aminating agent. Part (i) of step (6) involves reacting an N-oxide with an acylating agent. Suitable acylating agents include alkyl- or arylsulfonyl chlorides (e.g., benzenesulfonyl chloride, methanesulfonyl choride, p-toluenesulfonyl chloride). Arylsulfonyl chlorides are preferred. p-Toluenesulfonyl chloride is most preferred. Part (ii) of step (6) involves reacting the product of part (i) with an excess of an aminating agent. Suitable aminating agents include ammonia (e.g., in the form of ammonium hydroxide) and ammonium salts (e.g., ammonium carbonate, ammonium bicarbonate, ammonium phosphate). Ammonium hydroxide is preferred. The reaction is preferably carried out by dissolving the N-oxide of Formula XXXIV in an inert solvent such as dichloromethane, adding the aminating agent to the solution, and then adding the acylating agent. Preferred conditions involve cooling to about 0° C. to about 5° C. during the addition of the acylating agent. The product or a pharmaceutically acceptable salt thereof can be isolated using conventional methods.

Alternatively step (6) may be carried out by (i) reacting a compound of Formula XXXIV with an isocyanate; and then (ii) hydrolyzing the product. Part (i) involves reacting the N-oxide with an isocyanate wherein the isocyanato group is bonded to a carbonyl group. Preferred isocyanates include trichloroacetyl isocyanate and aroyl isocyanates such as benzoyl isocyanate. The reaction of the isocyanate with the N-oxide is carried out under substantially anhydrous conditions by adding the isocyanate to a solution of the N-oxide in an inert solvent such as dichloromethane. The resulting product can be isolated by removal of the solvent. Part (ii) involves hydrolysis of the product from part (i). The reaction can be carried out by conventional methods such as heating in the presence of water or a lower alkanol optionally in the presence of a catalyst such as an alkali metal hydroxide or lower alkoxide.

In step (7) of Reaction Scheme III a compound of Formula XXXV is reduced to provide a 6,7,8,9-tetrahydro-1H-imidazo[4,5-c][1,5]naphthyridin-4-amine of Formula XXXVI which is a subgenus of Formula II. The reduction is carried out by suspending or dissolving a compound of Formula XXXV in trifluoroacetic acid, adding a catalytic amount of platinum (IV) oxide, and then subjecting the mixture to hydrogen pressure. The reaction can be conveniently carried out in a Parr apparatus. The product or a pharmaceutically acceptable salt thereof can be isolated using conventional methods.

Certain functional groups recited in connection with $R_1$ and $R_2$ may be incompatible with some of the reagents of Reaction Schemes I, II and III. Compounds containing such functional groups can be prepared by those skilled in the art using well known methods of functional group protection and manipulation. For example, amine groups may be protected when necessary by derivatizing with di-tert-butyl dicarbonate.

Some compounds of Formula I or Formula II containing certain functional groups may be readily prepared from other compounds of Formula I or Formula II. For example, compounds wherein the $R_1$ substituent contains an amide group may conveniently be prepared by reacting an acid chloride with a compound of Formula I or Formula II wherein the $R_1$ substituent contains a primary amine. Likewise, compounds wherein the RI substituent contains a urea group may be prepared by reacting an isocyanate with a compound of Formula I or Formula II wherein the $R_1$ substituent contains a primary amine. Further, compounds wherein the $R_1$ substituent contains a carbamate group may be prepared by reacting a chloroformate with a compound of Formula I or Formula II wherein the $R_1$ substituent contains a primary amine.

Certain of the intermediate compounds useful in the preparation of compounds of Formula I and Formula II have not been previously described. Therefore, the invention also provides intermediate compounds useful in the preparation of compounds of Formula I and Formula II. The structural formulas of these novel intermediates are set forth below. These compounds have the following structural formulas:

Intermediate Compound 1

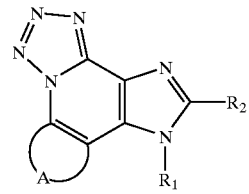

wherein $R_1$, $R_2$ and A are as defined above for compounds of Formula I and Formula II.

Intermediate Compound 2

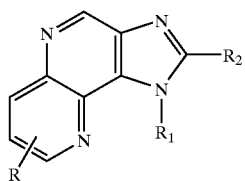

wherein R, $R_1$, and $R_2$ are as defined above for compounds of Formula I and Formula II.

Intermediate Compound 3

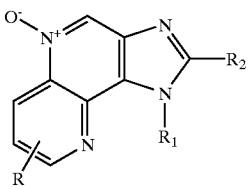

wherein R, $R_1$ and $R_2$ are as defined above for compounds of Formula I and Formula II.

Intermediate Compond 4

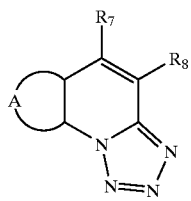

wherein $R_7$ is OH, halogen or $NHR_1$ (and A and $R_1$ are as defined above for compounds of Formula I) and $R_8$ is H, $NO_2$ or $NH_2$.

Intermediate Compound 5

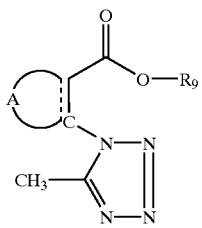

wherein A is as defined above for compounds of Formula I and $R_9$ is H or $C_{1-10}$ alkyl.

Intermediate Compound 6

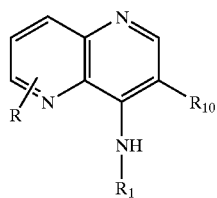

wherein R and $R_1$ are as defined above for compounds of Formula I and Formula II with the proviso that $R_1$ is other than hydrogen, and $R_{10}$ is $NO_2$ or $NH_2$.

Pharmaceutical Compositions and Biological Activity

Pharmaceutical compositions of the invention contain a therapeutically effective amount of a compound of Formula I or Formula II as defined above in combination with a pharmaceutically acceptable carrier. As used herein, the term "a therapeutically effective amount" means an amount of the compound sufficient to induce a therapeutic effect, such as cytokine induction or antiviral activity. Although the exact amount of active compound used in a pharmaceutical composition of the invention will vary according to factors known to those of skill in the art, such as the physical and chemical nature of the compound as well as the nature of the carrier and the intended dosing regimen, it is anticipated that the compositions of the invention will contain sufficient active ingredient to provide a dose of about 100 ng/kg to about 50 mg/kg, preferably about 10 µg/kg to about 5 µmg/kg of the compound to the subject. Any of the conventional dosage forms may be used, such as tablets, lozenges, parenteral formulations, syrups, creams, ointments, aerosol formulations, transdermal patches, transmucosal patches and so on.

The compounds of the invention have been shown to induce the production of certain cytokines in experiments performed according to the Test Method set forth below. This ability indicates that the compounds are useful as immune response modifiers that can modulate the immune response in a number of different ways, rendering them useful in the treatment of a variety of disorders.

Cytokines that are induced by the administration of compounds according to the invention generally include interferon (IFN) and tumor necrosis factor (TNF) as well as certain interleukins (IL). In particular, the compounds induce IFN-α, TNF-α, IL-1,6,10 and 12, and a variety of other cytokines. Among other effects, cytokines inhibit virus production and tumor cell growth, making the compounds useful in the treatment of tumors and viral diseases.

In addition to the ability to induce the production of cytokines, the compounds affect other aspects of the innate immune response. For example, natural killer cell activity may be stimulated, an effect that may be due to cytokine induction. The compounds may also activate macrophages, which in turn stimulates secretion of nitric oxide and the production of additional cytokines. Further, the compounds may cause proliferation and differentiation of B-lymphocytes.

Compounds of the invention also have an effect on the acquired immune response. For example, although there is not believed to be any direct effect on T cells or direct induction of T cell cytokines, the production of the T helper type 1 (Th1) cytokine IFN-γ is induced indirectly and the production of the Th2 cytokine IL-5 is inhibited upon administration of the compounds. This activity means that the compounds are useful in the treatment of diseases where upregulation of the Th1 response and/or downregulation of the Th2 response is desired. In view of the ability of compounds of Formula I and Formula II to inhibit T-helper-type 2 immune response, the compounds are expected to be useful in the treatment of atopy, e.g., atopic dermatitis, asthma, allergy, allergic rhinitis; as a vaccine adjuvant for cell mediated immunity; and possibly as a treatment for recurrent fungal diseases and chlamydia.

The immune response modifying effects of the compounds make them useful in the treatment of a wide variety of conditions. Because of their ability to induce cytokines such as IFN-α and TNF-α, the compounds are particularly useful in the treatment of viral diseases and tumors. This immunomodulating activity suggests that compounds of the invention are useful in treating diseases such as, but not limited to viral diseases e.g. genital warts, common warts, plantar warts, Hepatitis B, Hepatitis C, Herpes Simplex Type I and Type II, molluscum contagiosm, HIV, CMV, VZV, cervical intraepithelial neoplasia, human papillomavirus and associated neoplasias; fungal diseases, e.g. candida, aspergillus, cryptococcal meningitis; neoplastic diseases, e.g., basal cell carcinoma, hairy cell leukemia, Kaposi's sarcoma, renal cell carcinoma, squamous cell carcinoma, myelogenous leukemia, multiple myeloma, melanoma, non-Hodgkin's lymphoma, cutaneous T-cell lymphoma, and other cancers; parasitic diseases, e.g. pneumocystis carnii, cryptosporidiosis, histoplasmosis, toxoplasmosis, trypanosome infection, leishmaniasis; bacterial infections, e.g., tuberculosis, mycobacterium avium. Additional diseases or conditions that can be treated using the compounds of the invention include eczema, eosinophilia, essential thrombocythaemia, leprosy, multiple sclerosis, Ommen's syndrome, rheumatoid arthritis, systemic lupus erythematosis, discoid lupus, Bowen's disease and Bowenoid papulosis.

Accordingly, the invention provides a method of inducing cytokine biosynthesis in an animal comprising administering an effective amount of a compound of Formula I or Formula II to the animal. An amount of a compound effective to induce cytokine biosynthesis is an amount sufficient to cause one or more cell types, such as monocytes, macrophages, dendritic cells and B-cells to produce an amount of one or more cytokines such as, for example, INF-α, TNF-α, IL-1,6,10 and 12 that is increased over the background level of such cytokines. The precise amount will vary according to factors known in the art but is expected to be a dose of about 100 ng/kg to about 50 mg/kg, preferably about 10 µg/kg to about 5 mg/kg. The invention further provides a method of treating a viral infection in an animal comprising administering an effective amount of a compound of Formula I or Formula II to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount will vary according to factors known in the art but is expected to be a dose of 100 ng/kg to about 50 mg/kg, preferably about 10 µg/kg to about 5 mg/kg.

The invention is further described by the following examples, which are provided for illustration only and are not intended to be limiting in any way.

EXAMPLE 1

Compound of Formula V 2-(5-Methyl-1H-tetrazol-1-yl)nicotinic Acid

Part A:

2-Aminonicotinic acid (5 g, 36 mmole) was suspended in acetic anhydride (25 mL) then heated at reflux for 2 hours. The reaction mixture was concentrated under vacuum. The resulting residue was slurried with ethyl acetate and hexane then filtered to provide 5 g of 2-methyl-4H-pyrido[2,3-d][1,3]oxazin-4-one.

Part B:

The material from Part A was covered with acetic acid (75 mL), sodium azide (2 g) was added and the reaction mixture was stirred at ambient temperature over the weekend. The resulting precipitate was isolated by filtration then dried to provide 5.6 g of 2-(5-methyl-1H-tetrazol-1-yl)nicotinic acid as a white solid, m.p. 178–180° C. (gas evolution). Analysis: Calculated for $C_8H_7N_5O_2$: %C, 46.83; %H, 3.44; %N, 34.13; Found: %C, 46.38; %H, 3.36; %N, 34.01.

EXAMPLE 2

Compound of Formula VI

Ethyl 2-(5-Methyl-1H-tetrazol-1-yl)nicotinate 2-(5-Methyl-1H-tetrazol-1-yl)nicotinic acid (5.6 g, 27 mmole) was suspended in acetone (250 mL), potassium carbonate (5 g) and ethyl iodide (5 mL) were added and the reaction mixture was heated at reflux for 2 hours. The acetone was removed under vacuum. The residue was partitioned between water and dichloromethane. The dichloromethane layer was separated, dried, then concentrated under vacuum to provide 6.3 g of ethyl 2-(5-methyl-1H-tetrazol-1-yl)nicotinate.

EXAMPLE 3

Compound of Formula VII

Tetrazolo[1,5-a][1,8]naphthyridin-5-ol

Ethyl 2-(5-methyl-1H-tetrazol-1-yl)nicotinate (6.3 g, 27 mmole) was covered with N,N-dimethylformamide (50 mL), potassium ethoxide (4.5 g, 54 mmole) was added and the reaction mixture was stirred at ambient temperature for 2 hours. The reaction mixture was poured into ice water containing about 17 mL of acetic acid. The resulting precipitate was isolated by filtration, washed with water then dried to provide 4.5 g of tetrazolo[1,5-a][1,8]naphthyridin-5-ol as an off white solid, m.p. 236° (decomposition). Analysis: Calculated for $C_8H_5N_5O$: %C, 51.34; %H, 2.69; %N, 37.42; Found: %C, 51.23; %H, 2.77; %N, 37.25.

EXAMPLE 4

5-Chlorotetrazolo[1,5-a][1,8naphthyridine

Tetrazolo[1,5-a][1,8]naphthyridin-5-ol (0.5 g, 2.67 mmole) was suspended in phosphorous oxychloride (10 mL) and heated at reflux for 4 hours. The reaction mixture was concentrated under vacuum and the residue was poured into water. Dichloromethane was added and the aqueous layer was made basic with sodium bicarbonate. The dichloromethane layer was separated, dried over magnesium sulfate, filtered and then concentrated under vacuum. The resulting solid was recrystallized from toluene to provide 0.3 g of 5-chlorotetrazolo[1,5-a][1,8]naphthyridine as a solid, m.p. 229–230° C. (decomposition). Analysis: Calculated for $C_8H_4ClN_5$: %C, 46.73; %H, 1.96; %N, 34.06; Found: %C, 46.87; %H 1.54; %N, 33.93.

EXAMPLE 5

Compound of Formula VIII

4-Nitrotetrazolo[1,5-a][1,8]naphthyridin-5-ol

Nitric acid (1.33 mL of 16M) was added to a suspension of tetrazolo[1,5-a][1,8]naphthyridin-5-ol (4 g, 21 mmole) in acetic acid (50 mL). The reaction mixture was heated on a steam bath for 5 minutes then cooled to ambient temperature. Sodium acetate (0.3 eq) in a small amount of water was added to the reaction mixture. The resulting solid was isolated by filtration and dried to provide 5 g of 4-nitrotetrazolo[1,5-a][1,8]naphthryidin-5-ol as a solid, m.p. 278° C. (decomposition). Analysis: Calculated for $C_8H_4N_6O_3$+1.1 $H_2O$: %C, 38.12; %H, 2.48; %N, 33.35; Found: %C, 37.99; %H, 2.41; %N, 32.82.

EXAMPLE 6

Compound of Formula X $N^5$-(2-Methylpropyl)-4-nitrotetrazolol[1,5-a][1,8] naphthyridin-5-amine 4-Nitrotetrazolo[1,5-a][1,8]naphthryidin-5-ol (3 g, 13 mmole) was suspended in dichloromethane (3.8 mL), triethylamine (1.8 mL) was added, and the reaction mixture was cooled in an ice bath. Trifluoromethanesulfonic anhydride (2.2 mL) was added dropwise. Isobutylamine (3.8 mL) was added in a single aliquot and the reaction mixture exothermed. The reaction mixture was partitioned between dichloromethane and aqueous sodium bicarbonate. The dichloromethane layer was separated, dried over magnesium sulfate then filtered through a layer of silica gel. The silica gel was eluted first with dichloromethane then with 5% methanol in dichloromethane. The eluant was evaporated to provide $N^5$-(2-methylpropyl)-4-nitrotetrazolo[1,5-a][1,8]naphthyridine-5-amine as a yellow solid, m.p. 171° C. (decomposition). Analysis: Calculated for $C_{12}H_{13}N_7O_2$: %C, 50.17; %H 4.56; %N, 34.13; Found: %C, 49.84; %H, 4.51; %N, 33.88.

EXAMPLE 7

Compound of Formula XI $N^5$-(2-Methylpropyl)tetrazolo[1,5-a][1,8] naphthyridin-4,5-diamine A catalytic amount of 5% platinum on carbon was added to a suspension of $N^5$-(2-methylpropyl)-4-nitrotetrazolo[1,5-a][1,8]naphthyridine-5-amine (2.45 g, 8.5 mmoles) in ethanol (120 mL). The reaction mixture was reduced on a Parr apparatus at 50 psi (3.5 Kg/cm$^2$) hydrogen for 2 hours. The reaction mixture was filtered to remove the catalyst. The filtrate was concentrated under vacuum to provide $N^5$-(2-methylpropyl)tetrazolo[1,5-a][1,8]naphthyridin-4,5-diamine as an oil.

EXAMPLE 8

Compound of Formula XII 1-(2-Methylpropyl)-1H-tetrazolo[1,5-a]imidazo[4,5-c][1,8]naphthyridine The $N^5$-(2-methylpropyl)tetrazolo[1,5-a][1,8]naphthyridin-4,5-diamine from Example 7 was combined with diethoxymethylacetate (2 mL) and heated on a steam bath for 3 hours. The reaction mixture was allowed to stand at ambient temperature overnight and then it was diluted with dichloromethane and methanol. The resulting solution was heated to remove the dichloromethane and reduce the volume of methanol to 50 mL and then cooled. The resulting precipitate was isolated by filtration to provide 1.2 g of 1-(2-Methylpropyl)-1H-tetrazolo[1,5-a]imidazo[4,5-c][1,8]naphthyridine as a solid, m.p. 248–250° C. (decomposition). Analysis: Calculated for $C_{13}H_{13}N_7$: %C, 58.42; %H, 4.90; %N, 36.68; Found: %C, 58.04; %H, 4.79; %N, 36.23.

EXAMPLE 9

Compound of Formula I 1-(2-Methylpropyl)-1H-imidazo[4,5-c][1,8] naphthyridin-4-amine Hydrate

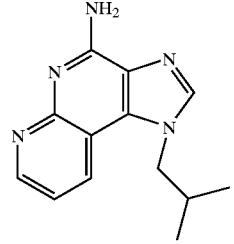

Part A:
Triphenylphosphine (1.0 g, 3.7 mmole) was added to a solution of 1-(2-methylpropyl)-1H-tetrazolo[1,5-a]imidazo[4,5-c][1,8]naphthyridine (0.5 g, 1.87 mmole) in 1,2-dichlorobenzene (15 mL). The reaction mixture was heated at reflux for 2 hours then concentrated under vacuum to remove the majority of the 1,2-dichlorobenzene. The residue was slurried with hexanes for 30 minutes. The resulting solid 1-(2-methylpropyl)-N-triphenylphosphinyl-1H-imidazo[4,5-c][1,8]naphthyridin-4-amine was isolated by filtration and dried.

Part B:
The 1-(2-methylpropyl)-N-triphenylphosphinyl-1H-imidazo[4,5-c][1,8]naphthyridin-4-amine from Part A was dissolved in methanol (15 mL). Hydrochloric acid (10 mL of 0.6N) was added and the reaction mixture was heated at reflux for 1 hour. The reaction mixture was concentrated under vacuum. The residue was diluted with water then made basic with sodium bicarbonate. The resulting solid was isolated by filtration, slurried with ether and then isolated by filtration. The solid was suspended in toluene (25 mL). The suspension was heated to reflux then diluted with methanol (10 mL) to dissolve the solid. The solution was refluxed to remove the methanol then cooled to ambient temperature. The resulting precipitate was isolated by filtration then coated onto silica gel. The silica gel was eluted with 10–20% methanol in ethyl acetate. The eluant was concentrated to dryness. The resulting material was recrystallized from methanol and water to provide 0.35 g 1-(2-methylpropyl)-1H-imidazo[4,5-c][1,8]naphthyridin-4-amine hydrate as a solid, m.p. 325–33° C. (decomposition). Analysis: Calculated for $C_{13}H_{15}N_5$+¼$H_2O$: %C, 63.52; %H, 6.35; %N, 28.49; Found: %C, 64.02; %H, 5.87; %N, 28.23.

EXAMPLE 10

Compound of Formula II 6,7,8,9-Tetrahydro-1-(2-methylpropyl)-1H-imidazo [4,5-c][1,8]naphthyridin-4-amine

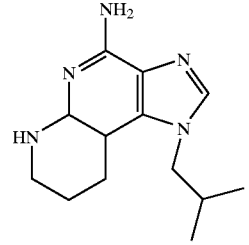

Platinum oxide catalyst was added to a solution of 1-(2-methylpropyl)-1H-tetrazolo[1,5-a]imidazo[4,5-c][1,8]naphthyridine in trifluoroacetic acid (30 mL). The reaction mixture was reduced on a Parr apparatus at 50 psi (3.5 Kg/cm$^2$) hydrogen pressure for 5 hours. The reaction mixture was filtered to remove the catalyst. The filtrate was concentrated under vacuum. The residue was combined with water and sodium bicarbonate. The resulting precipitate was isolated by filtration. The solid was dissolved in 1N hydrochloric acid and charcoal filtered. The filtrate was treated with 10% sodium hydroxide. The resulting precipitate was isolated by filtration then recrystallized from ethyl acetate/methanol. The recrystallized material was dissolved in dichloromethane/methanol and placed on a silica gel column. The column was eluted with 10% methanol in ethyl acetate. The eluant was concentrated under vacuum and the residue was recrystallized from methanol/water to provide 0.9 g of 6,7,8,9-tetrahydro-1-(2-methylpropyl)-1H-imidazo[4,5-c](1,8]naphthyridin-4-amine as a solid, m.p. 231–233° C. Analysis: Calculated for $C_{13}H_{19}N_5$: %C, 63.65; %H, 7.81; %N, 28.55; Found: %C, 62.99; %H, 7.74; %N, 28.33.

EXAMPLE 11

Compound of Formula XII

2-Butyl-1-(2-methylpropyl)-1H-tetrazolo[1,5-a]imidazo[4,5-c][1,8]naphthyridine

A catalytic amount of 5% platinum on carbon was added to a suspension of N$^5$-(2-methylpropyl)-4-nitrotetrazolo[1,5-a][1,8]naphthyridine-5-amine (5 g, 17.4 mmoles) in ethanol (300 mL). The reaction mixture was reduced on a Parr apparatus at 50 psi (3.5 Kg/cm$^2$) hydrogen for 2 hours. The reaction mixture was filtered to remove the catalyst. The filtrate was concentrated under vacuum to provide N$^5$-(2-methylpropyl)tetrazolo(1,5-a][1,8]naphthyridin-4,5-diamine as an oil.

The oil was covered with acetic acid (300 mL), valeryl chloride (2.1 mL, 17.4 mmole) was added and the resulting mixture was heated at reflux overnight. The reaction mixture was concentrated under vacuum. The resulting residue was taken up in dichloromethane, washed with sodium bicarbonate, dried over magnesium sulfate then concentrated under vacuum. The residue was purified using flash chromatography (silica gel; eluting with 2–3% methanol in dichloromethane). The isolated product was purified further using preparatory high performance liquid chromatography eluting with 2% methanol in dichloromethane to provide 2-butyl-1-(2-methylpropyl)-1H-tetrazolo[1,5-a]imidazo[4,5-c][1,8]naphthyridine as a solid, m.p. 182–184° C. Analysis: Calculated for $C_{17}H_{21}N_7$: %C, 63.14; %H, 6.55; %N, 30.32; Found: %C, 63.45; %H, 6.60; %N, 30.40.

EXAMPLE 12

Compound of Formula I

2-Butyl-1-(2-methylpropyl)-1H-imidazo[4,5-c][1,8]naphthyridin-4-amine

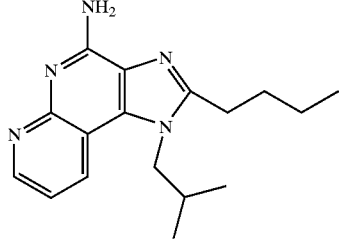

Triphenylphosphine (0.9 g, 3.7 mmole) was added to a solution of 2-butyl-1-(2-methylpropyl)-1H-tetrazolo[(0.6 g, 1.8 mmole) in 1,2-dichlorobenzene (15 mL). The resulting mixture was heated at reflux for 2 hours then concentrated under vacuum to remove most of the 1,2-dichlorobenzene. The residue was slurred with hexanes then taken up in dichloromethane and filtered through a layer of silica gel. The silica gel was eluted initially with dichloromethane to remove the 1,2-dichlorobenzene and then with 10% methanol in dichloromethane to recover 2-butyl-1-(2-methylpropyl)-N-triphenylphosphinyl-1H-imidazo[4,5-c][1,8]naphthyridin-4-amine.

The 2-butyl-1-(2-methylpropyl)-N-triphenylphosphinyl-1H-imidazo[4,5-c][1,8]naphthyridin-4-amine was taken up in methanol (15 mL), combined with hydrochloric acid (10 mL of 0.6N), and then heated at reflux for 1 hour. The methanol was removed under vacuum. The residue was combined with water and 10% hydrochloric acid then filtered. The filtrate was neutralized with 10% sodium hydroxide. The resulting precipitate was isolated by filtration and dried. The resulting solid was refluxed in toluene. The volume of toluene was reduced and the product was allowed to crystallize out under an argon atmosphere to provide 0.25 g of 2-butyl-1-(2-methylpropyl)-1H-imidazo[4,5-c][1,8]naphthyridin-4-amine hemihydrate, m.p. 237–240° C. Analysis: Calculated for $C_{17}H_{23}N_5+\frac{1}{2}H_2O$: %C, 68.66; %H, 7.79; %N, 23.55; Found: %C, 66.80; %H, 7.62; %N, 23.46.

EXAMPLE 13

Compound of Formula II

2-Butyl-6,7,8,9-tetrahydro-1-(2-methylpropyl)-1H-imidazo[4,5-c][1,8]naphthyridin-4-amine

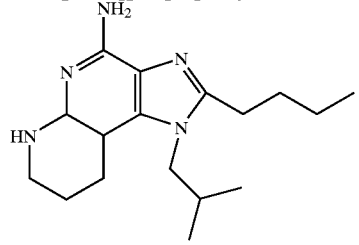

A catalytic amount of platinum oxide was added to a solution of 2-butyl-1-(2-methylpropyl)-1H-imidazo[4,5-c][1,8]naphthyridin-4-amine (2.0 g, 6.2 mmole) in trifluoroacetic acid (30 mL). The reaction mixture was reduced on a Parr apparatus under 50 psi (3.5 Kg/cm$^2$) hydrogen pressure. The reaction mixture was filtered to remove the catalyst. The filtrate was concentrated under vacuum. The residue was combined with water, sodium bicarbonate and 10% sodium hydroxide. An oil was recovered and purified using reverse phase high performance liquid chromatography eluting with 30:70 buffer (7.68 g potassium phosphate, monobasic; 1.69 g of sodium hydroxide, 1 L of water):methanol to provide 2-butyl-6,7,8,9-tetrahydro-1-(2-methylpropyl)-1H-imidazo[4,5-c][1,8]naphthyridin-4-amine hemihydrate as a solid, m.p. 81–84° C. Calculated for $C_{17}H_{27}N_5 30 \frac{1}{2}H_2O$: %C, 65.77; %H, 9.09; %N, 22.56; Found: %C, 65.57; %H,.9.15; %N, 22.53.

EXAMPLE 14

Compound of Formula XVIII 3-(5-Methyl-1H-tetrazol-1-yl)pyridine-4-carboxylic Acid 3-Aminopyridine-4-carboxylic acid (50.0 g, 0.36 mol) was suspended in acetic anhydride (250 mL) then heated at reflux for 2 hours. The reaction mixture was concentrated under vacuum. The solid residue was slurried with heptane then concentrated under vacuum. The resulting solid was covered with acetic acid (300 mL), then sodium azide (23.5 g, 0.36 mol) was added. The reaction exothermed to 50° C. The reaction mixture was allowed to stir at ambient temperature overnight. The precipitate was isolated by filtration then slurried with methanol and filtered. The solid was dissolved in 10% sodium hydroxide. The solution was heated on a steam bath for 30 minutes, allowed to cool to ambient temperature then neutralized with 6N hydrochloric acid. The resulting precipitate was isolated by filtration, washed with water and dried to provide 64.5 g of 3-(5-methyl-1H-tetrazol-1-yl)pyridine-4-carboxylic acid as an off white solid, m.p. 214–215° C. (decomposition).

EXAMPLE 15

Compound of Formula XIX

Ethyl 3-(5-Methyl-1H-tetrazol-1-yl)pyridine4-carboxylate

Dimethylformamide diethyl acetal (46 mL) was added to a suspension of 3-(5-methyl-1H-tetrazol-1-yl)pyridine-4-carboxylic acid (36 g) in dichloromethane (800 mL). The reaction mixture was stirred at ambient temperature overnight then washed six times with water (500 mL), dried over magnesium sulfated, and concentrated under vacuum. The residue was recrystallized from ethyl acetate/hexanes to provide 40 g of ethyl 3-(5-methyl-1H-tetrazol-1-yl)pyridine-4-carboxylate as a solid.

EXAMPLE 16

Compound of Formula XX

Tetrazolo[1,5-a][1,7]naphthyridin-5-ol Hydrate

Potassium ethoxide (20.2 g) was added to a mixture of ethyl 3-(5-methyl-1H-tetrazol-1-yl)pyridine-4-carboxylate (28 g) and dimethylformamide (280 mL). The reaction mixture was allowed to stir at ambient temperature overnight then poured into cold dilute acetic acid. The resulting precipitate was collected, washed with water and dried to provide 22.4 g of tetrazolo[1,5-a][1,7]naphthyridin-5-ol hydrate as a solid, m.p. 247–248° C. (decomposition). Analysis: Calculated for $C_8H_5N_5O$: %C, 46.83; %H, 3.44; %N, 34.13; Found: %C, 46.48; %H, 3.42; %N, 34.03.

EXAMPLE 17

Compound of Formula XXI

5-Chlorotetrazolo[1,5-a][1,7]naphthyridine

A suspension of tetrazolo[1,5-a][1,7]naphthyridin-5-ol (3.5 g) in phosphorous oxychloride (15 mL) was heated at 90° C. for 2 hours. The reaction mixture was concentrated under vacuum. The residue was poured into ice water, dichloromethane was added followed by the addition of 10% sodium hydroxide to neutral pH. The product was partitioned into dichloromethane. The dichloromethane layer was separated, dried over magnesium sulfate then concentrated under vacuum to provide 3.8 g of 5-chlorotetrazolo[1,5-a][1,7]naphthyridine as a solid, m.p. 176–177° C. Analysis: Calculated for $C_8H_4ClN_5$: %C, 46.73; %H, 1.96; %N, 34.06; Found: %C, 46.80; %H, 2.16; %N, 34.45.

EXAMPLE 18

Compound of Formula XXII

$N^5$-(2-Methylpropyl)tetrazolo[1,5-a][1,7]naphthyridin-5-amine

A suspension of 5-chlorotetrazolo[1,5-a][1,7]naphthyridine (20 g) in isobutylamine (100 mL) was heated at reflux for several hours. The reaction mixture was concentrated under vacuum. The residue was taken up in dichloromethane, washed with water, dried over magnesium sulfate then concentrated under vacuum. The residue was recrystallized from toluene to give a material that was a mixture by thin layer chromatography. The material was purified by flash chromatography, silica gel eluting with dichloromethane, 5–20% ethyl acetate in dichloromethane, and 10% methanol in dichloromethane. The fractions with the slower moving material were concentrated to provide $N^5$-(2-methylpropyl)tetrazolo[1,5-a][1,7]naphthyridin-5-amine as a solid, m.p. 220–221° C. Analysis: Calculated for $C_{12}H_{14}N_6$: %C, 59.49; %H, 5.82; %N, 34.69; Found: %C, 59.35; %H, 5.89; %N, 34.88.

EXAMPLE 19

Compound of Formula XXIII

$N^5$-(2-Methylpropyl)-4-nitrotetrazolo[1,5-a][1,7]naphthyridin-5-amine

Nitric acid (2 equivalents of 16M) was added to a solution of $N^3$-(2-methylpropyl)tetrazolo[1,5-a][1,7]naphthyridin-5-amine (2.0 g, 8.26 mmol) in acetic acid. The reaction mixture was heated on a steam bath for about an hour then concentrated under vacuum. The residue was poured into ice water and the resulting mixture was neutralized with sodium bicarbonate. The resulting precipitate was extracted with dichloromethane. The dichloromethane extracts were combined, washed with water, and dried over magnesium sulfate. Thin layer chromatography indicated a mixture so the material was filtered through a layer of silica gel eluting with 5% ethyl acetate in dichloromethane. The reaction was rerun on 4 g of starting material but using only one equivalent of nitric acid. The resulting material was also a mixture. The material from both reactions was combined then purified by flash chromatography eluting with mixtures of hexanes/ethyl acetate. The fractions containing the slower moving material were combined to provide about 0.3 g of $N^5$-(2-methylpropyl)-4-nitrotetrazolo[1,5-a][1,7]naphthyridin-5-amine as a yellow solid, m.p. 173–174° C. Analysis: Calculated for $C_{12}H_{13}N_7O_2$: %C, 50.17; %H, 4.56; %N, 34.13; Found: %C, 49.85; %H, 4.53; %N, 34.26.

EXAMPLE 20

Compound of Formula XXIV

$N^5$-(2-Methylpropyl)tetrazolo[1,5-a][1,7]naphthyridin-4,5-diamine $N^5$-(2-Methylpropyl)-4-nitrotetrazolo[1,5-a][1,7]naphthyridin-5-amine (1.5 g, 5.22 mmol) was suspended in acetic acid (75 mL). An excess of sodium hydrogen sulfide was dissolved in a minimum of water and added to the suspension. The reaction mixture turned red and all of the material went into solution. The reaction mixture was extracted twice with dichloromethane (150 mL). The extracts were combined, washed with water, dried over magnesium sulfate, filtered and concentrated under vacuum to provide 1.22 g of $N^5$-(2-methylpropyl)tetrazolo[1,5-a][1,7]naphthyridin-4,5-diamine as a light yellow solid, m.p.

203–204.5° C. Analysis: Calculated for: $C_{12}H_{15}N_7$: %C, 56.02; %H, 5.88; %N, 38.11; Found: %C, 55.68; %H, 5.81; %N, 37.74.

EXAMPLE 21

Compound of Formula XXV 1-(2-Methylpropyl)-1H-tetrazolo[1,5-a]imidazo[4,5-c][1,7]naphthyridine $N^5$-(2-Methylpropyl)tetrazolo[1,5-a][1,7]naphthyridin-4,5-diamine (1.1 g, 4.3 mmol) was combined with diethoxymethylacetate (2 mL) and heated on a steam bath overnight. The reaction mixture was partitioned between dichloromethane and ammonium hydroxide. The dichloromethane layer was separated, washed with water, dried over magnesium sulfate and concentrated under vacuum. The residue was recrystallized from ethyl acetate/hexane to provide 0.85 g of 1-(2-methylpropyl)-1H-tetrazolo[1,5-a]imidazo[4,5-c][1,7]naphthyridine as a solid, m.p. 181–182.5° C. Analysis: Calculated for $C_{13}H_{13}N_7$: %C, 58.42; %H, 4.90; %N, 36.68; Found: %C, 58.87; %H, 5.04; %N, 36.13.

EXAMPLE 22

Compound of Formula I 1-(2-Methylpropyl)-1H-imidazo[4,5-c][1,7]naphthyridin-4-amine

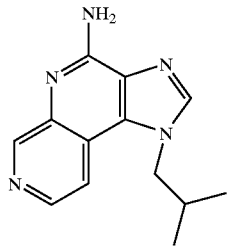

Parr A:

Triphenylphosphine (0.49 g, 1.8 mmol) was added to a suspension of 1-(2-methylpropyl)-1H-tetrazolo[1,5-a]imidazo[4,5-c][1,7]naphthyridine (0.24 g, 0.9 mmol) in dichlorobenzene (15 mL). The reaction mixture was heated at reflux overnight then concentrated under vacuum. The residue was slurried with hexane and the resulting solid 1-(2-methylpropyl)-N-triphenylphosphinyl-1H-imidazo[4,5-c][1,7]naphthyridin-4-amine was isolated by filtration.

Part B:

The 1-(2-methylpropyl)-N-triphenylphosphinyl-1H-imidazo[4,5-c][1,7]naphthyridin-4-amine from Part A was dissolved in methanol (30 mL). Hydrochloric acid (3 mL of 3N) was added to the solution and the reaction mixture was heated at reflux overnight before being concentrated under vacuum to remove the methanol. The aqueous residue was neutralized with sodium bicarbonate then extracted with dichloromethane. The extract was dried over magnesium sulfate then concentrated under vacuum. The residue was purified by flash chromatography (silica gel eluting with 5–10% methanol in dichloromethane) to provide 0.15 g of 1-(2-methylpropyl)-1H-imidazo[4,5-c][1,7]naphthyridin4-amine as a solid, m.p. 306–307° C. Analysis: Calculated for $C_{13}H_{15}N_5$: %C, 64.71; %H, 6.27; %N, 29.02; Found: %C, 65.10; %H, 6.28; %N, 28.70.

EXAMPLE 23

Compound of Formula II 6,7,8,9-Tetrahydro-1-(2-methylpropyl)-1H-imidazo[4,5-c][1,7]naphthyridin-4-amine

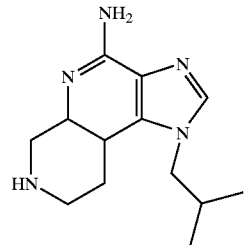

A catalytic amount of platinum oxide was added to a solution of 1-(2-methylpropyl)-1H-imidazo[4,5-c][1,7]naphthyridin-4-amine (0.4 g, 1.66 mol)) in trifluoroacetic acid. The reaction mixture was reduced on a Parr apparatus at 50 psi (3.5 Kg/cm$^2$) hydrogen pressure overnight. The reaction mixture was filtered and washed with methanol to remove the catalyst. The filtrate was concentrated under vacuum. The residue was combined with dichloromethane and aqueous sodium bicarbonate was added until the mixture was basic. The dichloromethane layer was separated. The aqueous layer was extracted five times with dichloromethane (100 mL). The dichloromethane extracts were combined, dried over magnesium sulfate and concentrated under vacuum. The resulting residue was recrystallized from toluene to provide 0.34 g of 6,7,8,9-tetrahydro-1-(2-methylpropyl)-1H-imidazo[4,5-c][1,7]naphthyridin-4-amine as a solid, m.p. 220–223° C. Analysis: Calculated for $C_{13}H_{19}N_5 + \frac{1}{4}H_2O$: %C, 62.50 %H, 7.87; %N, 28.03; Found: %C, 62.50; %H, 7.72; %N, 27.46.

EXAMPLE 24

Compound of Formula XXV

2-Methyl-1-(2-methylpropyl)-1H-tetrazolo[1,5-a]imidazo[4,5-c][1,7]naphthyridine

Acetic anhydride (2–3 mL) was added to a solution of N-(2-methylpropyl)tetrazolo[1,5-a][1,7]naphthyridin-4,5-diamine (0.8 g, 3.1 mmole) in acetic acid. The reaction mixture was heated on a steam bath for several hours then concentrated under vacuum. The residue was partitioned between dichloromethane and water. The aqueous layer was made basic with 10% sodium hydroxide then the dichloromethane layer was separated, dried over magnesium sulfate and concentrated under vacuum. The residue was purified by flash chromatography (silica gel eluting with 2–5% methanol in dichloromethane) to provide 0.25 g of 2-methyl-1-(2-methylpropyl)-1H-tetrazolo[1,5-a]imidazo[4,5-c][1,7]naphthyridine as a solid, m.p. 157–158° C. Analysis: Calculated for $C_{14}H_{15}N_7$: %C, 59.77; %H, 5.37; %N, 34.85; Found: %C, 59.64; %H, 5.48; %N, 34.98.

EXAMPLE 25

Compound of Formula I

2-Methyl-1-(2-methylpropyl)-1H-imidazo[4,5-c][1,7]naphthyridin-4-amine

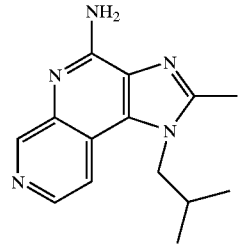

Part A:

Triphenylphosphine (2.5 g, 9.6 mmol) was added to a suspension of 2-methyl-1-(2-methylpropyl)-1H-tetrazolo[1,5-a]imidazo[4,5-c][1,7]naphthyridine (1 g, 4 mmol) in dichlorobenzene. The reaction mixture was heated at reflux overnight then concentrated under vacuum. The residue was slurried with hexane and the resulting solid 2-methyl-1-(2-methylpropyl)-N-triphenylphosphinyl-1H-imidazo[4,5-c][1,7]naphthyridin-4-amine was isolated by filtration.

Part B:

The 2-methyl-1-(2-methylpropyl)-N-triphenylphosphinyl-1H-imidazo[4,5-c][1,7]naphthyridin-4-amine from Part A was dissolved in methanol (100 mL). Hydrochloric acid (10 mL of 3N) was added to the solution and the reaction mixture was heated at reflux overnight before being concentrated under vacuum to remove the methanol. The residue was purified by flash chromatography (silica gel eluting with dichloromethane and gradually increasing the polarity to 5% methanol in dichloromethane) to provide 2-methyl-1-(2-methylpropyl)-1H-imidazo[4,5-c][1,7]naphthyridin-4-amine as a solid, m.p. 322–324° C. Analysis: Calculated for $C_{14}H_{17}N_5$: %C, 65.86; %H, 6.71; %N, 27.43; Found: %C, 65.81; %H, 6.64; %N, 27.41.

EXAMPLE 26

Compound of Formula II 6,7,8,9-Tetrahydro-2-methyl-1-(2-methylpropyl)-1H-imidazo[4,5-c][1,7]naphthyridin-4-amine

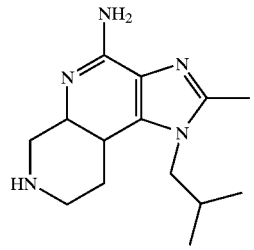

A catalytic amount of platinum oxide was added to a solution of 2-methyl-1-(2-methylpropyl)-1H-imidazo[4,5-c][1,7]naphthyridin-4-amine (0.1 g, 0.4 mol) in trifluoroacetic acid. The reaction mixture was reduced on a Parr apparatus at 50 psi (3.5 Kg/cm$^2$) hydrogen pressure overnight. The reaction mixture was filtered and washed with methanol to remove the catalyst, and the filtrate was concentrated under vacuum. The residue was combined with dichloromethane and aqueous sodium bicarbonate was added until the mixture was basic. The dichloromethane layer was separated, and the aqueous layer was extracted three times with dichloromethane (100 mL). The combined dichloromethane extracts were dried over magnesium sulfate and concentrated under vacuum. The resulting residue was recrystallized from toluene to provide 6,7,8,9-tetrahydro-2-methyl-1-(2-methylpropyl)-1H-imidazo[4,5-c][1,7]naphthyridin-4-amine as a solid, m.p. 226–230° C. Analysis: Calculated for $C_{14}H_{21}N_5 + 1.75 H_2O$: %C, 57.81; %H, 8.49; %N, 24.07; Found: %C, 57.89; %H, 8.04; %N, 23.45.

EXAMPLE 27

Compound of Formula I

2-Butyl-1-(2-methylpropyl)-1H-imidazo[4,5-c][1,7]naphthyridin-4-amine

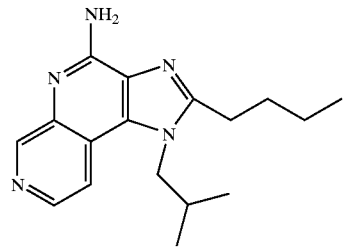

Part A:

Valeryl chloride (0.76 mL, 6.4 mmol) was added to a solution of $N^5$-(2-methylpropyl)tetrazolo[1,5-a][1,7]naphthyridin-4,5-diamine (1.5 g, 5.8 mmol) in acetonitrile (15 mL). The reaction mixture was allowed to stir at ambient temperature for several hours. The resulting precipitate was isolated by filtration. Thin layer chromatography indicated that the material contained two components. The solid was dissolved in acetic acid and heated at reflux overnight. The reaction mixture was concentrated under vacuum, and the residue extracted with dichloromethane. The dichloromethane extract was washed with water, dried over magnesium sulfate and concentrated under vacuum to provide a mixture of 2-butyl-1-(2-methylpropyl)-1H-tetrazolo[1,5-a]imidazo[4,5-c][1,7]naphthyridine and the acylated, but uncyclized intermediate.

Part B:

Triphenylphosphine (2.4 g) was added to a suspension of the material from Part A in dichlorobenzene. The reaction mixture was heated at reflux overnight then concentrated under vacuum. The residue was slurried with hexane and the resulting solid 2-butyl-1-(2-methylpropyl)-N-triphenylphosphinyl-1H-imidazo[4,5-c][1,7]naphthyridin-4-amine was isolated by filtration.

Part C:

The 2-butyl-1-(2-methylpropyl)-N-triphenylphosphinyl-1H-imidazo[4,5-c][1,7]naphthyridin-4-amine from Part B was dissolved in methanol. Hydrochloric acid (3N) was added to the solution and the reaction mixture was heated at reflux overnight before being concentrated under vacuum to remove the methanol. The aqueous residue was mixed with dichloromethane then neutralized with aqueous sodium bicarbonate. The dichloromethane layer was separated, dried over magnesium sulfate and concentrated under vacuum. The residue was purified by flash chromatography (silica gel eluting with dichloromethane and gradually increasing the polarity to 5% methanol in dichloromethane) to provide 2-butyl-1-(2-methylpropyl)-1H-imidazo[4,5-c][1,7]

naphthyridin-4-amine as a solid, m.p 213–214° C. Analysis: Calculated for $C_{17}H_{23}N_5$: %C, 68.66; %H, 7.80; %N, 23.55; Found: %C, 68.26; %H, 7.69; %N, 23.41.

EXAMPLE 28

Compound of Formula II

2-Butyl-6,7,8,9-tetrahydro-1-(2-methylpropyl)-1H-imidazo[4,5-c][1,7]naphthyridin-4-amine

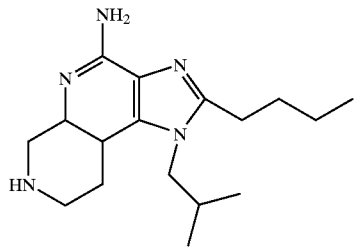

A catalytic amount of platinum oxide was added to a solution of 2-butyl-1-(2-methylpropyl)-1H-imidazo[4,5-c][1,7]naphthyridin-4-amine (0.5 g, 1.68 mol)) in trifluoroacetic acid (20 mL). The reaction mixture was reduced on a Parr apparatus at 50 psi (3.5 Kg/cm²) hydrogen pressure overnight. The reaction mixture was filtered and washed with methanol to remove the catalyst. The filtrate was concentrated under vacuum. The residue was combined with dichloromethane and aqueous sodium bicarbonate was added until the mixture was basic. The dichloromethane layer was separated. The aqueous layer was extracted three times with dichloromethane (100 mL). The dichloromethane extracts were combined, dried over magnesium sulfate and concentrated under vacuum. The resulting residue was recrystallized from toluene then purified by flash chromatography (silica gel eluting with 20% methanol in dichloromethane with a trace of ammonium hydroxide) to provide 6,7,8,9-tetrahydro-2-butyl-1-(2-methylpropyl)-1H-imidazo [4,5-c][1,7]naphthyridin-4-amine as a solid, m.p. 164–166° C. Analysis: Calculated for $C_{17}H_{27}N_5+0.5\ H_2O$: %C, 65.77; %H, 9.09; %N, 22.56; Found: %C, 65.99; %H, 8.71; %N, 22.23.

EXAMPLE 29

Compound of Formula XXXI $N^4$-(2-Methylpropyl)-3-nitro[1,5]naphthyridin-4-amine Phosphorous oxychloride (0.6 mL, 6.44 mmol) was reacted with N,N-dimethylformamide then added to a solution of 3-nitro[1,5]naphthyridin-4-ol (1.0 g, 5.23 mmol) in N,N-dimethylformamide (20 mL). The reaction mixture was warmed using a jacketed flask with refluxing acetone as a heat source. After 3 hours the reaction mixture was poured into ice water, isobutylamine (2.0 mL, 20.1 mmol) was added and the mixture was heated on a steam bath. After several hours the reaction mixture was cooled to ambient temperature, filtered and washed with water. The aqueous layer was extracted with dichloromethane. The dichloromethane extract was washed with aqueous sodium bicarbonate, washed with water, dried over magnesium filtrate then loaded onto a layer of silica gel. The silica gel was eluted initially with dichloromethane to remove an impurity then with 5% methanol in dichloromethane to recover the product. The eluant was concentrated to dryness to provide $N^4$-(2-methylpropyl)-3-nitro[1,5]naphthyridin-4-amine as a solid, m.p. 97–99° C.

EXAMPLE 30

Compound of Formula XXXIII 1-(2-Methylpropyl)-1H-imidazo[4,5-c][1,5]naphthyridine Part A:

A catalytic amount of 5% platinum on carbon was added to a solution of $N^4$-(2-methylpropyl)-3-nitro[1,5] naphthyridin-4-amine (1.0 g, 4.1 mmol) in ethyl acetate (50 mL). The reaction mixture was reduced on a Parr apparatus at 50 psi (3.5 Kg/cm²) hydrogen for four hours. The reaction mixture was filtered to remove the catalyst and the filtrate was concentrated under vacuum to provide $N^4$-(2-methylpropyl)[1,5]naphthyridin-3,4-diamine as a crude solid.

Part B:

The crude solid from Part A was combined with diethoxymethylacetate (2 mL) then heated on a steam bath overnight. The reaction mixture was taken up in dichloromethane, washed with water, dried over magnesium sulfate then filtered through a layer of silica gel. The silica gel was eluted with dichloromethane to remove excess diethoxymethylacetate then with 5% methanol in dichloromethane to recover the product. The eluant was concentrated to provide an oil which was purified by flash chromatography (silica gel eluting with 50% ethyl acetate/hexane then with ethyl acetate) to provide 0.25 g of 1-(2-methylpropyl)-1H-imidazo[4,5-c][1,5]naphthyridine as a solid m.p. 82–84° C. Analysis: Calculated for $C_{13}H_{14}N_4$: %C, 69.00; %H, 6.24; %N, 24.76; Found: %C, 68.79; %H, 6.44; %N, 24.73.

EXAMPLE 31

Compound of Formula XXXIV 1-(2-Methylpropyl)-1H-imidazo[4,5-c][1,5]naphthyridine-5N-oxide 3-Chloroperoxybenzoic acid (3.7 g of 50%) was added in small portions over a period of 30 minutes to a solution of 1-(2-methylpropyl)-1H-imidazo[4,5-c][1,5]naphthyridine (1.5 g) in chloroform at ambient temperature. After 3 hours the reaction mixture was diluted with chloroform, washed twice with 2.0 M sodium hydroxide and once with water, dried over magnesium sulfate then concentrated under vacuum. The residue was recrystallized from ethyl acetate/hexane to provide 1.2 g of 1-(2-methylpropyl)-1H-imidazo [4,5-c][1,5]naphthyridine-5N-oxide as a solid, m.p. 183–185° C. Analysis: Calculated for $C_{13}H_{14}N_4O$: %C, 64.45; %H, 5.82; %N, 23.12; Found: %C, 64.15; %H, 5.92; %N, 23.02.

EXAMPLE 32

Compound of Formula I 1-(2-Methylpropyl)-1H-imidazo[4,5-c][1,5]
naphthyridin-4-amine

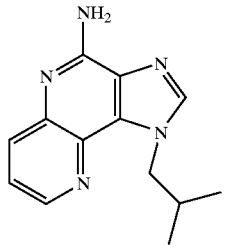

Ammonium hydroxide (10 mL) was added to a solution of 1-(2-methylpropyl)-1H-imidazo [4,5-c][1,5]naphthyridine-5N-oxide (0.6 g) in dichloromethane (30 mL). The reaction mixture was cooled in an ice bath then tosyl chloride (0.5 g) in dichloromethane was added while the reaction was being rapidly stirred. The reaction mixture was stirred at ambient temperature overnight. The dichloromethane layer was separated, washed with aqueous sodium bicarbonate, dried over magnesium sulfate then concentrated under vacuum. The residue was recrystallized from ethyl acetate/hexane to provide 0.2 g of 1-(2-methylpropyl)-1H-imidazo[4,5c][1,5]naphthyridin-4-amine as a solid, m.p. 230–231.5° C. Analysis: Calculated for $C_{13}H_{15}N_5$: %C, 64.71; %H, 6.27; %/N, 29.02; Found: %C, 64.70; %H, 6.01; %N, 29.08.

EXAMPLE 33

Compound of Formula II 6,7,8,9-Tetrahydro-1-(2-methylpropyl)-1H-imidazo
[4,5-c][1,5]naphthyridin-4-amine

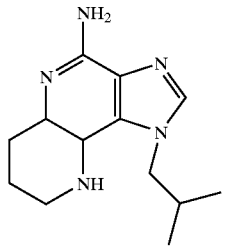

A catalytic amount of platinum oxide was added to a solution of 1-(2-methylpropyl)-1H-imidazo[4,5-c][1,5] naphthyridin-4-amine (0.46 g) in trifluoroacetic acid (10 mL). The reaction mixture was reduced on a Parr apparatus under 45 psi (3.15 Kg/cm²) hydrogen pressure for 4 hours. The reaction mixture was filtered to remove the catalyst and the filtrate was concentrated under vacuum. The residue was combined with aqueous sodium bicarbonate then a small amount of 10% sodium hydroxide was added. The resulting precipitate was extracted with dichloromethane. The dichloromethane extract was dried over magnesium sulfate then concentrated under vacuum. The residue was purified by flash chromatography (silica gel eluting with 5% methanol in dichloromethane containing 0.5% ammonium hydroxide). The eluant was concentrated under vacuum. The residue was recrystallized from ethyl acetate to provide 6,7,8,9-tetrahydro-1-(2-methylpropyl)-1H-imidazo[4,5-c][1,5] naphthyridin-4-amine as a solid, m.p. 222–226° C. Analysis: Calculated for $C_{13}H_{19}N_5$: %C, 63.65; %H, 7.81; %N, 28.55; Found: %C, 63.07; %H, 7.51; %N, 28.00.

EXAMPLE 34

Compound of Formula XXXIII

2-Methyl-1-(2-methylpropyl)-1H-imidazo[4,5-c][1,
5]naphthyridine

Part A:

Magnesium sulfate (3 g) and a catalytic amount of 5% platinum on carbon were added to a solution of $N^4$-(2-methylpropyl)-3-nitro[1,5]naphthyridin-4-amine(4.0 g, 16.2 mmol) in ethyl acetate (250 mL). The reaction mixture was reduced on a Parr apparatus at 50 psi (3.5 Kg/cm²) hydrogen for four hours. The reaction mixture was filtered to remove the catalyst and the filtrate was concentrated under vacuum to provide $N^4$-(2-methylpropyl)[1,5]naphthyridin-3,4-diamine as a crude solid.

Part B:

The rude solid from Part A was taken up in acetic acid, combined with acetic anhydride then heated at reflux overnight. The reaction mixture was concentrated under vacuum. The resulting residue was combined with methanol to decompose excess acetic anhydride then concentrated under vacuum. The resulting residue was combined with cyclohexane then concentrated under vacuum to remove the acetic acid. The resulting residue was recrystallized from hexanes to provide 2.2 g of 2-methyl-1-(2-methylpropyl)-1H-imidazo[4,5c][1,5]naphthyridine as off-white needles, m.p. 118–119° C. Analysis: Calculated for $C_{14}H_{16}N_4$: %C, 69.97; %H, 6.71; %N, 23.31; Found: %C, 69.24; %H, 6.67; %N, 23.23.

EXAMPLE 35

Compound of Formula XXXIV

2-Methyl-1-(2-methylpropyl)-1H-imidazo[4,5-c][1,
5]naphthyridine-5N-oxide

3-Chloroperoxybenzoic acid (4.5 g of 50%, 13.1 mmol) was added i n small portions over a period of 30 minutes to a solution of 2-methyl-1-(2-methylpropyl)-1H-imidazo[4,5-c][1,5]naphthyridine (2.1 g, 8.7 mmole) in chloroform at ambient temperature. After 3 hours the reaction mixture was diluted with chloroform, washed twice with 2.0 M sodium hydroxide, once with water, and once with brine, dried over magnesium sulfate then concentrated under vacuum. The residue was purified by flash chromatography (silica gel eluting with 5% methanol in dichloromethane) to provide 2-methyl-1-(2-methylpropyl)-1H-imidazo[4,5-c][1,5] naphthyridine-5N-oxide as a solid, m.p. 228–230° C. Analysis: Calculated for $C_{14}H_{16}N_4O$: %C, 65.61; %H, 6.29; %N, 21.86; Found: %C, 65.73; %H, 6.31; %N, 21.95.

EXAMPLE 36

Compound of Formula I

2-Methyl-1-(2-methylpropyl)-1H-imidazo[4,5-c][1,5]naphthyridin-4-amine

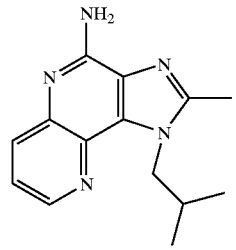

Ammonium hydroxide (10 mL) was added to a solution of 2-methyl-1-(2-methylpropyl)-1H-imidazo[4,5-c][1,5]naphthyridine-5N-oxide (1.1 g, 4.29 mmol) in dichloromethane (50 mL). The reaction mixture was cooled in an ice bath then tosyl chloride (0.82 g, 4.29 mmol) in dichloromethane was added. The reaction was warmed to about 30° C. while being rapidly stirred. The reaction mixture was stirred at ambient temperature overnight. The dichloromethane layer was separated, washed with 10% sodium hydroxide, water and brine, dried over magnesium sulfate then concentrated under vacuum. The residue was recrystallized from ethyl acetate to provide 0.8 g of 2-methyl-1-(2-methylpropyl)-1H-imidazo[4,5-c][1,5]naphthyridin-4-amine as a solid, m.p. 228–230° C. Analysis: Calculated for $C_{14}H_{17}N_5$: %C, 65.86; %H, 6.71; %N, 27.43; Found: %C, 65.65; %H, 6.69; %N, 27.59.

EXAMPLE 37

Compound of Formula XXXIII

2-Butyl-1-(2-methylpropyl)-1H-imidazo[4,5-c][1,5]naphthyridine

Part A:

Magnesium sulfate (3 g) and a catalytic amount of 5% platinum on carbon were added to a solution of $N^4$-(2-methylpropyl)-3-nitro[1,5]naphthyridin-4-amine (3.0 g, 12.2 mmol) in ethyl acetate (150 mL). The reaction mixture was reduced on a Parr apparatus at 50 psi (3.5 Kg/cm²) hydrogen for four hours. The reaction mixture was filtered to remove the catalyst and the filtrate was concentrated under vacuum to provide $N^4$-(2-methylpropyl)[1,5]naphthyridin-3,4-diamine as a crude solid.

Part B:

The crude solid from Part A was taken up in acetonitrile then combined with valeryl chloride (1.5 mL, 12.2 mmol). The mixture was stirred at ambient temperature for 30 minutes. The resulting precipitate was isolated by filtration, washed with a small amount of acetonitrile and air dried to provide 2.75 g of N-(4-(2-methylpropylamino)[1,5]naphthyridin-3-yl)valeramide hydrochloride as a solid.

Part C:

The solid from Part B was suspended in acetic acid and heated at reflux overnight. The reaction mixture was concentrated under vacuum and the resulting residue was partitioned between dichloromethane and aqueous sodium bicarbonate. The dichloromethane layer was separated, dried over magnesium sulfate and concentrated under vacuum to provide 2.3 g of 2-butyl-1-(2-methylpropyl)-1H-imidazo[4,5-c][1,5]naphthyridine as an oil.

EXAMPLE 38

Compound of Formula XXXIV

2-Butyl-1-(2-methylpropyl)-1H-imidazo[4,5-c][1,5]naphthyridine-5N-oxide

3-Chloroperoxybenzoic acid (5.3 g of 50%, 15.2 mmol) was added in small portions over a period of 30 minutes to a solution of 2-butyl-1-(2-methylpropyl)-1H-imidazo[4,5-c][1,5]naphthyridine (2.3 g, 10.2 mmole) in chloroform at ambient temperature. After 3 hours the reaction mixture was diluted with chloroform, washed twice with 2.0 M sodium hydroxide, once with water, and once with brine, dried over magnesium sulfate then concentrated under vacuum. The residue was purified by flash chromatography (silica gel eluting with 5% methanol in dichloromethane) to provide 2-butyl-1-(2-methylpropyl)-1H-imidazo[4,5-c][1,5]naphthyridine-5N-oxide. Analysis: Calculated for $C_{17}H_{22}N_4O$: %C, 68.43; %H, 7.43; %N, 18.78; Found: %C, 67.67; %H, 6.73; %N, 18.13

EXAMPLE 39

Compound of Formula I

2-Butyl-1-(2-methylpropyl)-1H-imidazo[4,5-c][1,5]naphthyridin-4-amine

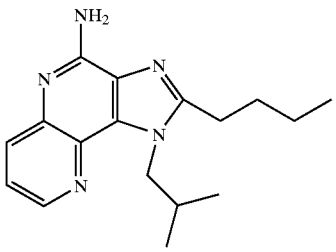

Ammonium hydroxide (25 mL) was added to a solution of 2-butyl-1-(2-methylpropyl)-1H-imidazo[4,5-c][1,5]naphthyridine-5N-oxide (2.0 g, 6.7 mmol) in dichloromethane (100 mL). The reaction mixture was cooled in an ice bath then tosyl chloride (1.3 g, 6.7 mmol) in dichloromethane was added. The reaction was warmed to about 30° C. while being rapidly stirred. The reaction mixture was stirred at ambient temperature overnight. The dichloromethane layer was separated, washed with 10% sodium hydroxide, water and brine, dried over magnesium sulfate then concentrated under vacuum. The residue was recrystallized from hexane to provide 1.55 g of 2-butyl-1-(2-methylpropyl)-1H-imidazo[4,5-c][1,5]naphthyridin-4-amine as a solid, m.p. 115–116° C. Analysis: Calculated for $C_{17}H_{23}N_5$: %C, 68.66; %H, 7.80; %N, 23.55; Found: %C, 69.52; %H, 7.72; %N, 21.72

EXAMPLE 40

Compound of Formula II 6,7,8,9-Tetrahydro-2-butyl-1-(2-methylpropyl)-1H-imidazo[4,5-c][1,5]naphthyridin-4-amine

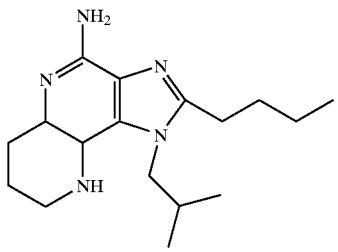

A catalytic amount of platinum oxide was added to a solution of 2-butyl-1-(2-methylpropyl)-1H-imidazo[4,5-c][1,5]naphthyridin-4-amine (0.5 g) in trifluoroacetic acid (15 mL). The reaction mixture was reduced on a Parr apparatus under 50 psi (3.5 Kg/cm$^2$) hydrogen pressure overnight. The reaction mixture was filtered to remove the catalyst and the filtrate was concentrated under vacuum. The residue was combined with aqueous sodium bicarbonate then a small amount of 10% sodium hydroxide was added. The resulting precipitate was extracted with dichloromethane. The dichloromethane extract was dried over magnesium sulfate then concentrated under vacuum. The residue was purified by flash chromatography (silica gel eluting with 1–5% methanol in dichloromethane containing 0.5% ammonium hydroxide). The eluant was concentrated under vacuum. The residue was recrystallized from hexane/ethyl acetate to provide 6,7,8,9-tetrahydro-2-butyl-1-(2-methylpropyl)-1H-imidazo[4,5-c][1,5]naphthyridin-4-amine as a solid, m.p. 143–147° C. Analysis: Calculated for $C_{17}H_{27}N_5$: %C, 67.74; %H, 9.03; %N, 23.23; Found: %C, 61.90; %H, 7.51; %N, 19.91.

EXAMPLE 41

Compound of Formula XXXI 1,1-Dimethylethyl N-{4-[(3-Nitro[1,5]naphthyridin-4-yl)amino]butyl}carbamate Phosphorus oxychloride (4 mL, 0.31 mole) was combined with N,N-dimethylformamide (100 mL) while cooling in an ice bath. The resulting mixture was added to a solution of 3-nitro[1,5]naphthyridin-4-ol (50 g, 0.26 mole) in N,N-dimethylformamide (500 mL). The reaction mixture was stirred at ambient temperature for 6 hours. The reaction mixture was poured into ice water and then extracted with dichloromethane (1800 mL). The organic layer was separated and then combined with triethylamine (45 mL). Tert-butyl N-(4-aminobutyl)carbamate was added and the reaction mixture was stirred overnight. The reaction mixture was concentrated under vacuum and the residue was treated with water (~1500 mL). The resulting solid was isolated by filtration, washed with water and dried to provide 76 g of 1,1-dimethylethyl N-{4-[(3-nitro[1,5]naphthyridin-4-yl)amino]butyl}carbamate as a solid. A small sample was recrystallized from isopropyl alcohol to provide a pure sample, m.p. 137–138° C. Analysis: Calculated for $C_{17}H_{23}N_5O_4$: %C, 56.50; %H, 6.41; %N, 19.38; Found: %C, 56.26; %H, 6.30; %N, 19.53.

EXAMPLE 42

Compound of Formula XXXII 1,1-Dimethylethyl N-{4-[(3-Amino[1,5]naphthyridin-4-yl)amino]butyl}carbamate 1,1-Dimethylethyl N-{4-[(3-nitro[1,5]naphthyridin-4-yl)amino]butyl}carbamate (42.7 g, 0.12 mole), platinum on carbon (2 g) and ethyl acetate (500 mL) were combined and then hydrogenated on a Parr apparatus at 30 psi (2.1 Kg/cm$^2$) hydrogen pressure for 1 hour. The catalyst was removed by filtration and rinsed with ethyl acetate. The filtrate was concentrated under vacuum to provide 1,1-dimethylethyl N-{4-[(3-amino[1,5]naphthyridin-4-yl)amino]butyl}carbamate as a bright yellow-orange solid.

EXAMPLE 43

Compound of Formula XXXIII 1,1-Dimethylethyl N-[4-(2-Butyl-1H-imidazo[4,5-c][1,5]naphthyridin-1-yl)butyl]carbamate Freshly distilled trimethyl orthovalerate (41 mL, 0.24 mole) was added to a mixture of 1,1-dimethylethyl N-{4-[(3-amino[1,5]naphthyridin-4-yl)amino]butyl}carbamate (39 g, 0.12 mole) in warm xylene (500 mL). The reaction mixture was heated at reflux overnight. Thin layer chromatography showed that at least half of the starting material was still present. p-Toluenesulfonic anhydride monohydrate (6 g) was added. After a short time thin layer chromatography showed that the reaction was complete. The reaction mixture was allowed to cool to ambient temperature and then it was diluted with ethyl acetate and washed with aqueous sodium bicarbonate. The organic layer was concentrated under vacuum to provide an oily residue. The residue was triturated with hexane to provide a dark pink solid. This solid was recrystallized from acetonitrile to provide 1,1-dimethylethyl N-[4-(2-butyl-1H-imidazo[4,5-c][1,5]naphthyridin-1-yl)butyl]carbamate as a pale peach solid, m.p. 96.0–98.0° C. Analysis: Calculated for $C_{22}H_{31}N_5O_2$: %C, 66.47; %H, 7.86; %N, 17.62; Found: %C, 66.29; %H, 7.78; %N, 17.76.

EXAMPLE 44

Compound of Formula XXXIV

1-{4-[(1,1-Dimethylethylcarbonyl)amino]butyl}-2-butyl-1H-imidazo[4,5-c][1,5]naphthyridine-5N-oxide 3-Chloroperbenzoic acid (1 eq at 57%) was added in portions to a solution of 1,1-dimethylethyl N-[4-(2-butyl-1H-imidazo[4,5-c][1,5]naphthyridin-1-yl)butyl]carbamate in chloroform (50 mL). The reaction mixture was allowed to stir at ambient temperature for 2 hours at which time thin layer chromatography showed that no starting material remained. The reaction mixture was diluted with dichloromethane and then washed twice with 1M sodium hydroxide. The organic layer was dried over anhydrous magnesium sulfate and then concentrated under vacuum to provide 1-{4-[(1,1-dimethylethylcarbonyl)amino]butyl}-2-butyl-1H-imidazo[4,5-c][1,5]naphthyridine-5N-oxide as an orange oil which solidified on standing.

EXAMPLE 45

Compound of Formula I 1,1-Dimethylethyl N-[4-(4-Amino-2-butyl-1H-imidazo[4,5-c][1,5]naphthyridin-1-yl)butyl]carbamate

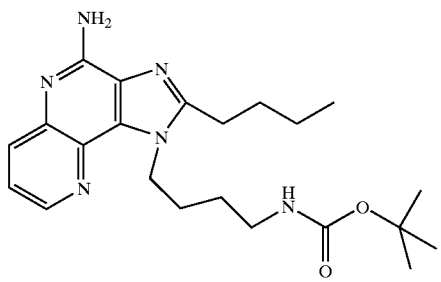

Anmmonium hydroxide (20 mL) was added to a solution of 1-{4-[(1,1-dimethylethylcarbonyl)amino]butyl}-2-butyl-1H-imidazo[4,5-c][1,5]naphthyridine-5N-oxide (19.4 g) in chloroform. Tosyl chloride (9 g) was slowly added. Thin layer chromatography indicated that the reaction was proceeding slowly. Additional tosyl chloride was added twice. After thin layer chromatography indicated that the reaction was complete, the layers were separated. The organic layer was washed with dilute aqueous sodium carbonate, dried over magnesium sulfate and then concentrated under vacuum. The residue was covered with methyl acetate (10 mL), hexane (5 mL) was added and the mixture was allowed to stand overnight. The resulting crystalline solid was isolated by filtration, washed with hexane and then dried to provide 15.1 g of 1,1-dimethylethyl N-[4-(4-amino-2-butyl-1H-imidazo[4,5-c][1,5]naphthyridin-1-yl)butyl]carbamate, m.p. 148.5–149.5° C. Analysis: Calculated for $C_{22}H_{32}N_6O_2$: %C, 64.05; %H, 7.82; %N, 20.37; Found: %C, 64.15; %H, 7.82; %N, 20.55.

EXAMPLE 46

Compound of Formula I 4-(4-Amino-2-butyl-1H-imidazo[4,5-c][1,5]naphthyridin-1-yl)butaneamine

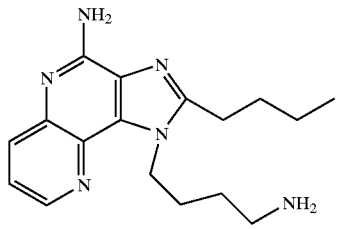

A suspension of 1,1-dimethylethyl N-[4-(4-amino-2-butyl-1H-imidazo[4,5-c][1,5]naphthyridin-1-yl)butyl]carbamate (13.8 g) in 1N hydrochloric acid (140 mL) was heated on a steam bath for 1.5 hours. The reaction mixture was allowed to cool to ambient temperature and then it was made basic (pH>11) with 50% sodium hydroxide. The resulting precipitate was isolated by filtration, washed with water and then dried to provide 9.5 g of 4-(4-amino-2-butyl-1H-imidazo[4,5-c][1,5]naphthyridin-1-yl)butaneamine as a white solid, m.p. 212–213° C. Analysis: Calculated for $C_{17}H_{24}N_6$: %C, 65.36; %H, 7.74; %N, 26.90; Found: %C, 65.16; %H, 7.65; %N, 27.29.

EXAMPLE 47

Compound of Formula I

N-[4-(4-Amino-2-butyl-1H-imidazo[4,5-c][1,5]naphthyridin-1-yl)butyl]-N'-phenylurea

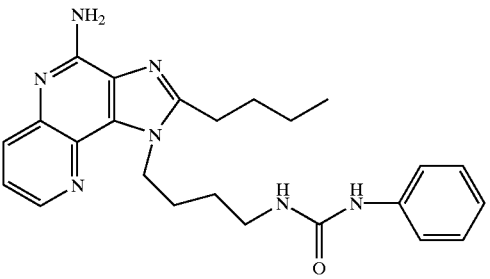

Under a nitrogen atmosphere, phenyl isocyanate (52 μL, 0.48 mmol) was added to a suspension of 4-(4-amino-2-butyl-1H-imidazo[4,5-c][1,5]naphthyridin-1-yl)butaneamine (0.15 g, 0.48 mmole) in anhydrous tetrahydrofuran (60 mL). The reaction mixture was stirred for 20 minutes at which time it had turned homogeneous and thin layer chromatography indicated no starting material remained. Aminomethyl resin (280 mg of 1% cross linked, 100–200 mesh available from BACHEM, Torrance, Calif.) was added and the reaction mixture was allowed to stir for 0.5 hr. Silica gel (0.4 g) was added and the mixture was concentrated under vacuum to provide a solid. The solid was purified by flash chromatography eluting with 95/5 dichloromethane/methanol to give a white solid which was dried under vacuum at 60° C. to provide 0.12 g of N-[4-(4-amino-2-butyl-1H-imidazo[4,5-c][1,5]naphthyridin-1-yl)butyl]-N'-phenylurea. Analysis: Calculated for $C_{24}H_{29}N_7O + \frac{1}{8}H_2O$: %C, 66.25; %H, 6.81; %N, 22.53; Found: %C, 66.27; %H, 6.63; %N, 22.83

EXAMPLE 48

Compound of Formula I

N-[4-(4-Amino-2-butyl-1H-imidazo[4,5-c][1,5]naphthyridin-1-yl)butyl]-N'-cyclohexylurea

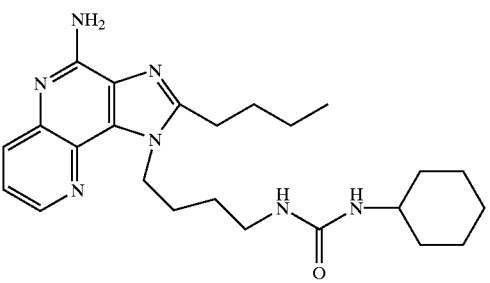

Using the general method of Example 47, cyclohexyl isocyanate (61 μL, 0.48 mmol) was reacted with 4-(4-amino-2-butyl-1H-imidazo[4,5-c][1,5]naphthyridin-1-yl)butaneamine (0.15 g, 0.48 mmole) to provide 0.14 g of N-[4-(4-amino-2-butyl-1H-imidazo[4,5-c][1,5]naphthyridin-1-yl)butyl]-N'-cyclohexylurea as a white solid.

Analysis: Calculated for $C_{24}H_{35}N_7O$: %C, 65.88; %H, 8.06; %N, 22.41. $^1$H NMR (300 MHz, CDCl$_3$) δ 8.60 (dd, J=4.4, 1.4 Hz, 1H), 8.08 (d, J=8.5 Hz, 1H), 7.44 (dd, J=4.4 Hz, 1H), 5.55 (br s, 2H), 4.92 (t, J=5.8 Hz, 1H), 4.82 (apparent t, J=7.8 Hz, 4.13 (d, J=8.6 Hz, 1H), 3.48 (m, 1H), 3.35 (apparent q, J=6.4 Hz, 2H), 2.93 t, J=7.8 Hz, 2H), 1.80–2.05 (m, 4H), 1.45–1.75 (m, 6H), 1.2–1.4 (m 2H), 1.03 (t, 7.4 Hz, 3H); HRMS (EI) calcd for $C_{24}H_{35}N_7O$ (M$^+$) 437.2903, found 437.2903.

EXAMPLE 49

Compound of Formula I

N-[4-(4-Amino-2-butyl-1H-imidazo[4,5-c][1,5]naphthyridin-1-yl)butyl[-N'-butylurea

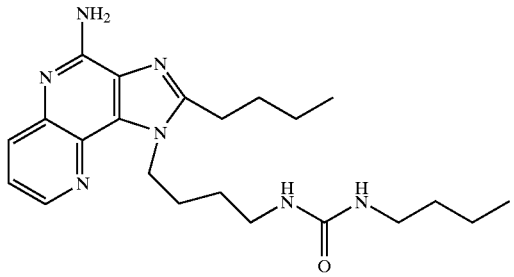

Using the general method of Example 47, butyl isocyanate (54 μL, 0.48 mmol) was reacted with 4-(4-amino-2-butyl-1H-imidazo[4,5-c][1,5]naphthyridin-1-yl)butaneamine (0.15 g, 0.48 mmole) to provide 0.13 g of N-[4-(4-amino-2-butyl-1H-imidazo[4,5-c][1,5]naphthyridin-1-yl)butyl]-N'-butylurea as a white solid. Analysis: Calculated for $C_{22}H_{33}N_7O$: %C, 64.21; %H, 8.08; %N, 23.82; Found: %C, 64.05; %H, 7.97; %N, 24.00.

EXAMPLE 50

Compound of Formula I

Phenyl N-[4-(4-Amino-2-butyl-1H-imidazo[4,5-c][1,5]naphthyridin-1-yl)butyl]carbamate

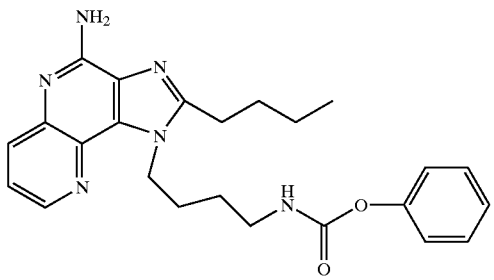

Using the general method of Example 47, phenyl chloroformate (61 μL, 0.48 mmol) was reacted with 4-(4-amino-2-butyl-1H-imidazo[4,5-c][1,5]naphthyridin-1-yl) butaneamine (0.15 g, 0.48 mmole) to provide 0.12 g of phenyl N-[4-(4-amino-2-butyl-1H-imidazo[4,5-c][1,5]naphthyridin-1-yl)butyl]carbamate as a solid. Analysis: Calculated for $C_{24}H_{28}N_6O_2$: %C, 66.65; %H, 6.53; %N, 19.43; Found: %C, 66.49; %H, 6.59; %N, 19.32.

EXAMPLE 51

Compound of Formula I

N-[4-(4-Amino-2-butyl-1H-imidazo[4,5-c][1,5]naphthyridin-1-yl)butyl]-2-furamide

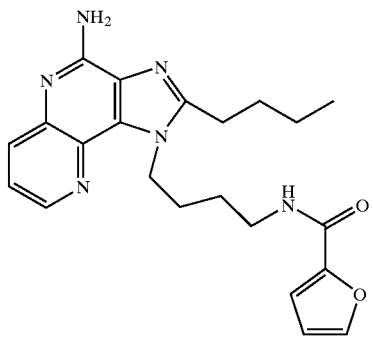

Using the general method of Example 47, furoyl chloride (15.8 μL, 0.16 mmol) was reacted with 4-(4-amino-2-butyl-1H-imidazo[4,5-c][1,5]naphthyridin-1-yl)butaneamine (0.05 g, 0.16 mmole) to provide 0.019 g of N-[4-(4-amino-2-butyl-1H-imidazo[4,5-c][1,5]naphthyridin-1-yl)butyl]-2-furamide as a white solid. $^1$H NMR (300 MHz, CDCl$_3$) δ 8.58 (dd, J=4.4, 1.5 Hz, 1H), 8.06 (dd, J=8.6, 1.6 Hz, 1H), 7.41 (dd, J=8.5, 4.4 Hz, 1H), 7.33 (m, 1H), 7.08 (dd, J=3.5, 0.6 Hz, 1H), 6.84 (m, 1H), 6.47 (dd, J=3.5, 1.7 Hz, 1H), 4.86 (apparent t, J=7.7 Hz, 2H), 3.59 (apparent q, J=6.5 Hz, 2H), 2.92 (apparent t, J=7.8 Hz, 2H), 1.7–2.1(m, 6H), 1.51 (m, 2H); 1.00 (t, J=7.3 Hz, 3H); HRMS (EI) calcd for $C_{22}H_{26}N_6O_2$ (M$^+$) 406.2117, found 406.2121.

EXAMPLE 52

Compound of Formula I

N-[4-(4-Amino-2-butyl-1H-imidazo[4,5-c][1,5]naphthyridin-1-yl)butyl]benzamide

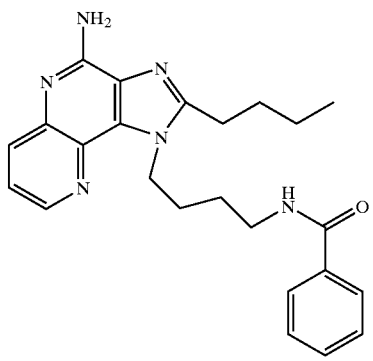

Using the general method of Example 47, benzoyl chloride (56 μL, 0.48 mmol) was reacted with 4-(4-amino-2-butyl-1H-imidazo[4,5-c][1,5]naphthyridin-1-yl) butaneamine (0.15 g, 0.48 mmole) to provide 0.11 g of N-[4-(4-amino-2-butyl-1H-imidazo[4,5-c][1,5]naphthyridin-1-yl)butyl]benzamide as a white solid. Analysis: Calculated for $C_{24}H_{28}N_6O+\frac{1}{4}H_2O$: %C, 68.47; %H, 6.82; %N, 19.96: Found: %C, 68.24; %H, 6.76; %N, 19.90.

EXAMPLE 53

Compound of Formula I

N-[4-(4-Amino-2-butyl-1H-imidazo[4,5-c][1,5]
naphthyridin-1-yl)butyl]-N'-benzylurea

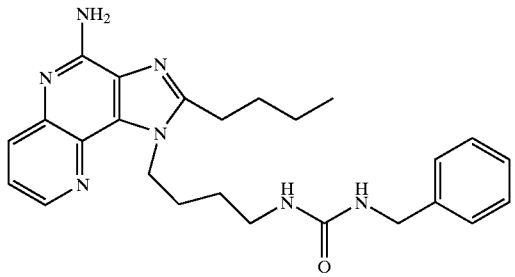

Benzyl isocyanate (59 μL, 0.48 mmol) was added at ambient temperature to a suspension of 4-(4-amino-2-butyl-1H-imidazo[4,5-c][1,5]naphthyridin-1-yl)butaneamine (0.15 g, 0.48 mmol) in tetrahydrofuran (60 mL). A solution was obtained in less than 30 minutes and thin layer chromatography (9:1 dichloromethane:methanol) showed one major new spot with a higher $R_f$ and only a trace of starting material. Aminomethyl resin (280 mg) was added and the reaction mixture was stirred for 15 minutes. The solvent was removed under vacuum. The residue was purified by column chromatography to provide 0.16 g of N-[4-(4-amino-2-butyl-1H-imidazo[4,5-c][1,5]naphthyridin-1-yl)butyl]-N'-benzylurea as a white solid. Analysis: Calculated for $C_{25}H_{31}N_7O$: %C, 67.39; %H, 7.01; %N, 22.00; Found: %C, 67.43; %H, 6.92; %N, 22.02.

EXAMPLE 54

Compound of Formula I $N^3$-[4-(4-Amino-2-butyl-1H-imidazo[4,5-c][1,5]
naphthyridin-1-yl)butyl]nicotinamide

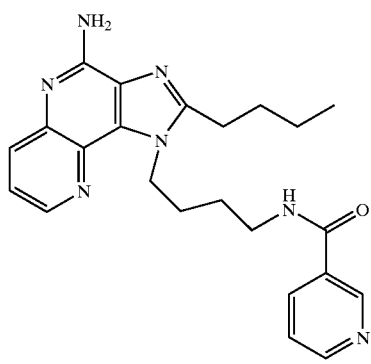

4-(4-Amino-2-butyl-1H-imidazo[4,5-c][1,5]naphthyridin-1-yl)butaneamine (0.050 g, 0.16 mmol) was suspended in tetrahydrofuran (30 mL). N,N-diisopropylethylamine (28 μL, 0.16 mmol) was added to the suspension and then nicotinoyl chloride hydrochloride (0.028 g, 0.16 mmol) was added. The reaction mixture was stirred at ambient temperature for 1 hour by which time a solution was obtained. Thin layer chromatography (9:1 dichloromethane:methanol) showed one major new spot with a higher $R_f$ and only a trace of starting material. Aminomethyl resin (100 mg) was added and the reaction mixture was stirred for 5 minutes. The solvent was removed under vacuum. The residue was dissolved in dichloromethane and placed on a layer of silica gel. The silica gel was eluted first with dichloromethane and then with 9:1 dichloromethane:methanol. The cleanest fractions were combined and then concentrated under vacuum to provide $N^3$-[4-(4-amino-2-butyl-1H-imidazo[4,5-c][1,5]naphthyridin-1-yl)butyl]nicotinamide as a white powder. $^1$H NMR (300 MHz, CDCl$_3$) δ 8.91 (m, 1H), 8.68 (d, J=4.5 Hz, 1H), 8.45 (d, J=4.3 Hz, 1H), 8.03 (m, 2H), 7.30–7.40 (m, 2H), 6.98 (s, 2H), 5.51 (s, 1H), 4.86 (apparent t, J=2H), 3.66 (q, J=6.5 Hz, 2H), 2.92 (apparent t, J=7.7 Hz, 2H), 2.05 (m, 2H), 1.75–1.95 (m, 4H), 1.51 (m, 2H), 1.00 (t, J=7.3 Hz, 3H); HRMS (EI) calcd for $C_{23}H_{27}N_7O$ (m$^+$) 417.2277, found 417.2276.

EXAMPLE 55

Compound of Formula I

N-[4-(4-Amino-2-butyl-1H-imidazo[4,5-c][1,5]
naphthyridin-1-yl)butyl]phenylaceatamide

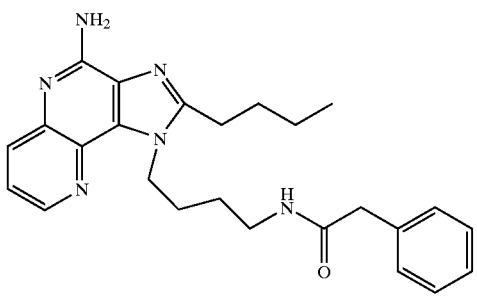

Phenylacetyl chloride (21 μL, 0.16 mmol) was added to a suspension of 4-(4-amino-2-butyl-1H-imidazo[4,5-c][1,5]naphthyridin-1-yl)butaneamine (0.050 g, 0.16 mmol) in tetrahydrofuran (30 mL). The reaction mixture was stirred at ambient temperature for 1 hour by which time a solution was obtained. Thin layer chromatography (9:1 dichloromethane:methanol) showed one major new spot with a higher $R_f$ and only a trace of starting material. Aminomethyl resin (100 mg) was added and the reaction mixture was stirred for 5 minutes. The solvent was removed under vacuum to provide a white powder. This material was placed on a short column of silica gel and purified by eluting first with dichloromethane and then with 9:1 dichloromethane:methanol. The cleanest fractions were combined and then concentrated under vacuum to provide a colorless oil. The oil was dissolved in dichloromethane, hexane was added just until the solution started to become cloudy, and then the solvent was removed to provide N-[4-(4-amino-2-butyl-1H-imidazo[4,5-c][1,5]naphthyridin-1-yl)butyl] phenylacetamide as a white powder. Analysis: Calculated for $C_{25}H_{30}N_6O_2$: %C, 67.24; %H, 6.77; %N, 18.82; Found: %C, 67.52; %H, 6.85; %N, 18.38. $^1$H NMR (300 MHz, CDCl$_3$) δ 8.51 (dd, J=4.4, 1.5 Hz, 1H), 8.11 (dd, J=8.4, 1.4 Hz, 1H), 7.43 (dd, J=8.4, 4.4 Hz, 1H), 7.10–7.20 (m, 5H), 6.30 (br s, 2H), 5.83 (m, 1H), 4.72 (apparent t, J=7.8 Hz, 2H), 3.54 (s, 2H), 3.35 (apparent q, J=6.5 Hz, 2H), 2.88 (apparent t, J=7.8 Hz, 2H), 1.80–1.90 (m, 4H), 1.45–1.65 (m, 4H), 1.00 (t, J=7.3 Hz, 3H); HRMS (EI) calcd for $C_{25}H_{30}N_6O$ (M$^+$) 430.2481, found 430.2490.

EXAMPLE 56

Compound of Formula I

Benzyl N-[4-(4-Amino-2-butyl-1H-imidazo[4,5-c]
[1,5]naphthyridin-1-yl)butyl]carbamate

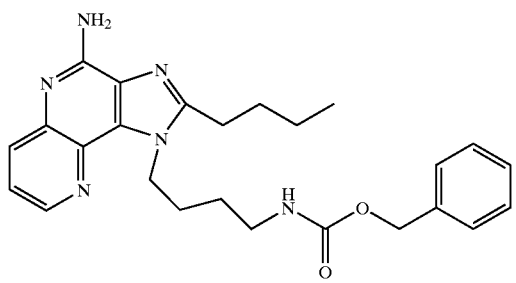

Using the general method of Example 55, benzyl chloroformate (83 μL, 0.58 mmol) was reacted with 4-(4-amino-2-butyl-1H-imidazo[4,5-c][1,5]naphthyridin-1-yl)butaneamine (0.15 g, 0.48 mmol) to provide 0.18 g of benzyl N-[4-(4-amino-2-butyl-1H-imidazo[4,5-c][1,5]naphthyridin-1-yl)butyl]carbamate as a white powder.

EXAMPLE 57

Compound of Formula I 9H-9-Fluorenylmethyl N-[4-(4-Amino-2-butyl-1H-imidazo[4,5-c][1,5]naphthyridin-1-yl)butyl]carbamate

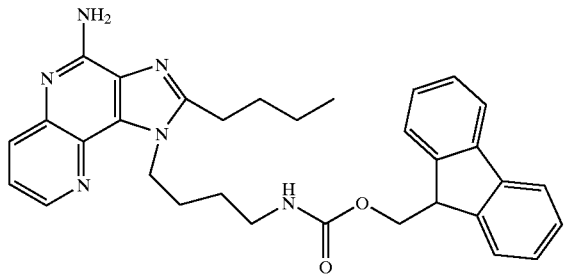

Using the general method of Example 55, 9-fluorenylmethyl chloroformate (0.085 g, 0.33 mmol) was reacted with 4-(4-amino-2-butyl-1H-imidazo[4,5-c][1,5]naphthyridin-1-yl)butaneamine (0.105 g, 0.33 mmol) to provide 0.125 g of 9H-9-fluorenylmethyl N-[4-(4-amino-2-butyl-1H-imidazo[4,5-c][1,5]naphthyridin-1-yl)butyl]carbamate as a white powder. Analysis: Calculated for $C_{32}H_{34}N_6O_2 + \frac{1}{4}H_2O$: %C, 71.29; %H, 6.45; %N, 15.59; Found: %C, 70.99; %H, 6.35; %N, 15.55.

EXAMPLE 58

Compound of Formula I

Ethyl N-[4-(4-Amino-2-butyl-1H-imidazo[4,5-c][1,5]naphthyridin-1-yl)butyl]carbamate

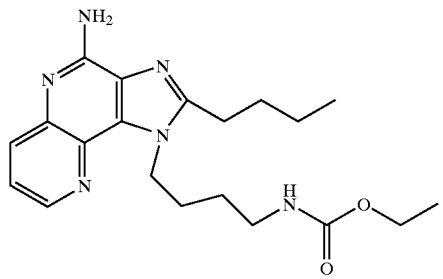

Using the general method of Example 55, ethyl chloroformate (46 μL, 0.48 mmol) was reacted with 4-(4-amino-2-butyl-1H-imidazo[4,5-c][1,5]naphthyridin-1-yl)butaneamine (0.15 g, 0.48 mmol) to provide 0.15 g of ethyl N-[4-(4-amino-2-butyl-1H-imidazo[4,5-c][1,5]naphthyridin-1-yl)butyl]carbamate as a white powder. Analysis Calculated for $C_{20}H_{28}N_6O_2$: %C, 62.48; %H, 7.34; %N, 21.86; Found: %C, 61.73; %H, 7.28; %N, 21.62.

EXAMPLE 59

Compound of Formula XXXI 1,1-Dimethyl-2-[(3-nitro[1,5]naphthyridin-4-yl)amino]ethanol Phosphorus oxychloride (4 mL, 43 mmol) was reacted with N,N-dimethylformamide (15 mL) while chilling in an ice bath. This mixture was added to a solution of 3-nitro[1,5]naphthyridin-4-ol (6.9 g, 36.1 mmol) in N,N-dimethylformamide (60 mL). The reaction mixture was warmed in an oil bath to 60° C. After 3 hours the reaction mixture was poured into ice water. The resulting precipitate was isolated by filtration and then washed with water. The wet crude 5-chloro-3-nitro[1,5]naphthyridine was suspended in dichloromethane (150 mL). Diisopropylethylamine was added followed by the slow addition of hydroxyisobutylamine (3.4 g, 40 mmol). The reaction mixture was refluxed for 2 hours and then combined with water (~100 mL). The resulting precipitate was isolated by filtration to provide 7.2 g of 1,1-dimethyl-2-[(3-nitro[1,5]naphthyridin-4-yl)amino]ethanol. A small sample was recrystallized from isopropanol to provide a pure sample, m.p. 184.5–186° C. Analysis: Calculated for $C_{12}H_{14}N_4O_3$: %C, 54.96; %H, 5.38; %N, 21.36; Found: %C, 54.63; %H, 5.36: %N, 21.51.

EXAMPLE 60

Compound of Formula XXXIII 1,1-Dimethyl-2-(2-butyl[1,5]napthyridin-1-yl)ethanol

Part A

A catalytic amount of 5% platinum on carbon was added to a suspension of 1,1-dimethyl-2-[(3-nitro[1,5]naphthyridin-4-yl)amino]ethanol (7 g, 26 mmol) in isopropanol (300 mL). The mixture was hydrogenated on a Parr apparatus at 50 psi (3.5 Kg/cm²) hydrogen pressure for 3 hours. The reaction mixture was fileted to remove the catalyst. The filtrate was concentrated under vacuum. Toluene was added to the residue and the mixture was concentrated under vacuum to remove all of the alcohol and provide crude 1,1-dimethyl-2-[(3-amino[1,5]naphthyridin-4-yl)amino]ethanol.

Part B

Trimethylorthovalerate (3.6 mL, 20 mmol) was added to a suspension of 1,1-dimethyl-2-[(3-amino[1,5]naphthyridin-4-yl)amino]ethanol 3.5 g, 13 mmol) in xylene (100 mL). The reaction mixture was heated at reflux for two days. The mixture was diluted with methanolic ammonia, placed in a Parr vessel and then heated at 110° C. for 4 hours. The reaction mixture was concentrated under vacuum. The residue was partitioned between dichloromethane and water. The layers were separated. The organic layer was washed with water, dried over magnesium sulfate and then concentrated under vacuum to provide an oil. The oil was recrystallized from methyl acetate/benzene to provide 2.8 g of 1,1-dimethyl-2-(2-butyl[1,5]napthyridin-1-yl)ethanol as a solid, m.p. 85–88.5° C. Analysis: Calculated for $C_{17}H_{22}N_4O$: %C, 68.43; %H, 7.43; %N, 18.78; Found: %C, 68.04; %H, 7.18; %N, 19.09.

EXAMPLE 61

Compound of Formula XXXIV

2-Butyl-1-(2-hydroxy-2-methylpropyl)-1H-imidazo[4,5-c][1,5]naphthyridine-5N-oxide 3-Chloroperbenzoic acid (2.6 g, 9.5 mmol) was added in 3 portions to a solution of 1,1-dimethyl-2-(2-butyl[1,5]napthyridin-1-yl)ethanol (2.6 g, 8.7 mmol) in chloroform (50 mL) in a flask covered with aluminum foil. The reaction mixture was stirred at ambient temperature for 4 hours; then it was washed twice with dilute aqueous sodium bicarbonate, washed with brine, dried over magnesium sulfate and then concentrated under vacuum. The residue was recrystallized from methyl acetate to provide 2.25 g of 2-butyl-1-(2-hydroxy-2-methylpropyl)-1H-imidazo[4,5-c][1,5]naphthyridine-5N-oxide, m.p. 156–158° C. Analysis: Calculated for: $C_{17}H_{22}N_4O_2+\frac{1}{4}H_2O$: %C, 64.03; %H, 7.11; %N, 17.57; Found: %C, 63.96; %H, 6.84; %N, 17.71.

EXAMPLE 62

Compound of Formula I 1,1-Dimethyl-2-(4-amino2-butyl[1,5]napthyridin-1-yl)ethanol

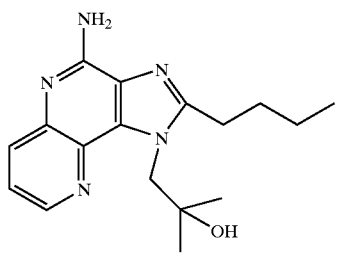

Ammonium hydroxide (15 mL) was added to a solution of 2-butyl-1-(2-hydroxy-2-methylpropyl)-1H-imidazo[4,5-c][1,5]naphthyridine-5N-oxide (1.9 g, 6.0 mmol)in dichloromethane (40 mL). Tosyl chloride (1.2 g, 6.4 mmol) was slowly added. Thin layer chromatography indicated that the reaction was proceeding slowly. Additional tosyl chloride was added twice. After thin layer chromatography indicated that the reaction was complete, the layers were separated. The organic layer was washed with dilute aqueous sodium carbonate, dried over magnesium sulfate and then concentrated under vacuum. The residue was covered with methyl acetate (10 mL), hexane (5 mL) was added and the mixture was allowed to stand overnight. The resulting crystalline solid was isolated by filtration to provide 0.9 g of 1,1-dimethyl-2-(4-amino-2-butyl[1,5]napthyridin-1-yl)ethanol, m.p. 177–179° C. Analysis: Calculated for $C_{17}H_{23}N_5O$: %C, 65.15; %H, 7.40; %N, 22.35; Found: %C, 64.97; %H, 7.33; %N, 22.71.

EXAMPLE 63

Compound of Formula XXXIII 1,1-Dimethyl-2-(2-phenylemethyl[1,5]napthyridin-1-yl)ethano Part A Phenylacetyl chloride (2.0 mL, 20 mmol) was added to a suspension of 1,1-dimethyl-2-[(3-amino[1,5]naphthyridin-4-yl)amino]ethanol 3.5 g, 13 mmol) in dichloromethane (100 mL). The reaction mixture was heated at reflux until thin layer chromatography indicated that the reaction was complete. The reaction mixture was taken on to the next step.

Part B

The material from Part A was combined with 7% ammonia in methanol (100 mL), placed in a sealed vessel, and then heated at 15° C. for 6 hours. The reaction mixture was concentrated under vacuum. The residue was combined with water (100 mL) and then extracted with dichloromethane (2×75 mL). The extracts were combined, washed with water (100 mL), dried over magnesium sulfate and then concentrated under vacuum. The residue was recrystallized from methyl acetate to provide 2.1 g of 1,1dimethyl-2(2-phenylmethyl[1,5]napthyridin-1-yl)ethanol as a solid , m.p. 150–152° C. Analysis: Calculated for $C_{20}H_{20}N_4O$: %C, 72.27; %H, 6.06; %N, 16.85; Found: %C, 72.11; %H, 6.01; %N, 17.00.

EXAMPLE 64

Compound of Formula XXXIV

2-Phenylmethyl-1-(2-hydroxy-2-methylpropyl)-1H-imidazo[4,5-c][1,5]naphthyridine-5N-oxide 3-Chloroperbenzoic acid (1.8 g, 6.6 mmol) was added in 3 portions to a solution of 1,1-dimethyl-2-(2-phenylmethyl[1,5]napthyridin-1-yl)ethanol (2 g, 6 mmol) in chloroform (50 mL) in a flask covered with aluminum foil. The reaction mixture was stirred at ambient temperature overnight; then it was washed twice with dilute aqueous sodium bicarbonate, washed with brine, dried over magnesium sulfate and then concentrated under vacuum. The residue was recrystallized from isopropanol to provide 2.25 g of 2-phenylmethyl-1-(2-hydroxy-2-methylpropyl)-1H-imidazo[4,5-c][1,5]naphthyridine-5N-oxide, m.p. 204–206° C. Analysis: Calculated for: $C_{20}H_{20}N_4O_2+\frac{1}{2}H_2O$: %C, 67.21; %H, 5.92; %N, 15.68; Found: %C, 67.05; %H, 5.65; %N, 15.39.

EXAMPLE 65

Compound of Formula I 1,1-Dimethyl-2-(4-amino2-phenylmethyl[1,5]napthyridin-1-yl)ethanol

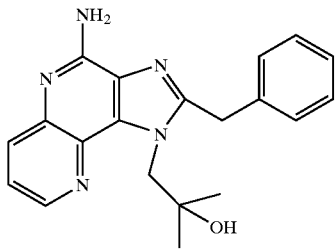

Ammonium hydroxide (10 mL) was added to a solution of 2-phenylmethyl-1-(2-hydroxy-2-methylpropyl)-1H-imidazo[4,5-c][1,5]naphthyridine-5N-oxide (1.5 g, 4.3 mmol) in dichloromethane (40 mL). Tosyl chloride (0.8 g, 4.3 mmol) was slowly added. Thin layer chromatography indicated that the reaction was proceeding slowly. Additional tosyl chloride was added twice. After thin layer chromatography indicated that the reaction was complete, the layers were separated. The organic layer was washed with dilute aqueous sodium carbonate, dried over magnesium sulfate and then concentrated under vacuum. The residue was covered with methyl acetate (10 mL), hexane (5 mL) was added and the mixture was allowed to stand overnight. The resulting crystalline solid was isolated by filtration to provide 1,1-dimethyl-2-(4-amino-2-phenylmethyl[1,5]napthyridin-1-yl)ethanol, m.p. 211–213° C. Analysis: Calculated for $C_{20}H_{21}N_5O$: %C, 69.14; %H, 6.09; %N, 20.16; Found: %C, 69.10; %H, 6.12; %N, 20.48.

EXAMPLE 66

Compound of Formula XXXI

N-Phenylmethyl-3-nitro[1,5]naphthyridin-4-amine

Phosphorus oxychloride (3.5 mL, 37.7 mmol) was reacted with N,N-dimethylformamide (15 mL) while chilling in an ice bath. This mixture was added to a solution of 3-nitro[1,5]naphthyridin-4-ol (6.0 g, 31.4 mmol) in N,N-dimethylformamide (60 mL). The reaction mixture was warmed in an oil bath to 60° C. After 3 hours the reaction mixture was poured into ice water. The resulting precipitate was isolated by filtration and then washed with water. The wet crude 5-chloro-3-nitro[1,5]naphthyridine was suspended in dichloromethane (150 mL). Diisopropylethylamine (1.2 eq) was added followed by the slow addition of benzylamine (4.7 mL g, 40 mmol). The reaction mixture was refluxed for 2 hours and then combined with water (100 mL). The layers were separated and the organic layer was concentrated under vacuum to provide 5.5 g of N-phenylmethyl-3-nitro[1,5]naphthyridin-4-amine. A small sample was recrystallized from isopropanol to provide a pure sample, m.p. 127–129° C. Analysis: Calculated for $C_{15}H_{12}N_4O_2$: %C, 64.28; %H, 4.32; %N, 19.99; Found: %C, 63.89; %H, 4.40: %N, 20.35.

EXAMPLE 67

N-(4-Phenylmethylamino[1,5]naphthyridin-3-yl)-ethoxyacetamide Hydrochloride

A catalytic amount of platinum on carbon was added to a suspension of N-phenylmethyl-3-nitro[1,5]naphthyridin-4-amine (5.1 g, 18.2 mmol) in toluene (300 mL). The reaction mixture was hydrogenated on a Parr apparatus under a hydrogen pressure of 50 psi (3.5 Kg/cm²) for 1 hour. The reaction mixture was filtered to remove the catalyst. The filtrate was concentrated under vacuum to a volume of about 200 mL and then reacted with ethoxyacetyl chloride (2.5 g, 20 mmol). The resulting yellow precipitate was isolated by filtration, suspended in diethyl ether, and then isolated by filtration to provide 5.8 g of N-(4-phenylmethylamino[1,5]naphthyridin-3-yl) ethoxyacetamide hydrochloride, m.p. 205–212° C. Analysis: Calculated for $C_{19}H_{20}N_4O_2$ HCl: %C, 61.21; %H, 5.68; %N, 15.03; Found: %C, 60.90; %H, 5.38; %N, 15.38.

EXAMPLE 68

Compound of Formula XXXIII

2-Ethoxymethyl-1-phenylmethyl-1H-imidazo[4,5-c][1,5]naphthyridine

N-(4-Phenylmethylamino[1,5]naphthyridin3yl)-ethoxyacetamide hydrochloride (5.8 g, 15.5 mmol) was combined with a 7 % solution of ammonia in methanol (100 mL), placed in a sealed Parr vessel and then heated at 150° C. for 6 hours. The reaction mixture was concentrated under vacuum. The residue was partitioned between water and dichloromethane. The dichloromethane layer was separated, washed with water, dried over magnesium sulfate and then concentrated under vacuum. The residue was recrystallized from methyl acetate to provide 4.3 g of 2-ethoxymethyl-1-phenylmethyl-1H-imidazo[4,5-c][1,5]naphthyridine, m.p. 118–119° C. Analysis: Calculated for $C_{19}H_{18}N_4O$: %C, 71.68; %H, 5.70; %N, 17.60; Found: %C, 71.44; %H, 5.60; %N, 17.66.

EXAMPLE 69

Compound of Formula XXXIV

2-Ethoxymethyl-1-phenylmethyl-1H-imidazo[4,5-c][1,5]naphthyridine-5N-oxide

3-Chloroperbenzoic acid (3.7 g, 13.4 mmol) was added in 3 portions to a solution of 2-ethoxymethyl-1-phenylmethyl-1H-imidazo[4,5-c][1,5]naphthyridine (3.9 g, 12.2 mmol) in chloroform (100 mL) in a flask covered with aluminum foil. The reaction mixture was stirred at ambient temperature overnight; and then it was washed twice with dilute aqueous sodium bicarbonate and once with brine. The chloroform layer was divided into two portions. One portion was used in the example below. The second portion was concentrated under vacuum. The residue was recrystallized from isopropyl alcohol to provide 2-ethoxymethyl-1-phenylmethyl-1H-imidazo[4,5-c][1,5]naphthyridine-5N-oxide as a solid, m.p. 187.5–189° C. Analysis: Calculated for $C_{19}H_{18}N_4O_2$+¼$H_2O$: %C, 67.52; %H, 5.49; %N, 16.58; Found: %C, 67.56; %H, 5.36; %N, 16.77.

EXAMPLE 70

Compound of Formula I

2-Ethoxymethyl-1-phenylmethyl-1H-imidazo[4,5-c][1,5]napthyridin4-amine

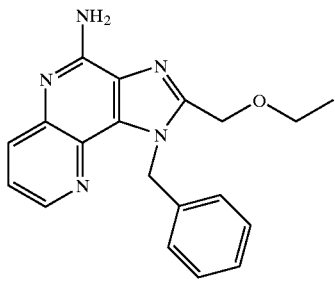

Ammonium hydroxide (20 mL) was added to the chloroform solution of 2-ethoxymethyl-1-phenylmethyl-1H-imidazo[4,5-c][1,5]naphthyridine-5N-oxide from the example above. Tosyl chloride was slowly added. Thin layer chromatography indicated that the reaction was proceeding slowly. Additional tosyl chloride was added twice. After thin layer chromatography indicated that the reaction was complete, the layers were separated. The organic layer was washed with dilute aqueous sodium carbonate, dried over magnesium sulfate and then concentrated under vacuum. The residue was covered with methyl acetate (10 mL), hexane (5 mL) was added and the mixture was allowed to stand overnight. The resulting crystalline solid was isolated by filtration to provide 2-ethoxymethyl-1-phenylmethyl-1H-imidazo[4,5-c][1,5]naphthyridin-4-amine, m.p. 173–174° C. Analysis: Calculated for $C_{19}H_{19}N_5O$: %C, 68.45; %H, 5.74; %N, 21.01; Found: %C, 68.35; %H, 5.83; %N, 21.27.

EXAMPLE 71

Compound of Formula XXXI $N^4$-(3-Isopropoxypropyl)-3-nitro[1,5]naphthyridin-4-amine Part A Phosphorus oxychloride (3.4 mL, 30 mmol) was added to chilled (ice bath) N,N-dimethylformamide (15 mL). The resulting solution was added dropwise to a solution of 3-nitro[1,5]naphthyridin-4-ol (5.73 g, 30 mmol) in N,N-dimethylformamide (35 mL). The reaction mixture was maintained at ambient temperature for 5 hours and then it was poured onto ice. The resulting yellow precipitate was isolated by filtration and then partitioned between dichloromethane (200 mL) and water (150 mL). The organic layer was separated, dried over magnesium sulfate, filtered, and then concentrated under vacuum to provide 4.2 g of crude 4-chloro-3-nitro[1,5]naphthyridine.

Part B

4-Chloro-3-nitro[1,5]naphthyridine (4.1 g), dichloromethane (150 mL), triethylamine (4.1 mL, 29.5 mmol), and 3-isopropoxypropylamine (3.3 mL, 23.8 mmol) were combined. The reaction mixture was maintained at ambient temperature overnight and then quenched with water (100 mL). The phases were separated. The aqueous phase was extracted with dichloromethane (100 mL). The organic phases were combined, dried over magnesium sulfate, filtered and then concentrated under vacuum to provide a yellow oil. The oil was purified by flash chromatography (silica gel eluting with 1:1 ethyl acetate:hexanes) to provide 4.8 g of $N^4$-(3-isopropoxypropyl)-3-nitro[1,5]naphthyridin-4-amine as a yellow powder, m.p. 62.5–63.5° C. Analysis: Calculated for $C_{14}H_{18}N_4O_3$: %C, 57.92; %H, 6.25; %N, 19.30; Found: %C, 57.96; %H, 6.19; %N, 19.51. $^1$H NMR (300 MHz, CDCl$_3$): δ 6 10.08 (broad s, 1H), 9.38 (broad s, 1H), 8.78 (m, 1H), 8.21 (dd, J=8.4,1.6 Hz, 1H), 7.64 (dd, J=8.4,4.1 Hz, 1H), 4.57 (broad s, 2H), 3.65–3.57 (m, 3H), 2.05 (t, J=5.6 Hz, 2H), 1.19 (d, J=6.0 Hz, 6H); MS (EI): m/e 290.1366 (290.1378 calc'd for $C_{14}H_{18}N_4O_3$).

EXAMPLE 72

Compound of Formula XXXII $N^4$-(3-Isopropoxypropyl)[1,5]naphthyridine-3,4-diamine $N^4$-(3-Isopropoxypropyl)-3-nitro[1,5]naphthyridin-4-amine (4.2 g, 14.5 mmol), platinum on carbon (1.1 g of 5%), and ethyl acetate (100 mL) were placed in a hydrogenation flask. The mixture was shaken under a hydrogen pressure of 50 psi (3.5 Kg/cm$^2$) for 2.5 hours. The reaction mixture was filtered and the catalyst was washed with ethyl acetate. The filtrate was dried over magnesium sulfate, filtered and then concentrated under vacuum to provide 3.6 g of $N^4$-(3-isopropoxypropyl)[1,5]naphthyridine-3,4-diamine as a bright yellow oil. $^1$H NMR (300 MHz, CDCl$_3$): δ 8.70 (dd, J=4.1,1.6 Hz, 1H), 8.39 (s, 1H), 8.17 (dd, J=8.4,1.6 Hz, 1H), 7.37 (dd, J=8.4,4.1 Hz, 1H), 5.99 (broad s, 1H), 3.98 (broad s, 2H), 3.63–3.55 (m, 5H), 1.87 (pentet, J=6.2 Hz, 2H), 1.17 (d, J=6.1 Hz, 6H); MS (EI): m/e 260.1630 (260.1637 calc'd for $C_{14}H_{20}N_4O$).

EXAMPLE 73

Compound of Formula XXXIII

2-Butyl-1-(3-isopropoxypropyl)-1H-imidazo[4,5-c][1,5]naphthyridine

Part A

Valeryl chloride (1.53 mL, 12.9 mmol) was added dropwise over a 15 minute period to a chilled (ice bath) solution of $N^4$-(3-isopropoxypropyl)[1,5]naphthyridine-3,4-diamine (3.2 g, 12.3 mmol) in dichloromethane (40 mL). The cooling bath was removed and the reaction mixture was maintained at ambient temperature for 1 hour. The solvent was removed under vacuum to provide a dark tan solid.

Part B

The material from Part A and a 7.5% solution of ammonia in methanol (100 mL) were placed in a pressure vessel. The vessel was sealed and then heated at 150° C. for 6 hours. After the mixture was cooled to ambient temperature it was concentrated under vacuum. The residue was partitioned between dichloromethane (150 mL) and water (150 mL). The fractions were separated and the aqueous fraction was extracted with dichloromethane (100 mL). The organic fractions were combined, dried over magnesium sulfate, filtered and then concentrated under vacuum to provide a brown oil. The oil was purified by flash chromatography (silica gel eluting with ethyl acetate) to provide 3.1 g of 2-butyl-1-(3-isopropoxypropyl)-1H-imidazo[4,5-c][1,5] naphthyridine as a colorless oil. $^1$H NMR (300 MHz. CDCl3): δ 9.32 (s, 1H), 8.90 (dd, J=4.3,1.7 Hz, 1H), 8.49 (dd, J=8.5,1.7 Hz, 1H), 7.57 (dd, J=8.5,4.3 Hz, 1H), 4.94 (t, J=7.0 Hz, 2H), 3.56 (pentet, J=6.1 Hz, 1H), 3.44 (t, J=5.7 Hz, 2H), 3.05 (t, J=7.9 Hz, 2H), 2.29–2.20 (m, 2H), 2.01–1.90 (m, 2H), 1.60–1.48 (m, 2H), 1.15 (d, J=6.1 Hz, 6H), 1.03 (t, J=7.3 Hz, 3H); MS (EI): m/e 326.2104 (326.2106 calc'd for $C_{19}H_{26}N_4O$).

EXAMPLE 74

Compound of Formula XXXIV

2-Butyl-1-(3-isopropoxypropyl)-1H-imidazo[4,5-c] [1,5]naphthyridine-5N-oxide

3-Chloroperbenzoic acid (1.2 g of 57–86%) was added in four portions over a period of 20 minutes to 2-butyl-1-(3-isopropoxypropyl)-1H-imidazo[4,5-c][1,5]naphthyridine (1.4 g, 4.3 mmol) in chloroform (20 mL). The reaction mixture was maintained at ambient temperature for 2 hours and then it was washed with saturated sodium bicarbonate (2×15 mL) and water (20 mL). The organic fraction was dried over magnesium sulfate, filtered and then concentrated under vacuum to provide a yellow oil. The oil was purified by column chromatography (silica gel eluting with 95:5 ethyl acetate:methanol) to provide 0.95 g of 2-butyl-1-(3-isopropoxypropyl)-1H-imidazo[4,5-c][1,5]naphthyridine-5N-oxide as a yellow solid, m.p. 92.0–93.0° C. Analysis: Calculated for $C_{19}H_{26}N_4O_2$: %C, 66.64; %H, 7.65; %N, 16.36; Found: %C, 66.18; %H, 7.39; %N, 16.26. $^1$H NMR (300 MHz, CDCl$_3$): δ 9.24 (dd, J=8.8,1.6 Hz, 1H), 9.05 (s, 1H), 8.98 (dd, J=4.3,1.6 Hz, 1H), 7.65 (dd, J=8.8,4.3 Hz, 1H), 4.89 (t, J=7.0 Hz, 2H), 3.56 (pentet, J=6.1 Hz, 1H), 3.44 (t, J=5.7 Hz, 2H), 3.02 (t, J=7.9 Hz, 2H), 2.27–2.18 (m, 2H), 1.97–1.87 (m, 2H), 1.59–1.47 (m, 2H), 1.15 (d, J=6.1 Hz, 6H), 1.02 (t, J=7.3 Hz, 3H).

EXAMPLE 75

Compound of Formula I

2-Butyl-1-(3-isopropoxypropyl)-1H-imidazo[4,5-c] [1,5]naphthyridine-4-amine

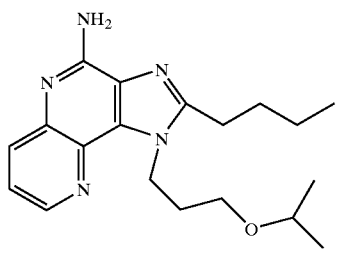

Under a nitrogen atmosphere, trichloroacetyl isocyanate (0.42 mL, 3.5 mmol) was added dropwise to a solution of 2-butyl-1-(3-isopropoxypropyl)-1H-imidazo[4,5-c][1,5] naphthyridine-5N-oxide (0.8 g, 2.3 mmol) in dichloromethane (25 mL). The reaction mixture was maintained at ambient temperature for 2 hours and then concentrated under vacuum to provide a yellow oil. The oil was dissolved in methanol (15 mL) and then sodium methoxide (0.8 mL of 25% in methanol, 3.5 mmol) was slowly added. The reaction was maintained at ambient temperature overnight. The resulting precipitate was isolated by filtration and then recrystallized from methyl acetate to provide 0.47 g of 2-butyl-1-(3-isopropoxypropyl)-1H-imidazo[4,5-c][1,5] naphthyridine-4-amine as a white crystalline solid, m.p. 174–175° C. Analysis: Calculated for $C_{19}H_{27}N_5O$: %C, 66.83; %H, 7.97; %N, 20.51; Found: %C, 66.70; %H, 7.81; %N, 20.75. $^1$H NMR (300 MHz, CDCl$_3$): δ 8.50 (dd, J=4.3,1.5 Hz, 1H), 7.90 (dd, J=8.4,1.5 Hz, 1H), 7.42 (dd, J=8.4,4.3 Hz, 1H), 6.75 (s, 2H), 4.77 (t, J=6.8 Hz, 2H), 3.50 (pentet, J=6.1 Hz, 1H), 3.35 (m, 2H), 2.95 (t, J=7.8 Hz, 2H), 2.13–2.04 (m, 2H), 1.86–1.76 (m, 2H), 1.52–1.40 (m, 2H), 1.05 (d, J=6.1 Hz, 6H), 0.97 (t, J=7.3 Hz, 3H).

EXAMPLE 76

Compound of Formula XXXI $N^4$-(3-Butoxypropyl)-3-nitro[1,5]naphthyridin-4-amine Under a nitrogen atmosphere, 3-butoxypropylamine (4.0 mL, 26 mmol) was added dropwise over a period of 10 minutes to a solution of 4-chloro-3-nitro[1,5]naphthyridine (4.6 g, 22 mmol) and triethylamine (4.6 mL, 33 mmol) in dichloromethane (150 mL). The reaction mixture was maintained at ambient temperature overnight. Water (100 mL) was added and the phases were separated. The aqueous phase was extracted with dichloromethane (100 mL). The organic fractions were combined, dried over magnesium sulfate, filtered and then concentrated under vacuum to provide a yellow oil. The oil was purified by flash chromatography (silica gel eluting with 1:1 ethyl acetate:hexanes) to provide 5.3 g of $N^4$-(3-butoxypropyl)-3-nitro[1,5] naphthyridin-4-amine as a colorless oil. $^1$H NMR (300 MHz. CDCl$_3$): δ 10.08 (broad s, 1H), 9.38 (broad s, 1H), 8.78 (m, 1H), 8.22 (dd, J=8.4,1.6 Hz, 1H), 7.64 (dd, J=8.4,4.1 Hz, 1H), 4.57 (broad s, 2H), 3.63 (t, J=5.8 Hz, 2H), 3.46 (t, J=6.7 Hz, 2H), 2.10–2.03 (m, 2H), 1.65–1.55 (m, 2H), 1.44–1.32 (m, 2H), 0.92 (t, J=7.3 Hz, 3H); MS (EI): m/e 304.1535 (304.1535 calc'd for $C_{15}H_{20}N_4O_3$).

EXAMPLE 77

Compound of Formula XXXII $N^4$-(3-Butoxypropyl)[1,5]naphthyridine-3,4-diamine

Using the method of Example 72, $N^4$-(3-butoxypropyl)-3-nitro[1,5]naphthyridin-4-amine (4.9 g, 16 mmol) was reduced to provide 4.3 g of $N^4$-(3-butoxypropyl)[1,5] naphthyridine-3,4-diamine as a bright yellow oil. Analysis: Calculated for $C_{15}H_{22}N_4O$: %C, 65.67; %H, 8.08; %N, 20.42; Found: %C, 65.48; %H, 8.07; %N, 20.41. $^1$H NMR (300 MHz, CDCl$_3$): δ 8.70 (dd, J=4.1,1.6 Hz, 1H), 8.39 (s, 1H), 8.18 (dd, J=8.4,1.6 Hz, 1H), 7.37 (dd, J=8.4,4.1 Hz, 1H), 5.97 (broad s, 1H), 3.96 (broad s, 2H), 3.63–3.56 (m, 4H), 3.44 (t, J=6.7 Hz, 2H), 1.89 (pentet, J=6.2 Hz, 2H), 1.63–1.53 (m, 2H), 1.44–1.32 (m, 2H), 0.93 (t, J=7.3 Hz, 3H); MS (EI): m/e 274.1799 (274.1793 calc'd for $C_{15}H_{22}N_4O$).

EXAMPLE 78

Compound of Formula XXXIII 1-(3-Butoxypropyl)-2-butyl-1H-imidazo[4,5-c][1,5] naphthyridine Using the general method of Example 73 Part A and Part B, $N^4$-(3-butoxypropyl)[1,5]naphthyridine-3,4-diamine (3.7 g, 13.5 mmol) was reacted with valeryl chloride (1.7 mL, 14.3 mmol) and the resulting amide intermediate was cyclized to provide 2.9 g of 1-(3-butoxypropyl)-2-butyl-1H-imidazo[4,5-c][1,5]naphthyridine as a colorless oil. A small portion was purified by flash chromatography (silica gel eluting with ethyl acetate) to provide a pure sample as a white powder, m.p. 56.5–57.5° C. Analysis: Calculated for $C_{20}H_{28}N_4O$: %C, 70.56; %H, 8.29; %N, 16.46; Found: %C, 70.48; %H, 8.25; %N, 16.61. $^1$H NMR (300 MHz, CDCl$_3$): δ 9.32 (s, 1H), 8.90 (dd, J=4.3,1.6 Hz, 1H), 8.49 (dd, J=8.5,1.6 Hz, 1H), 7.57 (dd, J=8.5,4.3 Hz, 1H), 4.94 (t, J=7.0 Hz, 2H), 3.45–3.39 (m, 4H), 3.04 (t, J=7.9 Hz, 2H), 2.26 (pentet, J=6.1 Hz, 2H), 2.01–1.91 (m, 2H), 1.62–1.48 (m, 4H), 1.45–1.33 (m, 2H), 1.03 (t, J=7.3 Hz, 3H), 0.94 (t, J=7.3 Hz, 3H).

EXAMPLE 79

Compound of Formula XXXIV 1-(3-Butoxypropyl)-2-butyl-1H-imidazo[4,5-c][1,5]naphthyridine-5N-oxide Using the general method of Example 74, 1-(3-butoxypropyl)-2-butyl-1H-imidazo[4,5-c][1,5]naphthyridine (2.2 g, 6.47 mmol) was oxidized to provide 1.6 g of 1-(3-butoxypropyl)-2-butyl-1H-imidazo[4,5-c][1,5]naphthyridine-5N-oxide as a yellow powder, m.p. 126.5–127.5° C. Analysis: Calculated for C$_{20}$H$_{28}$N$_4$O$_2$: %C, 67.39; %H, 7.92; %N, 15.72; Found: %C, 67.13; %H, 7.69; %N, 15.82. $^1$H NMR (300 MHz, CDCl$_3$): δ 9.22 (dd, J=8.1,1.5 Hz, 1H), 9.04 (s, 1H), 8.99 (dd, J=4.3,1.5 Hz, 1H), 7.65 (dd, J=8.8,4.3 Hz, 1H), 4.89 (t, J=7.0 Hz, 2H), 3.46–3.39 (m, 4H), 3.01 (t, J=7.9 Hz, 2H), 2.28–2.20 (m, 2H), 1.97–1.87 (m, 2H), 1.62–1.46 (m, 4H), 1.45–1.33 (m, 2H), 1.03 (t, J=7.3 Hz 3H), 0.94 (t, J=7.3 Hz, 3H).

EXAMPLE 80

Compound of Formula I 1-(3-Butoxypropyl)-2-butyl-1H-imidazo[4,5-c][1,5]naphthyridin-4-amine

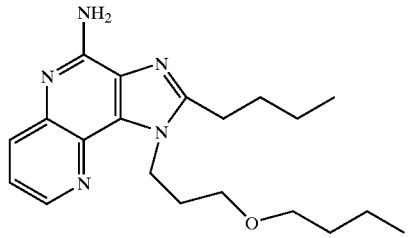

Using the general method of Example 75, 1-(3-butoxypropyl)-2-butyl-1H-imidazo[4,5-c][1,5]naphthyridine-5N-oxide (1.2 g, 3.4 mmol) was reacted with trichloroacetyl isocyanate (0.6 mL, 5.0 mmol) and the resulting intermediate was hydrolyzed to provide 0.86 g of 1-(3-butoxypropyl)-2-butyl-1H-imidazo[4,5-c][1,5]naphthyridin-4-amine as a white powder, m.p. 101.0–101.5° C. Analysis: Calculated for C$_{20}$H$_{29}$N$_5$O: %C, 67.58; %H, 8.22; %N, 19.70; Found: %C, 67.55; %H, 7.96; %N, 20.10. $^1$H NMR (300 MHz, DMSO): δ 8.50 (dd, J=4.4,1.5 Hz, 1H), 7.91 (dd, J=8.4,1.6 Hz, 1H), 7.42 (dd, J=8.4,4.4 Hz, 1H), 6.77 (s, 2H), 4.78 (t, J=6.9 Hz, 2H), 3.38–3.30 (m, 4H), 2.93 (t, J=7.8 Hz, 2H), 2.11 (pentet, J=6.1 Hz, 2H), 1.82 (pentet, J=7.6 Hz 2H), 1.51–1.39 (m, 4H), 1.37–1.25 (m, 2H), 0.96 (t, J=7.3 Hz, 3H), 0.88 (t, J=7.2 Hz, 3H).

EXAMPLE 81

Compound of Formula XXXI

N$^4$-(2-Phenoxyethyl)-3-nitro[1,5]naphthyridin4-amine

Using the general method of Example 76, 4-chloro-3-nitro[1,5]naphthyridine (5.0 g, 24 mmol) was reacted with 2-phenoxyethylamine (3.5mL, 27 mmol) to provide 6.6 g of N$^4$-(2-phenoxyethyl)-3-nitro[1,5]naphthyridin-4-amine as a yellow solid, m.p. 107–108° C. Analysis: Calculated for C$_{16}$H$_{14}$N$_4$O$_3$: %C, 61.93; %H, 4.55; %N, 18.05; Found: %C, 61.99; %H, 4.58; %N, 18.42. $^1$H NMR (300 MHz, DMSO): δ 10.25 (broad s, 1H), 9.39 (broad s, 1H), 8.81 (dd, J=4.1,1.7 Hz, 1H), 8.25 (dd, J=8.5,1.7 Hz, 1H), 7.67 (dd, J=8.5,4.1 Hz, 1H), 7.34–7.26 (m, 2H), 7.01–6.96 (m, 3H), 4.89 (broad s, 2H), 4.35 (t, J=5.1 Hz, 2H); MS (EI): m/e 310.1065 (310.1065 calc'd for C$_{16}$H$_{14}$N$_4$O$_3$).

EXAMPLE 82

Compound of Formula XXXII

N$^4$-(2-Phenoxyethyl)[1,5]naphthyridine-3,4-diamine

Using the general method of Example 77, N$^4$-(2-phenoxyethyl)-3-nitro[1,5]naphthyridin-4-amine (5.4 g, 17.4 mmol) was reduced to provide 4.6 g of N$^4$-(2-phenoxyethyl)[1,5]naphthyridine-3,4-diamine as a bright yellow oil. $^1$H NMR (300 MHz. DMSO): δ 8.68 (dd, J=4.1,1.7 Hz, 1H), 8.40 (s, 1H), 8.10 (dd, J=8.4,1.7 Hz, 1H), 7.39 (dd, J=8.4,4.1 Hz, 1H), 7.28–7.22 (m, 2H), 6.94–6.90 (m, 3H), 6.12 (t, J=7.0 Hz, 1H), 5.15 (s, 2H), 4.13 (t, J=5.5 Hz 2H), 3.93–3.87 (m, 2H); MS (CI): m/e 281 (M+H).

EXAMPLE 83

Compound of Formula XXXIII 2-(2-Butyl-1H-imidazo[4,5-c][1,5]naphthyridin-1-yl)ethyl Phenyl Ether Using the general method of Example 73 Part A and Part B, N$^4$-(2-phenoxyethyl)[1,5]naphthyridine-3,4-diamine (4.4 g, 15.7 mmol) was reacted with valeryl chloride (1.95 mL, 16.4 mmol) and the resulting amide intermediate was cyclized to provide 4.0 g of 2-(2-butyl-1H-imidazo[4,5-c][1,5]naphthyridin-1-yl)ethyl phenyl ether as a white solid, m.p. 150–150.5° C. Analysis: Calculated for C$_{21}$H$_{22}$N$_4$O: %C, 72.81; %H, 6.40; %N, 16.17; Found: %C, 72.78; %H, 6.40; %N, 16.31. $^1$H NMR (300 MHz, DMSO): δ 9.25 (s, 1H), 9.00 (dd, J=4.3,1.7 Hz, 1H), 8.52 (dd, J=8.4,1.7 Hz, 1H), 7.74 (dd, J=8.4,4.3 Hz, 1H), 7.25–7.20 (m, 2H), 6.91–6.84 (m, 3H), 5.22 (t, J=5.2 Hz, 2H), 4.53 (t, J=5.2 Hz, 2H), 3.09 (t, J=7.7 Hz, 2H), 1.91 (pentet, J=7.6 Hz, 2H), 1.55–1.43 (m, 2H), 0.97 (t, J=7.3 Hz, 3H); MS (EI): m/e 346.1794 (346.1793 calc'd for C$_{21}$H$_{22}$N$_4$O).

EXAMPLE 84

Compound of Formula XXXIV

2-Butyl-1-(2-phenoxyethyl)-1H-imidazo[4,5-c][1,5]naphthyridine-5N-oxide

Using the general method of Example 74, 2-(2-butyl-1H-imidazo[4,5-c][1,5]naphthyridin-1-yl)ethyl phenyl ether (0.6 g, 1.7 mmol) was oxidized to provide 0.44 g of 2-butyl-1-(2-phenoxyethyl)-1H-imidazo[4,5-c][1,5]naphthyridine-5N-oxide as a yellow powder. $^1$H NMR (300 MHz. CDCl$_3$):δ 9.10–9.03 (m, 3H), 7.81 (dd, J=8.7,4.3 Hz, 1H), 7.25–7.20 (m, 2H), 6.92–6.83 (m, 3H), 5.16 (t, J=4.9 Hz, 2H), 4.51 (t, J=4.9 Hz, 2H), 3.06 (t, J=7.7 Hz, 2H), 1.93–1.83 (m, 2H), 1.54–1.41 (m, 2H), 0.96 (t, J=7.3 Hz, 3H); MS (CI): m/e 363 (M+H).

EXAMPLE 85

Compound of Formula I

2-Butyl-1-(2-phenoxyethyl)-1H-imidazo[4,5-c][1,5]naphthyridin-4-amine

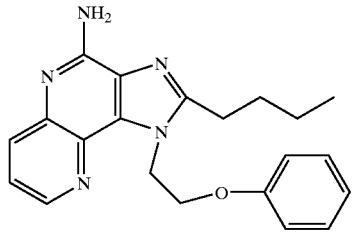

Using the general method of Example 75, 2-butyl-1-(2-phenoxyethyl)-1H-imidazo[4,5-c][1,5]naphthyridine-5N-oxide (0.38 g, 1.05 mmol) was reacted with trichloroacetyl isocyanate (0.19 mL, 1.6 mmol) and the resulting intermediate was hydrolyzed to provide 0.23 g of 2-butyl-1-(2-phenoxyethyl)-1H-imidazo[4,5-c][1,5]naphthyridin-4-amine as a white powder, m.p. 159.0–159.2° C. $^1$H NMR (300 MHz. DMSO): δ 8.52 (dd, J=4.4,1.5 Hz, 1H), 7.92 (dd, J=8.4,1.5 Hz, 1H), 7.45 (dd, J=8.4,4.4 Hz, 1H), 7.26–7.21 (m, 2H), 6.92–6.86 (m, 3H), 6.79 (s, 2H) 5.13 (t, J=5.2 Hz, 2H), 4.48 (t, J=5.2 Hz, 2H), 3.00 (t, J=7.8 Hz, 2H), 1.91–1.81 (pentet, J=7.4 Hz, 2H), 1.52–1.40 (m, 2H), 0.95 (t, J=7.3 Hz, 3H); MS (EI): m/e 361.1899 (361.1902 calc'd for $C_{21}H_{23}N_5O$).

EXAMPLE 86

Compound of Formula XXXI 1,1-Dimethylethyl N-{2-[(3-Nitro[1,5]naphthyridin-4-yl)amino]ethyl}carbamate A solution of diisopropylethylamine (13.47 g, 0.10 mole) in dichloromethane (25 mL) was added to a solution of 5-chloro-3-nitro[1,5]naphthyridine (18.2 g, 0.086 mol) in dichloromethane (250 mL). A solution of tert-butyl N-(2-aminoethyl)carbamate (16.7 g, 0.10 mol) in dichloromethane (75 mL) was slowly added to the reaction mixture. The reaction mixture was heated at reflux overnight. Additional tert-butyl N-(2-aminoethyl)carbamate (1 g) was added and the reaction mixture was heated at reflux for an additional 3 hours. The reaction mixture was allowed to cool to ambient temperature and then it was diluted with additional dichloromethane, washed with water and with brine, dried, and then concentrated under vacuum to provide a dark solid. This solid was purified by flash chromatography (silica gel eluting with dichloromethane) to provide 24.8 g of 1,1-dimethylethyl N-{2-[(3-nitro[1,5]naphthyridin-4-yl)amino]ethylcarbamate as a canary yellow solid. A portion (0.3 g) was recrystallized from toluene (10 mL) and heptane (10 mL) to provide 0.2 g of canary yellow needles, m.p. 149–151° C. Analysis: Calculated for $C_{15}H_{19}N^5O_4$: %C, 54.05; %H, 5.75; %N, 21.01; Found: %C, 54.17; %H, 5.73; %N, 20.90.

EXAMPLE 87

Compound of Formula XXXII 1,1-Dimethylethyl N-{2-[(3-Amino[1,5]naphthyridin-4-yl)amino]ethyl}carbamate 1,1-Dimethylethyl N-{2-[(3-nitro[1,5]naphthyridin-4-yl)amino]ethyl}carbamate (10 g, 0.03 mol), ethyl acetate (800 mL) and platinum on carbon catalyst were combined in a Parr bottle and then the mixture was hydrogenated overnight. The reaction mixture was filtered to remove the catalyst. The filtrate was concentrated under vacuum to provide 9.1 g of 1,1-dimethylethyl N-{2-[(3-amino[1,5]naphthyridin-4-yl)amino]ethyl}carbamate as a yellow syrup. Analysis: Calculated for $C_{15}H_{21}N_5O_2+0.1 CH_3CO_2C_2H_5$: %C, 59.25; %H, 7.04; %N, 22.43; Found: %C, 58.96; %H, 6.87; %N, 22.46.

EXAMPLE 88

Compound of Formula XXXIII 1,1-Dimethylethyl N-[2-(B-butyl-1H-imidazo[4,5-c]1,5]naphthyridin-1-yl)ethyl]carbamate 1,1-Dimethylethyl N-{2-[(3-amino[1,5]naphthyridin-4-yl)amino]ethyl}carbamate 0.6 g, 2 mmol), trimethyl orthovalerate (0.35 g, 2.1 mmol), and toluene (25 mL) were combined and heated at reflux for 2 hours. Additional trimethyl orthovalerate (1 eq.) was added and the reaction mixture was heated at reflux overnight. Xylene was added and the toluene was distilled off. The reaction was heated at reflux for an additional 8 hours. The bulk of the xylene was distilled off leaving a volume of about 5 mL. The reaction mixture was allowed to cool. The resulting precipitate was isolated by filtration, washed with heptane and dried to provide 0.35 g of 1,1-dimethylethyl N-[2-(2-butyl-1H-imidazo[4,5-c]1,5]naphthyridin-1-yl)ethyl]carbamate as an ivory powder, m.p. 198–199° C. Analysis: Calculated for $C_{20}H_{27}N_5O_2$: %C, 65.01; %H, 7.36; %N, 18.95; Found: %C, 64.75; %N, 7.57; %N, 19.09.

EXAMPLE 89

Compound of Formula XXXIII

1-{2-[(1,1-dimethylethoxycarbonyl)amino]ethyl}-2-butyl--1H-imidazo[4,5-c][1,5]naphthyridine-5N-oxide 3-Chloroperbenzoic acid (0.7 g of 57–86%) was dissolved in chloroform (10 mL). One half of this solution was added to a solution of 1,1-dimethylethyl N-[2-(2-butyl-1H-imidazo[4,5-c]1,5]naphthyridin-1-yl)ethyl]carbamate (1.0 g, 2.7 mmol) in chloroform (10 mL). The reaction mixture was stirred at ambient temperature for 30 minutes and then the remaining half of the chloroperbenzoic acid solution was added dropwise to the reaction mixture. The reaction mixture was stirred at ambient temperature for a total of 2.5 hours and then it was diluted with chloroform (50 mL); washed with sodium carbonate, with 10% sodium hydroxide, with water, and with brine; dried and concentrated under vacuum to provide 1.1 g of a yellow solid. This material was recrystallized twice from acetonitrile to pro vide 1.0 g of 1-{2-[(1,1-dimethylethoxycarbonyl)amino]ethyl}-2-butyl-1H-imidazo[4,5-c][1,5]naphthyridine-5N-oxide. Analysis: Calculated for $C_{20}H_{27}N_5O_3$: %C 62.32; %H, 7.06; %N, 18.17; Found: %C, 62.03; %H, 6.73; %N, 18.10.

EXAMPLE 90

Compound of Formula I 1,1-Dimethylethyl N-[2-(4-Amino-2-butyl-1H-imidazo[4,5-c][1,5naphthyridin-1-yl)ethyl]carbamate

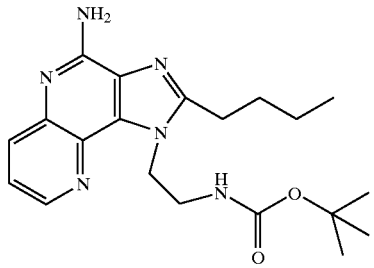

Trichloroacetyl isocyanate (4.8 mL, 40 mmol) was added via a syringe to a solution of 1-{2-[(1,1-dimethylethoxycarbonyl)amino]ethyl}-2-butyl-1H-imidazo[4,5-c][1,5]naphthyridine-5N-oxide (10.4 g, 27 mmol) in dichloromethane (75 mL). The reaction mixture was stirred at ambient temperature for 1 hour. Sodium methoxide (9 mL of 25% sodium methoxide in methanol) was added and the reaction mixture was stirred at ambient temperature overnight. Thin layer chromatography indicated that the reaction was not complete so additional sodium methoxide was added twice with each addition being followed by 2 hours of stirring at ambient temperature. The reaction mixture was diluted with dichloromethane; washed with sodium carbonate, water, and then brine; dried and then concentrated under vacuum to provide 10.4 g of a yellow solid. This material was purified by column chromatography (silica gel eluting with dichloromethane) to provide 8.5 g of a solid. This solid was recrystallized from toluene (20 mL) to provide 6.0 g of 1,1-dimethylethyl N-[2-(4-amino-2-butyl-1H-imidazo[4,5-c][1,5]naphthyridin-1-yl)ethyl]carbamate as ivory crystals, m.p. 11 8–120° C. Analysis: Calculated for $C_{20}H_{28}N_6O_2$: %C, 62.48; %H, 7.34; %N, 21.85; Found: %C, 62.31; %H, 7.23; %N, 22.13. HRMS (EI) calcd for $C_{20}H_{28}N_6O_2$ (M+) 384.2273, found 384.2273

EXAMPLE 91

Compound of Formula I 2-(4-Amino-2-butyl-1H-imidazo[4,5-c][1,5]naphthyridin-1-yl)ethaneamine

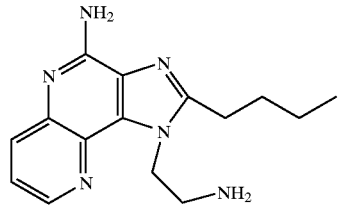

Trifluoroacetic acid (5 mL) was added to a solution of 1,1-dimethylethyl N-[2-(4-amino-2-butyl-1H-imidazo[4,5-c][1,5]naphthyridin-1-yl)ethyl]carbamate (5.7 g, 15 mmol) in dichloromethane (10 mL). The reaction mixture was stirred at ambient temperature for 1 hour. The reaction mixture was diluted with dichloromethane and then extracted with 10% hydrochloric acid. The hydrochloric acid extract was washed twice with dichloromethane and then it was made basic with ammonium hydroxide. The resulting precipitate was isolated by filtration and dried to provide 3.7 g of 2-(4-amino-2-butyl-1H-imidazo[4,5-c][1,5]naphthyridin-1-yl)ethaneamine as a white powder, m.p. 175–176° C. Analysis: Calculated for $C_{15}H_{20}N_6$: %C, 63.36; %H, 7.09; %N, 29.55; Found: %C, 62.98; %H, 6.92; %N, 29.89. HRMS (EI) calcd for $C_{15}H_{20}N_6$ (M+) 284.1749, found 284.1748.

EXAMPLE 92

Compound of Formula I $N^1$-[2-(4-Amino-2-butyl-1H-imidazo[4,5-c][1,5]naphthyridin-1-yl)ethyl]acetamide

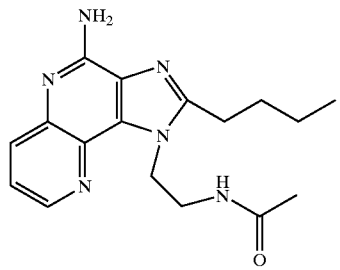

Under a nitrogen atmosphere, acetyl chloride (50 μL, 0.7 mmole) in dichloromethane (25 mL) was added dropwise to a cooled (ice bath) solution of 2-(4-amino-2-butyl-1H-imidazo[4,5-c][1,5]naphthyridin-1-yl)ethaneamine (0.2 g, 0.7 mmol) in dichloromethane (50 mL). After the addition was complete, the reaction mixture was allowed to warm to ambient temperature. After 30 minutes thin layer chromatography indicated that the reaction was complete. The reaction mixture was washed with 10% sodium hydroxide, water and brine; dried; and concentrated under vacuum to provide 0.25 g of crude product. This material was purified by column chromatography (silica gel eluting with dichloromethane) to provide 0.2 g of a solid. This solid was recrystallized from acetonitrile (30 mL) to provide 0.18 g of $N^1$-[2-(4-amino-2-butyl-1H-imidazo[4,5-c][1,5]naphthyridin-1-yl)ethyl]acetamide as a white powder, m.p. 228–230° C. Analysis: Calculated for $C_{17}H_{22}N_6O$: %C, 62.56; %H, 6.79; %N, 25.75; Found: %C, 62.50; %H, 6.59; %N, 26.04. HRMS (EI) calcd for $C_{22}H_{26}N_6O_2$ (M+) 326.1855, found 326.1846

EXAMPLE 93

Compound of Formula I $N^1$-[2-(4-Amino-2-butyl-1H-imidazo[4,5-c][1,5]naphthyridin-1-yl)ethyl]-(E)-2-butenamide

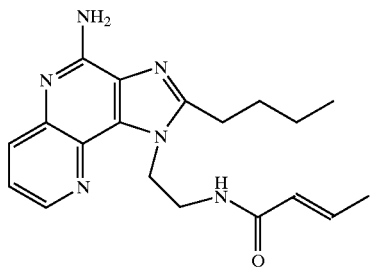

Using the general method of Example 92, crotonyl chloride (68 μL, 0.7 mmol) was reacted with 2-(4-amino-2-butyl-1H-imidazo[4,5-c][1,5]naphthyridin-1-yl)ethaneamine (0.2 g, 0.7 mmol) to provide 0.2 g of $N^1$-[2-(4-amino-2-butyl-1H-imidazo[4,5-c][1,5]naphthyridin-1-yl)ethyl]-(E)-2-butenamide as a white powder, m.p. 198–200° C. Analysis: Calculated for $C_{19}H_{24}N_6O$: %C, 64.75; %H, 6.86; %N, 23.85; Found: %C, 64.25; %H, 6.68; %N, 23.99. HRMS (EI) calcd for $C_{19}H_{24}N_6O$ (M+) 352.2011 found 352.1996

EXAMPLE 94

Compound of Formula I $N^1$-[2-(4-Amino-2-butyl-1H-imidazo[4,5-c][1,5]naphthyridin-1-yl)ethyl]-1-cyclohexanecarboxamide

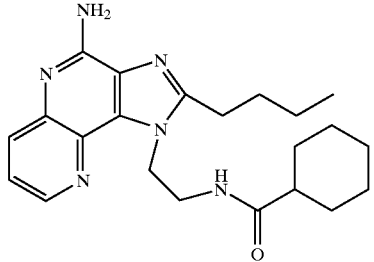

Using the general method of Example 92, cyclohexanecarbonyl chloride (94 μL, 0.7 mmol) was reacted with 2-(4-amino-2-butyl-1H-imidazo[4,5-c][1,5]naphthyridin-1-yl)ethaneamine (0.2 g, 0.7 mmol) to provide 0.2 g of $N^1$-[2-(4-amino-2-butyl-1H-imidazo[4,5-c][1,5]naphthyridin-1-yl)ethyl]-1-cyclohexanecarboxamide as a white powder, m.p. 188–190° C. Analysis: Calculated for $C_{22}H_{30}N_6O$: %C, 66.98; %H, 7.66; %N, 21.30; Found: %C, 66.72; %H, 7.57; %N, 21.48. HRMS (EI) calcd for $C_{22}H_{30}N_6O$ (M+) 394.2481 found 394.2475.

EXAMPLE 95

Compound of Formula I $N^1$-[2-(4-amino-2-butyl-1H-imidazo[4,5-c][1,5]naphthyridin-1-yl)ethyl]-3,5-di-(1,1-dimethylethyl)4-hydroxybenzamide

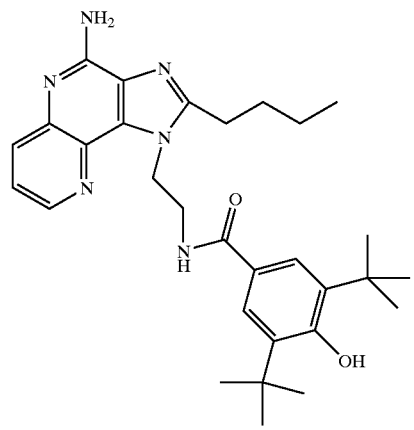

Using the general method of Example 92, 3,5-di-(1,1-dimethylethyl)-4-hydroxybenzoyl chloride (0.47 g, 1.7 mmol) was reacted with 2-(4-amino-2-butyl-1H-imidazo[4,5-c][1,5]naphthyridin-1-yl)ethaneamine (0.5 g, 1.7 mmol) to provide 0.5 g of $N^1$-[2-(4-amino-2-butyl 1H-imidazo[4,5-c][1,5]naphthyridin-1-yl)ethyl]-3,5-di-(1,1-dimethylethyl)-4-hydroxybenzamide as a white powder, m.p. 248–250° C. Analysis: Calculated for $C_{30}H_{40}N_6O_2$: %C, 69.74; %H, 7.80; %N, 16.27; Found: %C, 69.65 %H, 7.69; %N, 16.42. HRMS (EI) calcd for $C_{30}H_{40}N_6O_2$ (M+) 516.3212 found 516.3226

EXAMPLE 96

Compound of Formula I $N^1$-[2-(4-Amino-2-butyl-1H-imidazo[4,5-c][1,5]naphthyridin-1-yl)ethyl]-3-phenylpropanamide Hydrochloride

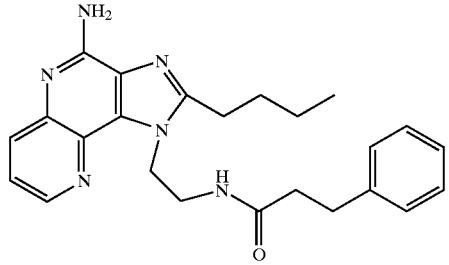

Using the general method of Example 92, hydrocinnamoyl chloride (0.1 g, 0.7 mmol) was reacted with 2-(4- amino-2-butyl-1H-imidazo[4,5-c][1,5]naphthyridin-1-yl)ethaneamine (0.2 g, 0.7 mmol). After one hour the reaction mixture was poured directly onto a silica gel column and eluted with dichloromethane at first, then 15% methanol/dichloromethane to provide 0.2 g of a solid. This solid was recrystallized from toluene to provide 0.2 g of N$^1$-[2-(4-amino-2-butyl-1H-imidazo[4,5-c][1,5]naphthyridin-1-yl)ethyl]-3-phenylpropanamide hydrochloride as a white powder, m.p. 183–185° C. Analysis: Calculated for $C_{24}H_{28}N_6O$ HCl: %C, 63.64; %H, 6.45; %N, 18.55; Found: %C, 63.68; %H, 6.43; %N, 18.55.

EXAMPLE 97

Compound of Formula I

N-[2-(4-Amino-2-butyl-1H-imidazo[4,5-c][1,5]naphthyridin-1-yl)ethyl]-5-oxotetrahydro-2-furancarboxamide

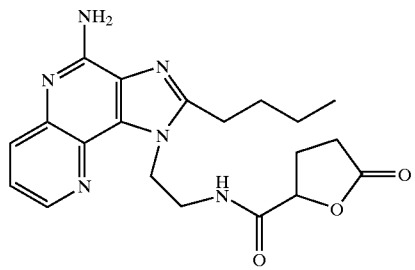

A solution of (S)-(+)-5-oxo-2-tetrahydrofurancarboxylic acid (0.23 g, 1.7 mmole in anhydrous dichloromethane (30 mL) was slowly added to a solution of 2-(4-amino-2butyl-1H-imidazo[4,5-c][1,5]naphthyridin-1-yl)ethaneamine (0.5 g, 1.7 mmol) in anhydrous dichloromethane (100 mL). The reaction mixture was stirred at ambient temperature for 30 minutes and then a solution of 1-[3-(dimethoxyamino)propyl]-3-ethylcarbodiimide hydrochloride (0.37 g, 1.9 mmol) in anhydrous dichloromethane (50 mL) was added dropwise. The reaction mixture was stirred at ambient temperature overnight and then filtered to remove solids. The filtrate was washed twice with 10% sodium hydroxide and then with brine, dried, and then concentrated under vacuum to provide 0.3 g of crude product. This material was purified by column chromatography (silica gel eluting with dichloromethane) followed by recrystallization from acetonitrile to provide 0.1 g of N-[2-(4-amino-2-butyl-1H-imidazo[4,5-c][1,5]naphthyridin-1-yl)ethyl]-5-oxotetrahydro-2-furancarboxamide as a white powder, m.p. 153–154° C. Analysis: Calculated for $C_{20}H_{24}N_6O_3$: %C, 60,59; %H, 6.10; %N, 21.19; Found: %C, 60.34; %H, 6.14; %/N, 21.13. HRMS (EI) calcd for $C_{20}H_{24}N_6O_3$ (M+) 396.1909 found 396.1905

EXAMPLE 98

Compound of Formula I

N$^1$-[2-(4-Amino-2-butyl-1H-imidazo[4,5-c][1,5]naphthyridin-1-yl)ethyl]-2-(3-hydroxyphenyl)acetamide

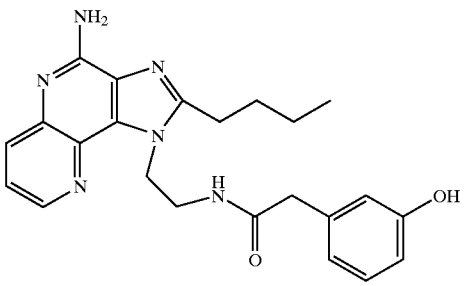

Using the general method of Example 97 3-hydroxyphenyl acetic acid (0.26 g, 1.7 mmole) was reacted with 2-(4-amino-2-butyl-1H-imidazo[4,5-c][1,5]naphthyridin-1-yl)ethaneamine (0.5 g, 1.7 mmol) to provide 0.13 g of N$^1$-[2-(4-amino-2-butyl-1H-imidazo[4,5-c][1,5]naphthyridin-1-yl)ethyl]-2-(3-hydroxyphenyl)acetamide as a white powder, m.p. 208–210° C. Analysis: Calculated for $C_{23}H_{26}N_6O_2$: %C, 66.01; %H, 6.26; %N, 20.08; Found: %C, 65.63; %H, 6.11; %N, 20.30. HRMS (EI) calcd for $C_{23}H_{26}N_6O_2$ (M+) 418.2117 found 418.2109.

EXAMPLE 99

Compound of Formula I

N-[2-(4-Amino-2-butyl-1H-imidazo[4,5-c][1,5]naphthyridin-1-yl)ethyl]-6-hydroxy-2-pyridinecarboxamide

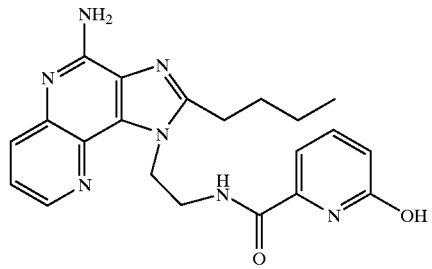

Using the general method of Example 97 6-hydroxypicolinic acid (0.24 g, 1.7 mmole) was reacted with 2-(4-amino-2-butyl-1H-imidazo[4,5-c][1,5]naphthyridin-1-yl)ethaneamine (0.5 g, 1.7 mmol) to provide 0.15 g of N-[2-(4-amino-2-butyl-1H-imidazo[4,5-c][1,5]naphthyridin-1-yl)ethyl]-6-hydroxy-2-pyridinecarboxamide as a white powder, m.p. 258–260° C. Analysis: Calculated for $C_{21}H_{23}N_7O_2+½CH_3CN$: %C, 62.03; %H, 5.80; %N, 24.66; Found: %C, 61.87; %H, 5.70; %N, 24.60.

EXAMPLE 100

Compound of Formula I

N$^1$-[2-(4-Amino-2-butyl-1H-imidazo[4,5-c][1,5]naphthyridin-1-yl)ethyl]-3,7-dimethyl-6-octenamide

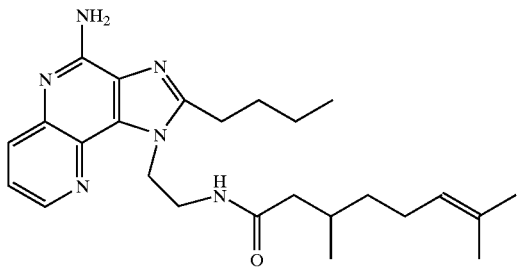

Using the general method of Example 97 citronellic acid (0.3 g, 1.7 mmole) was reacted with 2-(4-amino-2-butyl-1H-imidazo[4,5-c][1,5]naphthyridin-1-yl)ethaneamine (0.5 g, 1.7 mmol) to provide 0.5 g of N$^1$-[2-(4-amino-2-butyl-1H-imidazo[4,5-c][1,5]naphthyridin-1-yl)ethyl]-3,7-dimethyl-6-octenamide as a white whispy solid, m.p. 163–164° C. Analysis: Calculated for C$_{25}$H$_{36}$N$_6$O: %C, 68.77; %H, 8.31; %N, 19.25; Found: %C, 68.84; %H, 8.14; %N, 19.58. HRMS (EI) calcd for C$_{25}$H$_{36}$N$_6$O (M+) 436.2950 found 436.2952.

EXAMPLE 101

Compound of Formula I 1,1-Dimethylethyl N-[1-({[2-(4-Amino-2-butyl-1H-imidazo[4,5-c][1,5]naphthyridin-1-yl)ethyl]amino}carbonyl)-3-methylbutyl]carbamate

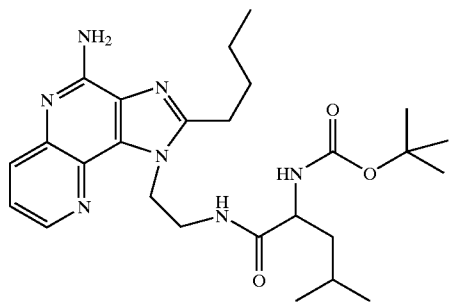

Using the general method of Example 97 N-t-BOC-L-leucine (0.41 g, 1.7 mmole) was reacted with 2-(4-amino-2-butyl-1H-imidazo[4,5-c][1,5]naphthyridin-1-yl)ethaneamine (0.5 g, 1.7 mmol) to provide 0.5 g of 1,1-dimethylethyl N-[1-(([2-(4-amino-2-butyl-1H-imidazo[4,5-c][1,5]naphthyridin-1-yl)ethyl]amino}carbonyl)-3-methylbutyl]carbamate as a white solid, m.p. 184–185° C. HRMS (EI) calcd for C$_{26}$H$_{39}$N$_7$O$_3$ (M+) 497.3114 found 497.3093.

EXAMPLE 102

Compound of Formula I

N$^1$-[2-(4-Amino-2-butyl-1H-imidazo[4,5-c][1,5]naphthyridin-1-yl)ethyl]-2-amino-4-methylpentanamide

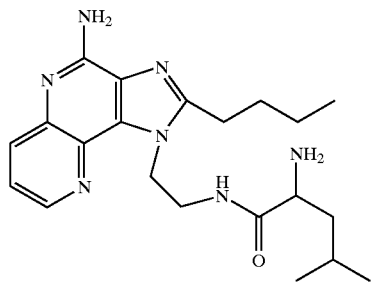

1,1-Dimethylethyl N-[1-({[2-(4-amino-2-butyl-1H-imidazo[4,5-c][1,5]naphthyridin-1-yl)ethyl]amino}carbonyl)-3-methylbutyl]carbamate (0.35 g, 0.7 mmol) was combined with 1 N hydrochloric acid (40 mL) and heated on a steam bath for 30 minutes. The reaction mixture was allowed to cool and then it was made basic with 10% sodium hydroxide. The resulting precipitate was isolated by filtration and dried to provide 0.15 g of N$^1$-[2-(4-amino-2-butyl-1H-imidazo[4,5-c][1,5]naphthyridin-1-yl)ethyl]-2-amino-4-methylpentamide as a white solid, m.p. 60–65° C. Analysis: Calculated for C$_{21}$H$_{31}$N$_7$O: %C, 63.27; %H, 7.86; %N, 24.66; Found: %C, 62.27; %H, 7.67; %N, 24.77. HRMS (EI) calcd for C$_{21}$H$_{31}$N$_7$O (M+) 397.2590 found 397.2582.

EXAMPLE 103

Compound of Formula I

N-[2-(4-Amino-2-butyl-1H-imidazo[4,5-c][1,5]naphthyridin-1-yl)ethyl]-3,5-dimethyl-4-isoxazolecarboxamide

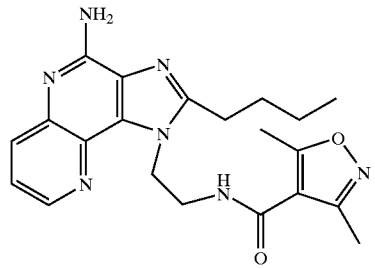

Using the general method of Example 97 3,5-dimethylisoxazole-4-carboxylic acid (0.25 g, 1.7 mmole)

was reacted with 2-(4-amino-2-butyl-1H-imidazo[4,5-c][1,5]naphthyridin-1-yl)ethaneamine (0.5 g, 1.7 mmol) to provide 0.23 g of N-[2-(4-amino-2-butyl-1H-imidazo[4,5-c][1,5]naphthyridin-1-yl)ethyl]-3,5-dimethyl-4-isoxazolecarboxamide as a white powder, m.p. 188–189° C. Analysis: Calculated for $C_{21}H_{25}N_7O_2$: %C, 61.90; %H, 6.18; %N, 24.06; Found: %C, 61.92; %H, 6.15; %N, 24.28. HRMS (EI) calcd for $C_{21}H_{25}N_7O_2$ (M+) 407.2069 found 407.2068

EXAMPLE 104

Compound of Formula II $N^1$-[2-(4-Amino-2-butyl-6,7,8,9-tetrahydro-1H-imidazo[4,5-c][1,5]naphthyridin-1-yl)ethyl]-3,5-di-(1,1-dimethylethyl)-4-hydroxybenzamide

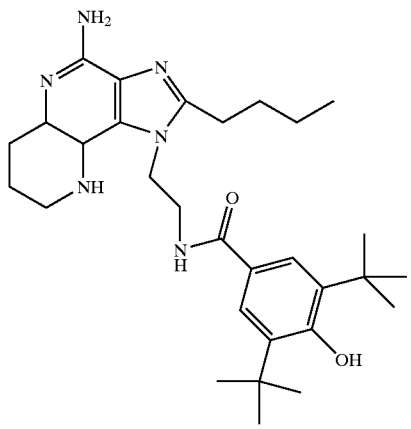

A solution of $N^1$-[2-(4-amino-2-butyl-1H-imidazo[4,5-c][1,5]naphthyridin-1-yl)ethyl]-3,5-di-(1,1-dimethylethyl)-4-hydroxybenzamide (0.1 g, 0.19 mmol) in trifluoroacetic acid (15 mL) and platinum oxide (0.1 g) were combined and hydrogenated overnight on a Parr apparatus. The reaction mixture was filtered to remove the catalyst. The filtrate was concentrated under vacuum. The residue was dissolved in dichloromethane. The dichloromethane solution was washed twice with 10% sodium hydroxide and with brine, dried and then concentrated under vacuum to provide crude product. This material was purified by chromatography eluting with 10% methanol in dichloromethane. The resulting oil was triturated with acetonitrile to provide 0.05 g of $N^1$-[2-(4-amino-2-butyl-6,7,8,9-tetrahydro-1H-imidazo[4,5-c][1,5]naphthyridin-1-yl)ethyl]-3,5-di-(1,1-dimethylethyl)-4-hydroxybenzamide as a white powder, m.p. 208–210° C. Analysis: Calculated for $C_{30}H_{44}N_6O_2+0.1\ CF_3CO_2H$: %C, 68.17; %H, 8.35; %N, 15.79; Found: %C, 68.48; %H, 8.29; %N, 16.08.

EXAMPLE 105

Compound of Formula I $N^1$-[4-(4-Amino2-butyl -1H-imidazo[4,5-c][1,5]naphthyridin-1-yl)butyl]-5-(1,3-dimethyl-2,6-oxo-2,3,6,7-tetrahydro-1H-purinyl)pentamide

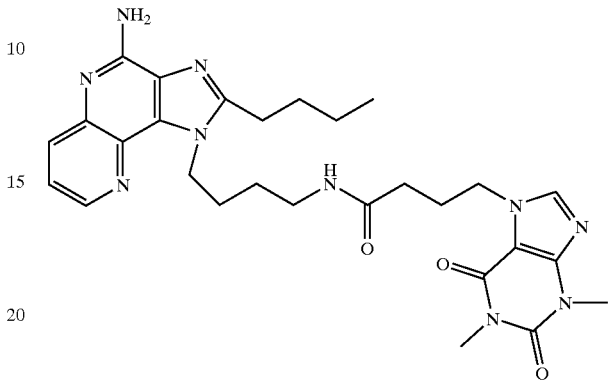

4-(4-Amino-2-butyl-1H-imidazo[4,5-c][1,5]naphthyridin-1-yl)butaneamine (0.2 g), 5-(1,3-dimethyl-2,6-oxo-2,3,6,7-tetrahydro-1H-purinyl)pentanoic acid (0.18 g) and dichloromethane (100 mL) were combined and stirred at ambient temperature for 30 minutes. 1-[3-(Dimethylamino)propyl]-3-ethylcarbodiimide (0.12 g) was added and the reaction mixture was stirred at ambient temperature for 2 hours. The reaction was filtered through a column of silica gel and eluted with 10% methanol in dichloromethane to provide 0.2 g of $N^1$-[4-(4-amino-2-butyl-1H-imidazo[4,5-c][1,5]naphthyridin-1-yl)butyl]-5-(1,3-dimethyl-2,6-oxo-2,3,6,7-tetrahydro-1H-purinyl)pentamide, m.p. 153.5–155° C. Analysis: Calculated for $C_{29}H_{38}N_{10}O_3$: %C, 60.61; %H, 6.66; %N, 24.37; Found: %C, 60.65; %H, 6.66; %N, 24.32.

EXAMPLE 106

Compound of Formula I $N^1$-[4-(4-Amino-2-butyl-1H-imidazo[4,5-c][1,5]naphthyridin-1-yl)butyl]-6-morpholinonicotinamide

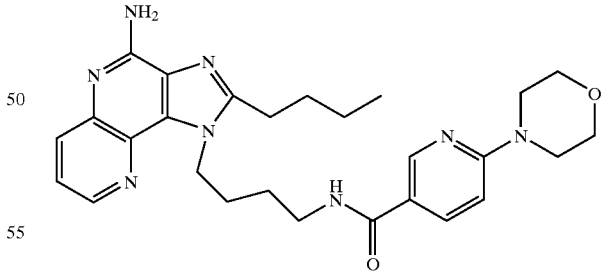

Using the general method of Example 105 6-morpholinonicotinic acid (0.12 g, 64 mmol) was reacted with 4-(4-amino-2-butyl-1H-imidazo[4,5-c][1,5]naphthyridin-1-yl)butaneamine (0.2 g, 0.64 mmol) to provide $N^1$-[4-(4-amino-2-butyl -1H-imidazo[4,5-c][1,5]naphthyridin-1-yl)butyl]-6-morpholinonicotinamide as a white solid, m.p. 95–100° C. Calculated for $C_{27}H_{34}N_8O_2+\frac{1}{2}H_2O$: %C, 63.39; %H, 6.90: %N, 21.90; Found: %C, 63.69; %H, 6.95; %N, 21.52.

EXAMPLE 107

Compound of Formula I $N^1$-[4-(4-Amino-2-butyl-1H-imidazo[4,5-c][1,5]
naphthyridin-1-yl)butyl]-6-quinolinecarboxamide

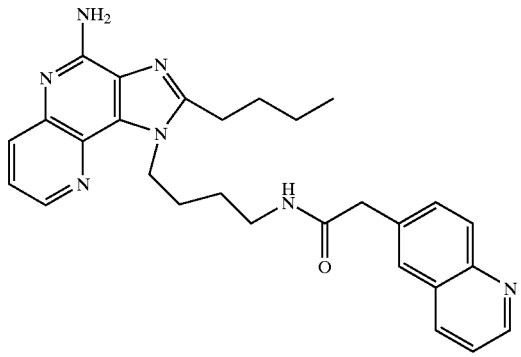

Using the general method of Example 105 6-quinolinecarboxylic acid (0.11 g, 64 mmol) was reacted with 4-(4-amino-2-butyl-1H-imidazo[4,5-c][1,5-c]naphthyridin-1-yl)butaneamine (0.2 g, 0.64 mmol) to provide $N^1$-[4-(4-amino-2-butyl -1H-imidazo[4,5-c][1,5]naphthyridin-1-yl)butyl]-6-quinolinecarboxamide as a white solid, m.p. 190–191° C. Analysis: Calculated for $C_{27}H_{29}N_7O+¼H_2O$: %C, 68.70; %H, 6.30; %N, 20.77, Found: %C, 68.54; %H, 6.21; %N, 20.93.

EXAMPLE 108

Compound of Formula I $N^1$-[4-(4-Amino-2-butyl -1H-imidazo[4,5-c][1,5]
naphthyridin-1-yl)butyl]-2-(4-hydroxy-5-methyl-2-
oxo-1,2-dihydro-1-pyrimidinyl)acetamide

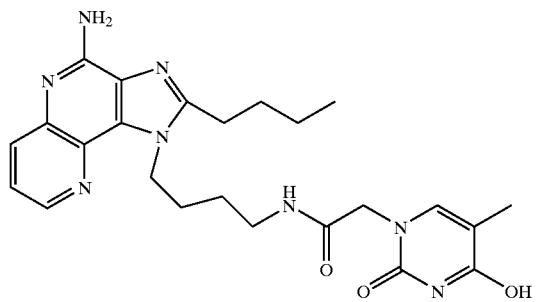

Using the general method of Example 105 2-(4-hydroxy-5-methyl-2-oxo-1,2-dihydro-1-pyrimidinyl)acetic acid (0.12 g, 64 mmol) was reacted with 4-(4-amino-2-butyl-1H-imidazo[4,5-c][1,5]naphthyridin-1-yl)butaneamine (0.2 g, 0.64 mmol) to provide 0.06 g of $N^1$-[4-(4-amino-2-butyl -1H-imidazo[4,5-c][1,5]naphthyridin-1-yl)butyl]-2-(4-hydroxy-5-methyl-2-oxo-1,2-dihydro-1-pyrimidinyl)acetamide as a solid, m.p. 242–244° C.

EXAMPLE 109

Compound of Formula I $N^1$-[4-(4-Amino-2-butyl-1H-imidazo[4,5-c][1,5]
naphthyridin-1-yl)butyl]-2-(2-pyrimidinylsulfanyl)
acetamide

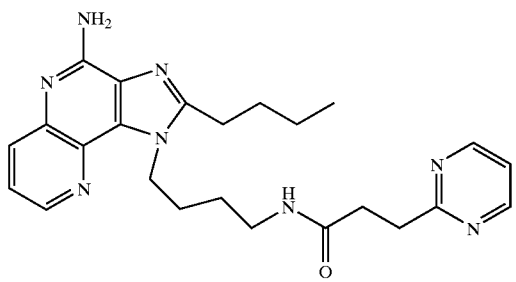

Using the general method of Example 105 (2-pyrimidinylthio)acetic acid (0.11 g, 64 mmol) was reacted with 4-(4-amino-2-butyl-1H-imidazo[4,5-c][1,5]naphthyridin-1-yl)butaneamine (0.2 g, 0.64 mmol) to provide $N^1$-[4-(4-amino-2-butyl-1H-imidazo[4,5-c][1,5]naphthyridin-1-yl)butyl]-2-(2-pyrimidinylsulfanyl)acetamide as a white solid, m.p. 156–160° C. (dec.).

EXAMPLE 110

Compound of Formula I $N^1$-[4-(4-Amino-2-butyl-1H-imidazo[4,5-c][1,5]
naphthyridin-1-yl)butyl]-2-(4-pyridylsulfanyl)
acetamide

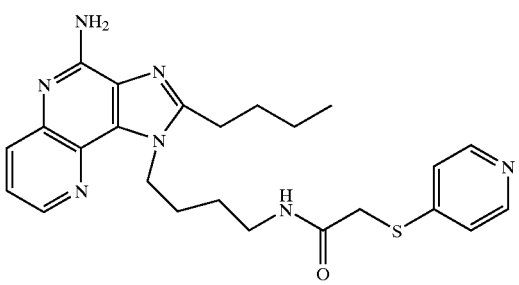

Using the general method of Example 105 (4-pyridylthio)acetic acid (0.11 g, 64 mmol) was reacted with 4-(4-amino-2-butyl-1H-imidazo[4,5-c][1,5]naphthyridin-1-yl)butaneamine (0.2 g, 0.64 mmol) to provide 0.1 g of $N^1$-[4-(4-amino-2-butyl -1H-imidazo[4,5-c][1,5]naphthyridin-1-yl)butyl]-2-(4-pyridylsulfanyl)acetamide as a solid, m.p. 127.5–129° C.

EXAMPLE 111

Compound of Formula I 4-(4-amino-1H-imidazo[4,5-c][1,5]naphthyridin-1-yl)butaneamine

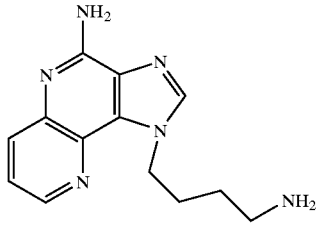

Part A

Triethylorthoformate (2.8 mL, 16.6 mmol) was added to a solution of 1,1-dimethylethyl N-{4-[(3-amino[1,5]naphthyridin-4-yl)amino]butyl} carbamate (5.0 g, 15.1 mmol) in toluene (150 mL). The reaction was heated at reflux overnight with ethanol being collected in a Dean Stark trap. The reaction mixture was heated at reflux for an additional 6 hours and then p-toluenesulfonic acid (1.4 g, 7.5 mmol) was added and the reaction was refluxed overnight. A dark orange/brown oil had formed. The toluene supernatant was decanted off and concentrated under vacuum to provide 1.1 g of 1,1-dimethylethyl N-[4-(1H-imidazo[4,5-c][1,5]naphthyridin-1-yl)butyl]carbamate. The oil was identified as 4-(1H-imidazo[4,5-c][1,5]naphthyridin-1-yl)butaneamine. This material was reacted with 1,1-dimethylethyl-dicarbonate to provide an additional 1 g of 1,1-dimethylethyl N-[4-(1H-imidazo[4,5-c][1,5]naphthyridin-1-yl)butyl]carbamate. The two lots were combined and carried on to the next step.

Part B

3-Chloroperbenzoic acid (1.86 g of 60%) was added in small portions to a solution of the material from Part A in chloroform (25 mL). The reaction was maintained at ambient temperature overnight and then it was diluted with 5% sodium carbonate solution. The layers were separated. The organic layer was concentrated under vacuum. The residue was slurried with hot methyl acetate, cooled and then filtered to provide 2.0 g of 1-{4-[(1,1-dimethylethylcarbonyl)amino]butyl}-1H-imidazo[4,5-c][4,5]naphthyridine-5N-oxide.

Part C

Tosyl chloride (0.64 g, 3.37 mmol) was slowly added in small portions to a solution of the material from Part B (1.2 g, 3.37 mmol) in dichloromethane (20 mL). After 4 hours an additional 100 mg of tosyl chloride was added to drive the reaction to completion. The reaction was quenched with concentrated ammonium hydroxide (5 mL) and water (10 mL) and stirred at ambient temperature over the weekend. The layers were separated. The organic layer was concentrated under vacuum to provide a tan solid. This solid was slurried in hot methyl acetate, cooled and the filtered to provide 0.9 g of 1,1-dimethylethyl N-[4-(4-amino-1H-imidazo[4,5-c][1,5]naphthyridin-1-yl)butyl]carbamate.

Part D

A mixture of the material from Part C and 1N hydrochloric acid (25 mL) was heated at reflux until thin layer chromatography indicated that the reaction was complete. The mixture was adjusted to pH 14 with 6N sodium hydroxide. The resulting precipitate was isolated by filtration to provide 0.2 g of 4-(4-amino-1H-imidazo[4,5-c][1,5]naphthyridin-1-yl)butaneamine as a pale yellow solid, m.p. 161–163° C. Mass spec (M+1) 257.09.

EXAMPLE 112

Compound of Formula I

N$^1$-[4-(4-Amino-2-butyl-1H-imidazo[4,5-c][1,5]naphthyridin-1-yl)butyl]-4-{[2-(dimethylamino)ethoxy](phenyl)methyl}benzamide

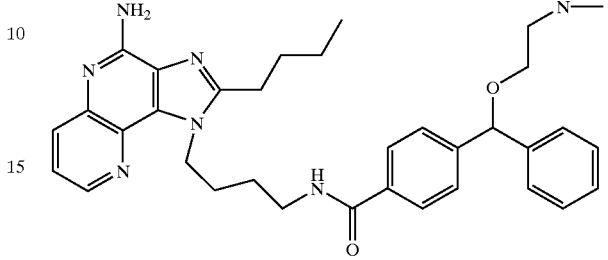

Part A

Under a nitrogen atmosphere phenyl magnesium bromide (39 mL of 3M in ether) was added via a syringe over a period of 30 minutes to a solution of methyl 4-formylbenzoate (19.2 g, 117 mmol). The mixture was allowed to stir for an additional 10 minutes and then it was quenched by the addition of 1M hydrochloric acid (125 mL). The reaction mixture was extracted with diethyl ether (2×200 mL). The combined extracts were washed with brine, dried over magnesium sulfate, filtered and then concentrated under vacuum to provide a yellow oil. This material was purified by flash chromatography (silica gel eluting with 6:1 hexanes:ethyl acetate) to provide 6.9 g of methyl 4-(α-hydroxybenzyl)benzoate as a clear oil.

Under a nitrogen atmosphere a suspension of p-toluenesulfonic acid monohydrate (10.7 g, 56 mmol) in toluene (70 mL) was heated at reflux. Water (~1 mL) was collected in a Dean Stark trap. The heating mantle was removed. To the warm mixture was added a solution of methyl 4-(α-hydroxybenzyl)benzoate (3.47 g, 14 mmol) and N,N-dimethylethanolamine (2.9 mL, 28 mmol) in a minimal amount of toluene. The mixture was heated at reflux for 20 minutes and then allowed to cool to ambient temperature. The reaction mixture was partitioned between diethyl ether and saturated aqueous sodium bicarbonate (the aqueous layer was basic). The aqueous layer was extracted with an additional 100 mL of diethyl ether. The combined organic layers were dried and then concentrated under vacuum. The residue was purified by flash chromatography (silica gel eluting with 5%, then 10% methanol in dichloromethane) to provide 2.49 g of methyl 4-[α-(2-N,N-dimethylaminoethoxy)benzyl]benzoate as a colorless oil.

1N Sodium hydroxide (2.54 mL) was added to a solution of methyl 4-[α-(2-N,N-dimethylaminoethoxy)benzyl]benzoate (0.53 g, 1.7 mmol) in methanol (10 mL). The solution was heated at reflux for 1 hour, allowed to cool to ambient temperature and then neutralized (pH 5–6) with 1N hydrochloric acid (2.54 mL). The mixture was concentrated under vacuum (bath at 45° C.). The resulting residue was extracted into a mixture of dichloromethane (15 mL) and methanol (3 mL). The extract was filtered and the filtrate was concentrated under vacuum to provide a viscous residue. Trituration with several portions of diethyl ether provided 0.39 g of 4-[α-(2-N,N-dimethylaminoethoxy)benzyl]benzoic acid as a white powder.

Part B 4-(4-Amino-2-butyl-1H-imidazo[4,5-c][1,5]naphthyridin-1-yl)butaneamine (0.130 g, 0.4175 mmol) and 4-[α-(2-N,N-dimethylaminoethoxy)benzyl]benzoic acid (0.125 g, 0.4175 mmol) were combined in dichloromethane (150 mL) and stirred at ambient temperature until a clear solution was obtained. 1-[3-(Dimethylamino)propyl]-3-ethylcarbodiimide hydrochloride (0.088 g, 0.46 mmol) was added and the reaction was maintained at ambient temperature for 2 days. The volume of dichloromethane was reduced and the concentrate was purified by flash chromatography (silica gel eluting with 10% methanol in dichloromethane) to provide 0.085 g of $N^1$-[4-(4-amino-2-butyl-1H-imidazo[4,5-c][1,5]naphthyridin-1-yl)butyl]-4-{[2-(dimethylamino)ethoxy](phenyl)methyl}benzamide as a solid, m.p. 105–108° C. Mass spec (M+1)=594.30.

EXAMPLE 113

Compound of Formula I $N^1$-[4-(4-Amino-2-butyl-1H-imidazo[4,5-c][1,5]naphthyridin-1-yl)butyl]-4-benzoylbenzamide

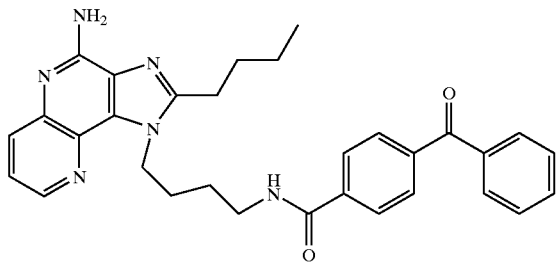

Using the general method of Example 112 Part B, 4-benzoylbenzoic acid (72 mg, 0.32 mmole) was reacted with 4-(4-amino-2-butyl-1H-imidazo[4,5-c][1,5]naphthyridin-1-yl)butaneamine (100 mg, 0.32 mmol) to provide 30 mg of $N^1$-[4-(4-amino-2-butyl-1H-imidazo[4,5-c][1,5]naphthyridin-1-yl)butyl]-4-benzoylbenzamide as a white solid. Mass-spec (M+1=521.31).

EXAMPLE 114

Compound of Formula I $N^1$-[4-(4-Amino-2-butyl-1H-imidazo[4,5-c][1,5]naphthyridin-1-yl)ethyl]-2-(5-methyl-2,4-dioxo-1,2,3,4-tetrahydro-1-pyrimidinyl)acetamide

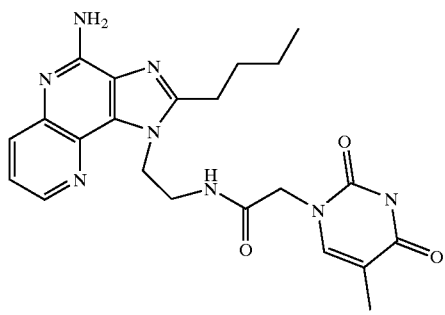

Using the general method of Example 112 Part B, thymine-1-acetic acid (130 mg, 0.70 mmole) was reacted with 4-(4-amino-2-butyl-1H-imidazo[4,5-c][1,5]naphthyridin-1-yl)ethaneamine (200 mg, 0.70 mmol) to provide 68 mg of $N^1$-[4-(4-amino-2-butyl-1H-imidazo[4,5-c][1,5]naphthyridin-1-yl)ethyl]-2-(5-methyl-2,4-dioxo-1,2,3,4-tetrahydro-1-pyrimidinyl)acetamide as a white solid, m.p. 241–242° C. Mass-spec (M+1=451.24).

EXAMPLE 115

Compound of Formula I $N^1$-[4-(4-Amino-2-butyl-1H-imidazo[4,5-c][1,5]naphthyridin-1-yl)ethyl]-6-(5-methyl-2-oxo4-imidazolidinyl)hexanmide

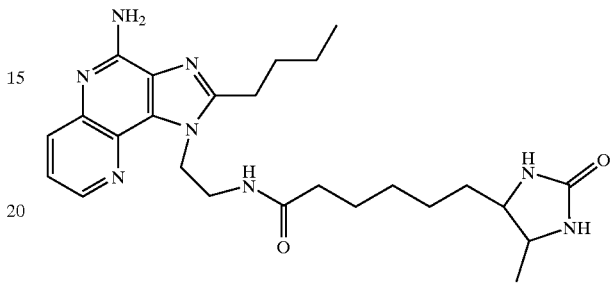

Using the general method of Example 112 Part B, D-desthiobiotin (151 mg, 0.70 mmole) was reacted with 4-(4-amino-2-butyl-1H-imidazo[4,5-c][1,5]naphthyridin-1-yl)ethaneamine (200 mg, 0.70 mmol) to provide 231 mg of $N^1$-[4-(4-amino-2-butyl-1H-imidazo[4,5-c][1,5]naphthyridin-1-yl)ethyl]-6-(5-methyl-2-oxo-4-imidazolidinyl)hexamide as a white solid, m.p. 184–186° C. Mass spec (M+1=481.35).

EXAMPLE 116

Compound of Formula I $N^1$-[4-(4-Amino-2-bultyl-1H-imidazo[4,5-c][1,5]naphthyridin-1-yl)ethyl]methanesulfonamide

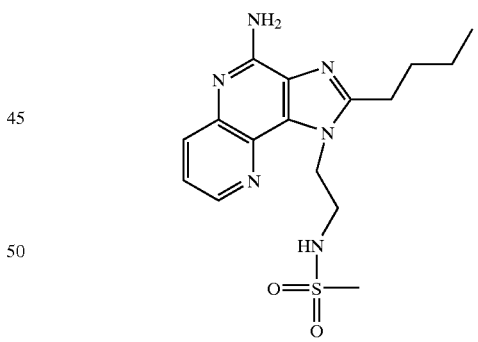

Using the method of Examples below, 4-(4-amino-2-butyl-1H-imidazo[4,5-c][1,5]naphthyridin-1-yl)ethaneamine (14 mg, 50 μmol) was reacted with methanesulfonyl chloride (4 μL, 50 μmol) to provide 5.3 mg of $N^1$-[4-(4-amino-2-butyl-1H-imidazo[4,5-c][1,5]naphthyridin-1-yl)ethyl]methanesulfonamide. 1H NMR (500 MHz, d6-DMSO) δ 6 (dd, J=4.3; 1.5 Hz, 1H), 7.92 (dd, J=8.0; 1.5 Hz, 1H), 7.44 (dd, J=8.0; 4.3 Hz, 1H), 7.30 (t, J=6 Hz, 1H), 6.76 (s, 2H), 4.77 (t, J=6 Hz, 2H), 3.50 (q, J=6 Hz, 2H), 2.98 (t, J=7 Hz, 2H), 2.85 (s, 3H), 1.82 (quintet, J=7 Hz, 2H), 1.46 (m, 2H), 0.96 (t, J=7 Hz, 3H). Mass spec by APCI (+/−) plug injection gave desired MW.

EXAMPLE 117

Compound of Formula I

N¹-[4-(4-Amino-2-butyl-1H-imidazo[4,5-c][1,5]naphthyridin-1-yl)ethyl]benzenesulfonamide

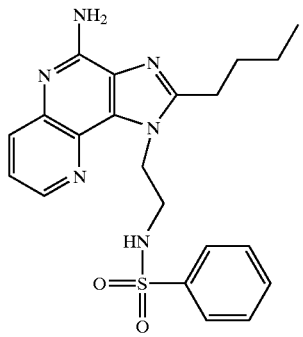

Using the method of Examples 118–152 below, 4-(4-amino-2-butyl-1H-imidazo[4,5-c][1,5]naphthyridin-1-yl)ethaneamine (14 mg, 50 μmol) was reacted with benzenesulfonyl chloride (6 μL, 50 μmol) to provide 10.9 mg of N¹-[4-(4-amino-2-butyl-1H-imidazo[4,5-c][1,5]naphthyridin-1-yl)ethyl]benzenesulfonamide. 1H NMR (500 MHz, d6-DMSO) δ=8.43 (dd, J=4.4; 1.5 Hz, 1H), 7.94 (t, J=6 Hz, 1H), 7.89 (dd, J=8.4; 1.5 Hz, 1H), 7.68 (d, J=8 Hz, 2H), 7.58 (t, J=8 Hz, 1H), 7.50 (t, J=8 Hz, 2H), 7.41 (dd, J=8.4; 4.4 Hz, 1H), 4.72 (t, J=6 Hz, 2H), 3.34 (m, 2H), 2.97 (t, J=7 Hz, 2H), 1.81 (quintet, J=7 Hz, 2H), 1.45 (sextet, J=7 Hz, 2H), 0.97 (t, J=7 Hz, 3H). Mass spec by APCI (+/−) plug injection gave desired MW.

EXAMPLES 118–152

Compounds of Formula I

The compounds of Examples 118–152 shown in the table below were prepared according to the following method. 4-(4-Amino-2-butyl-1H-imidazo[4,5-c][1,5]naphthyridin-1-yl)ethaneamine (50 μmol) was dissolved in dichloromethane (5 mL) in a screw-capped test tube and the solution was cooled in an ice-water bath. An acid chloride (50 μmol) of the formula R$_A$COCl was added as a solution in 100 μL of dichloromethane (Acid chlorides that are solids were either dissolved or suspended in ~400 μL of dichloromethane and then added). The mixture was vortexed for 15 seconds to 1 minute, becoming cloudy, and then ~80 mg of an aminomethyl polystyrene resin (0.62 meq/g, 100–200 mesh, 1% crosslink, Bachem #D-2100, lot #FM507) was added, and the mixture was vortexed for another 30 seconds. The mixture was applied to a short column (3×1 cm) of silica gel conditioned with dichloromethane. The product was eluted with 10:1 dichloromethane:methanol, collecting ~2 mL fractions. Thin layer chromatography of the fractions was performed, and fractions with the product spot were pooled and stripped to dryness in a Savant SpeedVac. Purity was checked by reversed phase-HPLC (HPLC conditions refer to using a Hewlett Packard HP 1090 system fitted with a C18 Rainin Microsorb MV column, 4.6×50 mm, particle size=3 microns, pore size=100 Angstroms. Gradient elution: linear gradient from 100% water+0.1% trifluoroacetic acid to 100% acetonitrile+0.1% trifluoroacetic acid over 5 min. at 1 mL per minute. Detection is at 220 nm and 254 nm). APCI-mass spectral data confirmed presence of the expected molecular ion, and proton nmr data supported the expected structure.

| Example # | R$_A$ Fragment | ¹H NMR (500 MHz, solvent indicated) |
|---|---|---|
| 118 | 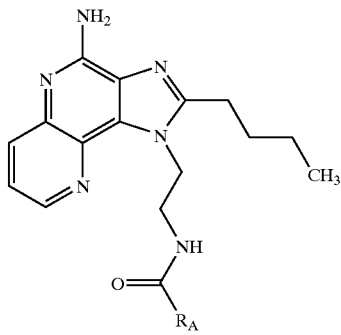 | (d$_6$-DMSO) δ 8.51(dd, J=4.4, 1.5Hz, 1H), 7.91(dd, J=8.3, 1.5Hz, 1H), 7.46(t, J=6Hz, 1H), 7.44(dd, J=8.3, 4.4Hz, 1H), 6.73(br s, 2H), 4.80(t, J=6Hz, 2H), 3.60(q, J=6Hz, 2H), 2.87(t, J=7Hz, 2H), 2.0–1.8(m, 17H), 1.43(sextet, J=7Hz, 2H), 0.96(t, J=7Hz, 3H) |

-continued

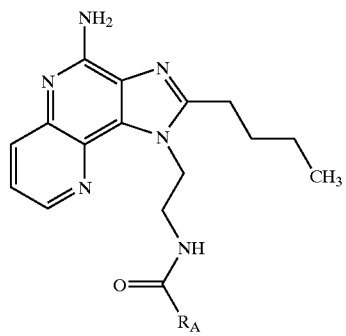

| Example # | R$_A$ Fragment | $^1$H NMR (500 MHz, solvent indicated) |
|---|---|---|
| 119 | 1-(4-chlorophenyl)cyclopentyl | (d$_6$-DMSO) δ 8.49(d, J=4.5Hz, 1H), 7.93 (d, J=8Hz, 1H), 7.65(t, J=6Hz, 1H), 7.45 (dd, J=4.5, 8Hz, 1H), 7.29(d, J=8Hz, 2H), 7.17(d, J=8Hz, 2H), 6.92(brs, 2H), 4.69(t, J=6Hz, 2H), 3.59(q, J=6Hz, 2H), 2.60(t, J=7Hz, 2H), 2.28(m, 2H), 1.67(m, 4H), 1.5–1.3(m, 6H), 0.92(t, J=7Hz, 3H) |
| 120 | 2,6-dichloro-3-methylphenyl | (d$_6$-DMSO) δ 8.96(t, J=6Hz, 1H), 8.49(dd, J=4.0, 1.5, 1H), 7.92(dd, J=8, 1.5Hz, 1H), 7.50(d, J=8Hz, 2H), 7.44(dd, J=8, 4.0Hz, 1H), 7.40(t, J=8Hz, 1H), 6.76(s, 2H), 4.85 (t, J=6Hz, 2H), 3.88(q, J=6Hz, 2H), 3.03(t, J=7Hz, 2H), 1.80(quintet, J=7Hz, 2H), 1.45(sextet, J=7Hz, 2H), 0.96(t, J=7Hz, 3H) |
| 121 | benzyloxymethyl | (d$_6$-DMSO) δ 8.52(dd, J=4.2, 1.5Hz, 1H), 8.04(t, J=6Hz, 1H), 7.95(dd, J=8.5, 1.5Hz, 1H), 7.45(dd, J=8.5, 4.2Hz, 1H), 7.4–7.2 (m, 5H), 7.00(br s, 2H), 4.84(t, J=6Hz, 2H), 4.37(s, 2H), 3.74(s, 2H), 3.65(q, J=6Hz, 2H), 2.87(t, J=7Hz, 2H), 1.77(quintet, J=7Hz, 2H), 1.40(sextet, J=7Hz, 2H), 0.94 (t, J=7Hz, 3H) |
| 122 | methyl ester of nonanedioic acid | (d$_6$-DMSO) δ 8.50(dd, J=4.4, 1.5Hz, 1H), 7.97(t, J=6Hz, 1H), 7.92(dd, J=8.4, 1.5Hz, 1H), 7.45(dd, J=8.4, 1.5Hz, 1H), 6.75(br s, 2H), 4.762(t, J=6Hz, 2H), 3.57(s, 3H), 2.88 (t, J=7Hz, 2H), 2.27(t, J=7Hz, 4H), 2.18(t, J=7Hz, 2H), 1.93(t, J=7Hz, 2H), 1.80 (quintet, J=7Hz, 2H), 2.6–1.1(m,12H), 0.96 (t, J=7Hz, 3H) |
| 123 | undec-10-enyl | (d$_6$-DMSO) δ 8.52(dd, J=4.4, 1.5Hz, 1H), 7.97(t, J=6Hz, 1H), 7.95(dd, J=8.3, 1.5Hz, 1H), 7.45(dd, J=8.3, 4.4Hz, 1H), 6.88(br s, 2H), 5.79(m, 1H), 4.98(d, J=15Hz, 1H), 4.91(d, J=13Hz, 1H), 4.76(t, J=6Hz, 2H), 3.57(q, J=6Hz, 2H), 2.88(t, J=7Hz, 2H), 2.00(q, J=7Hz, 2H), 1.93(t, J=6Hz, 2H), 1.80(quintet, J=7Hz, 2H), 1.44(sextet, J=7Hz, 2H), 1.5–1.1(m, 12H), 0.96(t, J=6Hz, 3H |
| 124 | cyclopentylmethyl | (d$_6$-DMSO) δ 8.51(dd, J=4.4, 1.7Hz, 1H), 7.96(t, J=6Hz, 1H), 7.92(dd, J=8.3, 1.5Hz, 1H), 7.44(dd, J=8.3, 4.4Hz, 1H), 6.81(br s, 2H), 3.76(t, J=6Hz, 2H), 3.59(q, J=6Hz, 2H), 2.90(t, J=7Hz, 2H), 1.94(m, 3H), 1.80 (quintet, J=7Hz, 2H), 1.58(m, 2H), 1.55–1.40(m, 6H), 0.96(m, 5H) |

-continued

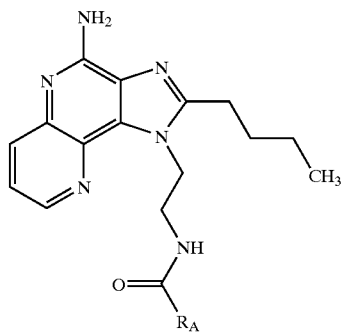

| Example # | R<sub>A</sub> Fragment | ¹H NMR (500 MHz, solvent indicated) |
|---|---|---|
| 125 | 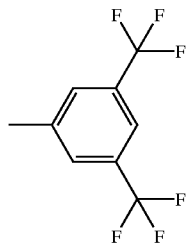 | (d₆-DMSO) δ 9.32(t, J=6Hz, 1H), 8.51(dd, J=4.4, 1.5Hz, 1H), 8.29(br s, 1H), 8.26(br s, 2H), 7.97(d, J=8Hz, 1H), 7.44(dd, J=8, 4.4Hz, 1H), 7.42(br s, 2H), 4.97(t, J=6Hz, 2H), 3.88(q, J=6Hz, 2H), 2.86(t, J=7Hz, 2H), 1.73(quintet, J=7Hz, 2H), 1.30(sextet, J=7Hz, 2H), 0.80(t, J=7Hz, 3H) |
| 126 | 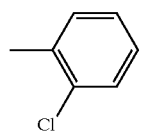 | (d₆-DMSO) δ 8.68(d, J=4.5Hz, 1H), 8.61(t, J=6Hz, 1H), 8.12(d, J=8Hz, 1H), 8.1(brs, 2H), 7.62(dd, J=8.0, 4.5Hz, 1H), 7.44(dd, J=7.5, 2Hz, 1H), 7.41(dt, J=7.5, 2.0Hz, 1H), 7.31(dt, J=7.5, 2.0Hz, 1H), 7.12(dd, J=7.5, 2Hz, 1H), 4.91(t, J=6Hz, 2H), 3.83(q, J=6Hz, 2H), 3.00(t, J=7Hz, 2H), 1.83(quintet, J=7Hz, 2H), 1.44(sextet, J=7Hz, 2H), 0.94(t, J=7Hz, 3H) |
| 127 | 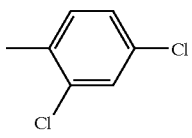 | (d₆-DMSO) δ 8.69(t, J=6Hz, 1H), 8.63(dd, J=4, 1.5Hz, 1H), 8.07(d, J=8.5Hz, 1H), 7.80(br s, 2H), 7.65(d, J=2Hz, 1H), 7.57(dd, J=8.5, 4.5Hz, 1H), 7.42(dd, J=8, 2Hz, 1H), 7.15(d, J=8Hz, 1H), 4.91(t, J=6Hz, 2H), 3.82(q, J=6Hz, 2H), 2.98(t, J=7Hz, 2H), 1.82(quintet, J=7Hz, 2H), 1.44(sextet, J=7Hz, 2H), 0.94(t, J=7Hz, 3H) |
| 128 | 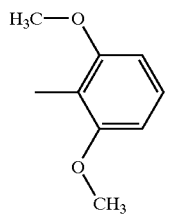 | (d₆-DMSO) δ 8.48(dd, J=4.3, 1.5Hz, 1H), 8.25(t, J=6Hz, 1H), 7.91(dd, J=8.5, 1.5Hz, 1H), 7.42(dd, J=8.5, 4.3Hz, 1H), 7.25(t, J=8Hz, 1H), 6.74(br s, 2H), 6.61(d, J=8Hz, 2H), 4.80(t, J=6Hz, 2H), 3.76(q, J=6Hz, 2H), 3.33(s, 6H), 3.00(t, J=7Hz, 2H), 1.79(quintet, J=7Hz, 2H), 1.44(sextet, J=7Hz, 2H), 0.95(t, J=7Hz, 3H) |
| 129 |  | (d₆-DMSO) δ 8.66(t, J=6Hz, 1H), 8.57(dd, J=4.3, 1.2Hz, 1H), 8.00(dd, J=8.5, 1.2Hz, 1H), 7.69(dd, J=9, 5.8Hz, 2H), 7.50(dd, J=8.4, 4.3Hz, 1H), 7.30(br s, 2H), 7.25(t, J=9Hz, 2H), 4.91(t, J=6Hz, 2H), 3.81(q, J=6Hz, 2H), 2.81(t, J=7Hz, 2H), 1.70(quintet, J=7Hz, 2H), 1.29(sextet, J=7Hz, 2H), 0.81(t, J=7Hz, 3H) |

-continued

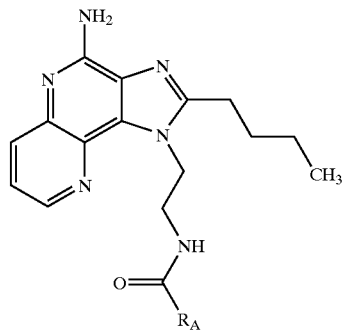

| Example # | R$_A$ Fragment | $^1$H NMR (500 MHz, solvent indicated) |
|---|---|---|
| 130 | 4-chlorophenyl | (d$_6$-DMSO) δ 8.72(t, J=6Hz, 1H), 8.52(dd, J=4.3, 1.5Hz, 1H), 7.93(dd, J=8.0, 1.5Hz, 1H), 7.72(d, J=8Hz, 2H), 7.50(d, J=8Hz, 2H), 7.44(dd, J=8, 4.3Hz, 1H), 6.80(br s, 2H), 4.90(t, J=6Hz, 2H), 3.81(q, J=6Hz, 2H), 2.79(t, J=7Hz, 2H), 1.70(quintet, J=7Hz, 2H), 1.29(sextet, J=7Hz, 2H), 0.81(t, J=7Hz, 3H) |
| 131 | 4-methoxyphenyl | (d$_6$-DMSO) δ 8.55(dd, J=4.3, 1.5Hz, 1H), 8.49(t, J=6Hz, 1H), 7.95(dd, J=8.4, 1.5Hz, 1H), 7.69(d, J=8Hz, 2H), 7.46(dd, J=8.4, 4.3Hz, 1H), 6.93(d, J=8Hz, 2H), 6.91(br s, 2H), 4.90(t, J=6Hz, 2H), 3.8(q, J=6Hz, 2H), 3.79(s, 3H), 2.79(t, J=7Hz, 2H), 1.69(quintet, J=7Hz, 2H), 1.29(sextet, J=7Hz, 2H), 0.80(t, J=7Hz, 3H) |
| 132 | 3-chlorophenyl | (d$_6$-DMSO) δ 8.76(t, J=6Hz, 1H), 8.53(dd, J=4.3, 1.5Hz, 1H), 7.95(dd, J=8.5, 1.5Hz, 1H), 7.67(br s, 1H), 7.65(d, J=8Hz, 1H), 7.57(m, 1H), 7.48–7.43(m, 2H), 7.02(br s, 2H), 4.91(t, J=6Hz, 2H), 3.82(q, J=6Hz, 2H), 2.81(t, J=7Hz, 2H), 1.71(quintet, J=7Hz, 2H), 1.31(sextet, J=7Hz, 2H), 0.82(t, J=7Hz, 3H) |
| 133 | 4-tert-butylphenyl | (d$_6$-DMSO) δ 8.69(dd, J=4.4, 1.2Hz, 1H), 8.57(t, J=6Hz, 1H), 8.22(br s, 2H). 8.12(dd, J=8.0, 1.2Hz, 1H), 7.61(m, 3H), 7.41(d, J=9Hz, 2H), 4.92(t, J=6Hz, 2H), 3.82(q, J=6Hz, 2H), 2.84(t, J=7Hz, 2H), 1.68(quintet, J=7Hz, 2H), 1.27(sextet, J=7Hz, 2H), 1.27(s, 9H), 0.78(t, J=7Hz, 3H) |
| 134 | 4-methylphenyl | (d$_6$-DMSO) δ 8.55(t, J=6Hz, 1H), 8.54(dd, J=4.5, 1.5Hz, 1H), 7.94(dd, J=8.5, 1.5Hz, 1H), 7.60(d, J=8Hz, 2H), 7.46(dd, J=8.2, 4.5Hz, 1H), 7.21(d, J=8Hz, 2H), 6.87(br s, 2H), 4.90(t, J=6Hz, 2H), 3.80(q, J=6Hz, 2H), 2.80(t, J=7Hz, 2H), 2.32(s, 3H), 1.69(quintet J=7Hz, 2H), 1.29(sextet, J=7Hz, 2H), 0.81(t, J=7Hz, 3H) |
| 135 | tert-pentyl | (d$_6$-DMSO) δ 8.58(dd, J=4.4, 1.5Hz, 1H), 8.00(dd, J=8.4, 1.5Hz, 1H), 7.97(t, J=6Hz, 1H), 7.52(dd, J=8.4, 4.4Hz, 1H), 7.35(br s, 2H), 4.77(t, J=6Hz, 2H), 3.58(q, J=6Hz, 2H), 2.93(t, J=7Hz, 2H), 1.85(s, 2H), 1.81(quintet, J=7Hz, 2H), 1.45(sextet, J=7Hz, 2H 0.96(t, J=7Hz, 3H), 0.87(s, 9H) |
| 136 | cyclopropyl | (CDCl$_3$ at 60° C.) δ 8.56(dd, J=4.0, 1.5Hz, 1H), 8.06(dd, J=8.5, 1.5Hz, 1H), 7.41(dd, J=8.8, 4.0Hz, 1H), 6.80(br s, 1H), 5.70(br s, 2H), 4.94(t, J=6Hz, 2H), 3.82(q, J=6Hz, 2H), 2.91(t, J=7Hz, 2H), 1.90(quintet, J=7Hz, 2H), 1.51(sextet, J=7Hz, 2H), 0.99(m, 1H), 0.99(t, J=7Hz, 3H), 0.79(m, 2H), 0.54(m, 2H) |

-continued

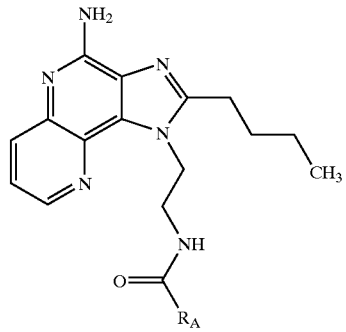

| Example # | R_A Fragment | ¹H NMR (500 MHz, solvent indicated) |
|---|---|---|
| 137 | cyclopentyl | (CDCl$_3$) δ 8.59(dd, J=4.5, 1.5Hz, 1H), 8.10 (dd, J=8.3, 1.5Hz, 1H), 7.46(dd, J=8.5, 4.5Hz, 1H), 6.79(br s, 1H), 6.02(br s, 2H), 4.96(t, J=6Hz, 2H), 3.82(q, J=6Hz, 2H), 2.93(t, J=7Hz, 2H), 2.18(quintet, J=7Hz, 1H), 1.90(quintet, J=7Hz, 2H), 1.65–1.35 (m, 10H), 1.00(t, J=7Hz, 3H) |
| 138 | ethylcyclopentyl | (CDCl$_3$) δ 8.58(dd, J=4.4, 1.5Hz, 1H), 8.09 (dd, J=8.0, 1.5Hz, 1H), 7.46(dd, J=8.3; 4.4Hz, 1H), 7.00(br s, 1H), 5.85(br s, 2H), 4.96(t, J=6Hz, 2H), 3.81(q, J=6Hz, 2H), 2.92(t, J=7Hz, 2H), 1.88(m, 3H), 1.52(m, 6H), 1.50(m, 2H), 1.49(m, 2H), 1.291(q, 2H), 1.01(t, J=7Hz, 3H), 0.85(m, 2H) |
| 139 | 4-cyanophenyl | (CDCl$_3$) δ 8.52(dd, J=4.4, 1.5Hz, 1H), 8.26 (br t, 1H), 8.09(dd, J=8.5, 1.5Hz, 1H), 7.47 (d, J=8Hz, 2H), 7.46(dd, J=8.5, 4.4Hz, 1H), 7.34(d, J=8Hz, 2H), 5.92(br s, 2H), 5.12(t, J=6Hz, 2H), 4.04(q, J=6Hz, 2H), 2.93(t, J=7Hz, 2H), 1.92(quintet, J=7Hz, 2H), 1.52(sextet, J=7Hz, 2H), 1.00(t, J=7Hz, 3H) |
| 140 | 2-thienyl | (CDCl$_3$) δ 8.65(dd, J=4.4, 1.5Hz, 1H), 8.03 (dd, J=8.5, 1.5Hz, 1H), 7.59(br t, 1H), 7.45 (dd, J=8.5, 4.4Hz, 1H), 7.35(dd, J=5, 1.2Hz, 1H), 7.10(d, J=3Hz, 1H), 6.89(dd, J=5, 3Hz, 1H), 6.32(br s, 2H), 5.08(t, J=6Hz, 2H), 4.02(q, J=6Hz, 2H), 2.92(t, J=7Hz, 2H), 1.88(quintet, J=7Hz, 2H), 1.47(sextet, J=7Hz, 2H), 0.96(t, J=7Hz, 3H) |
| 141 | 2-thienylmethyl | (CDCl$_3$) δ 8.45(dd, J=4.4, 1.5Hz, 1H), 8.08 (dd, J=8.4, 1.5Hz, 1H), 7.43(dd, J=8.3, 4.4Hz, 1H), 7.07(dd, J=5, 1.6Hz, 1H), 6.84(br t, 1H), 6.78(dd, J=5, 3.4Hz, 1H), 6.51(dd, J=3, 1Hz, 1H), 6.05(br s, 2H), 4.94(t, J=6Hz, 2H), 3.82(q, J=6Hz, 2H), 3.49(s, 2H), 2.89(t, J=7Hz, 2H), 1.88(quintet, J=7Hz, 2H), 1.50(sextet, J=7Hz, 2H), 1.00(t, J=7Hz, 3H) |
| 142 | 4-nitrophenyl | (CDCl$_3$) δ 8.52(dd, J=4.4, 1.5Hz, 1H), 8.42 (br t, 1H), 8.08(dd, J=8.3, 1.5Hz, 1H), 8.01 (d, J=9Hz, 2H), 7.48(dd, J=8.4, 4.4Hz, 1H), 7.39(d, J=9Hz, 2H), 5.80(br s, 2H), 5.12(t, J=6Hz, 2H), 4.05(q, J=6Hz, 2H), 2.94(t, J=7Hz, 2H), 1.93(quintet, J=7Hz, 2H), 1.52(sextet, J=7Hz, 2H), 1.01(t, J=7Hz, 3H) |
| 143 | 2,4,6-trimethylphenyl | (CDCl$_3$) δ 8.21(dd, J=4.4, 1.5Hz, 1H), 8.05 (dd, J=8.4, 1.5Hz, 1H), 7.53(br t, 1H), 7.28 (dd, J=8.3, 4.4Hz, 1H), 6.68(s, 2H), 6.23 (br s, 2H), 5.02(t, J=6Hz, 2H), 4.00(q, J=6Hz, 2H), 3.03(t, J=7Hz, 2H), 2.21(s, 3H), 1.99(s, 6H), 1.94(quintet, J=7Hz, 2H), 1.59 (sextet, J=7Hz, 2H), 1.03(t, J=7Hz, 3H) |

-continued

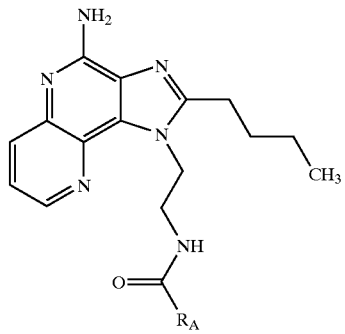

| Example # | R_A Fragment | $^1$H NMR (500 MHz, solvent indicated) |
|---|---|---|
| 144 | 2-methoxyphenyl (methoxy, methyl shown on o-methoxyphenyl) | (CDCl$_3$ at 29° C.) δ 8.59(dd, J=4.0, 1.5Hz, 1H), 8.14(dd, J=8.0, 1.5Hz, 1H), 8.09(dd, J=8, 1.5Hz, 1H), 7.87(t, J=6Hz, 1H), 7.42 (t, J=8Hz, 1H), 7.42(dd, J=8.0, 4.0Hz, 1H), 7.06(t, J=8Hz, 1H), 6.87(d, J=8Hz, 1H), 6.19(br s, 2H), 5.07(t, J=6Hz, 2H), 4.04(q, J=6Hz, 2H), 3.68(s, 3H), 2.89(t, J=7Hz, 2H), 1.80(quintet, J=7Hz, 2H), 1.39(sextet, J=7Hz, 2H), 0.88(t, J=7Hz, 3H) |
| 145 | methyl hexanoate chain | (CDCl$_3$) δ 8.60(dd, J=4.4, 1.5Hz, 1H), 8.11 (dd, J=8.5, 1.5Hz, 1H), 7.47(dd, J=8.5, 4.4Hz, 1H), 7.01(br t, 1H), 6.43(br s, 2H), 4.95 (t, J=6Hz, 2H), 3.81(q, J=6Hz, 2H), 3.63 (s, 3H), 2.93(t, J=7Hz, 2H), 2.19(t, J=7Hz, 2H), 1.92(m, 4H), 1.51(sextet, J=7Hz, 2H), 1.42(m, 4H), 1.00(t, J=7Hz, 3H) |
| 146 | 5-methyl-2-nitrofuran | (CDCl$_3$) δ 8.23(dd, J=4.4, 1.5Hz, 1H), 8.52 (br s, 1H), 8.10(dd, J=8.5, 1.5Hz, 1H), 7.53 (dd, J=8.3, 4.4Hz, 1H), 7.21(d, J=4Hz, 1H), 7.06(d, J=4Hz, 1H), 6.1(br s, 2H), 5.11(t, J=6Hz, 2H), 4.04(q, J=6Hz, 2H), 2.94(t, J=7Hz, 2H), 1.93(quintet, J=7Hz, 2H), 1.53(sextet, J=7Hz, 2H), 1.01(t, J=7Hz, 3H) |
| 147 | 2-chloro-3-methylpyridine | (CDCl$_3$) δ 8.39(dd, J=4.4, 1.5Hz, 1H), 8.31 (dd, J=5.0, 2Hz, 1H), 8.21(br t, J=6Hz, 1H), 8.00(dd, J=8.4, 1.5Hz, 1H), 7.42(dd, J=5, 8Hz, 1H), 7.33(dd, J=8.5, 4.4Hz, 1H), 7.07(dd, J=8, 5Hz, 1H), 5.84(br s, 2H), 5.06(t, J=6Hz, 2H), 4.05(q, J=6Hz, 2H), 2.97(t, J=7Hz, 2H), 1.93(quintet, J=7Hz, 2H), 1.53(sextet, J=7Hz, 2H), 1.01(t, J=7Hz, 3H) |
| 148 | 6-chloro-3-methylpyridine | (CDCl$_3$ at 60° C.) δ 8.54(dd, J=4.4, 1.5Hz, 1H), 8.33(d, J=2Hz, 1H), 8.06(dd, J=8.4, 1.5Hz, 1H), 8.06(br s, 1H), 7.56(dd, 8.5, 2Hz, 1H), 7.45(dd, J=8.4, 4.4Hz, 1H), 7.15 (d, J=8Hz, 1H), 5.72(br s, 2H), 5.08(t, J=6Hz, 2H), 4.03(q, J=6Hz, 2H), 2.93(t, J=7Hz, 2H), 1.93(quintet, J=7Hz, 2H), 1.52 (sextet, J=7Hz, 2H), 1.00(t, J=7Hz, 3H) |

-continued

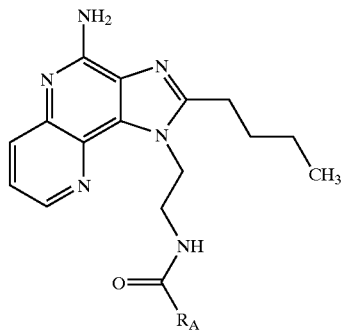

| Example # | R_A Fragment | $^1$H NMR (500 MHz, solvent indicated) |
|---|---|---|
| 149 | 4-methylphenyl-O-(CH2)5-CH3 (4-hexyloxy-methylphenyl) | (CDCl$_3$) δ 8.61(dd, J=4.4, 1.5Hz, 1H), 8.03 (dd, J=8.3, 1.5Hz, 1H), 7.50(t, J=6Hz, 1H), 7.44(dd, J=8.3, 4.4Hz, 1H), 7.42(d, J=8Hz, 2H), 6.73(d, J=8Hz, 2H), 6.45(br s, 2H), 5.06(t, J=6Hz, 2H), 4.00(q, J=6Hz, 2H), 3.90(t, J=7Hz, 2H), 2.90(t, J=7Hz, 2H), 1.84(quintet, J=7Hz, 2H), 1.74 (quintet, J=7Hz, 2H), 1.42, m, 4H), 1.28(m, 6H), 0.93(t, J=7Hz, 3H), 0.87(t, 3H) |
| 150 | 4-methylphenyl-C(O)-O-CH3 | (CDCl$_3$) δ 8.61(dd, J=4.4, 1.5Hz, 1H), 8.09 (d, J=8.5Hz, 1H), 7.90(d, J=8Hz, 2H), 7.84 (br s, 1H), 7.48(dd, J=8.5, 4.4Hz, 1H), 7.44 (d, J=8Hz, 2H), 6.4(br s, 2H), 5.12(t, J=6Hz, 2H), 3.94(t, J=7Hz, 2H), 3.91(s, 3H), 2.94(t, J=7Hz, 2H), 1.91(quintet, J=7Hz, 2H), 1.50(sextet, J=7Hz, 2H), 0.99(t, J=7Hz, 3H) |
| 151 | 2,4,6-trichloro-methylbenzene (3,5-dichloro-4-methyl substituted) | (CDCl$_3$) δ 8.48(br s, 1H), 8.22(dd, J=4.5, 1.5Hz, 1H), 8.04(dd, J=8.4, 1.5Hz, 1H), 7.33(s, 2H), 7.30(dd, J=8.4, 4.4Hz, 1H), 5.96(br s, 2H), 5.00(t, J=6Hz, 2H), 4.03(q, J=6Hz, 2H), 2.99(t, J=7Hz, 2H), 1.93 (quintet, J=7Hz, 2H), 1.54(sextet, J=7Hz, 2H), 1.03(t, J=7Hz, 3H) |
| 152 | 4-methylphenyl-O-CH3 (4-methoxymethylbenzene) | (CDCl$_3$) δ 8.41(dd, J=4.4, 1.5Hz, 1H), 8.06 (dd, J=8.3, 1.5Hz, 1H), 7.41(dd, J=8.5, 4.4Hz, 1H), 6.75(d, J=8Hz, 2H), 6.64(d, J=8Hz, 2H), 6.60(br t, 1H), 6.02(br s, 2H), 4.92 (t, J=6Hz, 2H), 3.80(q, J=4.6Hz, 2H), 3.76 (s, 3H), 3.22(s, 2H), 2.88(t, J=7Hz, 2H), 1.87(quintet, J=7Hz, 2H), 1.50(sextet, J=7Hz, 2H), 1.00(t, J=7Hz, 3H) |

EXAMPLES 153–190

Compounds of Formula I

The compounds of Examples 153–190 shown in the table below were prepared according to the following method. 4-(4-Amino-2-butyl-1H-imidazo[4,5-c][1,5]naphthyridin-1-yl)butaneamine (25 μmol) was dissolved in dichloromethane (10 mL) in a screw-capped test tube and the solution was cooled in an ice-water bath. An acid chloride (25 μmol) of the formula R$_A$COCl was added as a solution in 100 μL of dichloromethane (Acid chlorides that are solids were added directly.). The mixture was vortexed for 15 seconds to 1 minute, becoming cloudy, and then ~80 mg of an aminomethyl polystyrene resin (0.62 meq/g, 100–200 mesh, 1% crosslink, Bachem #D-2100, lot #FM507) was added, and the mixture was vortexed for another 30 seconds. The mixture was applied to a short column (3×1 cm) of silica gel conditioned with dichloromethane. The product was eluted with 10:1 dichloromethane:methanol, collecting ~2 mL fractions. Thin layer chromatography of the fractions was performed, and fractions with the product spot were pooled and stripped to dryness in a Savant SpeedVac. Purity was checked by reversed phase-HPLC (HPLC conditions refer to using a Hewlett Packard HP 1090 system fitted with a C18 Rainin Microsorb MV column, 4.6×50 mm, particle size=3 microns, pore size=100 Angstroms. Gradient elution: linear gradient from 100% water+0.1% trifluoroacetic acid to 100% acetonitrile+0.1% trifluoroacetic acid over 5 min. at 1 mL per minute. Detection is at 220 nm and 254 nm). APCI-mass spectral data confirmed presence of the expected molecular ion, and proton nmr data supported the expected structure.

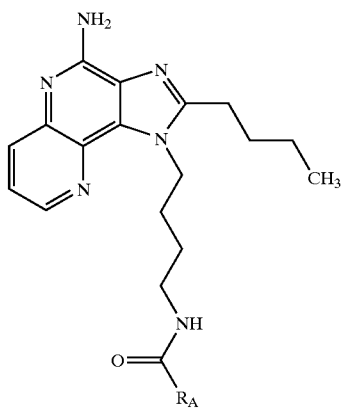

| Example # | R<sub>A</sub> Fragment | ¹H NMR (500 MHz, solvent indicated) |
|---|---|---|
| 153 | 3-bromophenyl | (CDCl₃ at 29° C.) δ 8.53(dd, J=4.4, 1.5Hz, 1H), 8.12(dd, J=8.5, 1.5Hz, 1H), 7.83(t, J=2Hz, 1H), 7.59(d, J=8Hz, 1H), 7.57(d, J=8Hz, 1H), 7.42(dd, J=8.5, 4.4Hz, 1H), 7.23(t, J=8Hz,1H), 6.73(t, J=6Hz, 1H), 6.50(br s, 2H), 4.84(t, J=6Hz, 2H), 3.60(q, J=6Hz, 2H), 2.92(t, J=7Hz, 2H), 2.04(quintet, J=7Hz, 2H), 1.88(quintet, J=7Hz, 2H), 1.80(m, J=7Hz, 2H), 1.48(m, 2H), 0.99(t, J=7Hz, 3H) |
| 154 | adamantyl | (CDCl₃ at 29° C.) δ 8.60(dd, J=4.4, 1.5Hz, 1H), 8.09(dd, J=8.5, 1.5Hz, 1H), 7.43(dd, J=8.5, 4.4Hz, 1H), 6.32(br s, 2H), 5.75(t, J=6Hz, 1H), 4.81(t, J=6Hz, 2H), 3.35(q, J=6Hz, 2H), 2.91(t, J=7Hz, 2H), 2.1–1.6(m, ca. 21H), 1.51(sextet, J=7Hz, 2H), 1.01(t, J=7Hz, 3H) |
| 155 | 1-methyl-1-(4-chlorophenyl)cyclopentyl | (CDCl₃ at 60° C.) δ 8.44(dd, J=4.4, 1.5Hz, 1H), 8.10(dd, J=8.5, 1.5Hz, 1H), 7.43(dd, J=8.5, 4.4Hz, 1H), 7.10(s, 4H), 6.00(br s, 2H), 5.60(t, J=6Hz, 1H), 4.63(t, J=6Hz, 2H), 3.30(q, J=6Hz, 2H), 2.86(t, J=7Hz, 2H), 2.37(m, 2H), 2.0–1.4(m, 14H), 1.01(t, J=7Hz, 3H) |
| 156 | 2,6-dichloromethylphenyl | (CDCl₃ at 60° C.) δ 8.33(d, J=4.4Hz, 1H), 8.08(dd, J=8.5, 1.5Hz, 1H), 7.5–7.0(m, 4H), 6.70(br s, 1H), 6.25(br s, 2H), 4.85(t, J=6Hz, 2H), 3.67(q, J=6Hz, 2H), 2.93(t, J=7Hz, 2H), 2.08(quintet, J=7Hz, 2H), 1.89(m, 4H), 1.53(sextet, J=7Hz, 2H), 1.02(t, J=7Hz, 3H) |
| 157 | benzyloxymethyl | (CDCl₃ at 60° C.) δ 8.59(dd, J=4.4, 1.5Hz, 1H), 8.10(dd, J=8.5, 1.5Hz, 1H), 7.40(dd, J=8.5,4.4Hz, 1H), 7.28(m, 3H), 7.21(m, 2H), 6.84(t, J=6Hz, 1H), 6.4(br s, 2H), 4.81 (t, J=6Hz, 2H), 4.49(s, 2H), 3.96(s, 2H), 3.42(q, J=6Hz, 2H), 2.91(t, J=7Hz, 2H), 1.95(quintet, J=7Hz, 2H), 1.90(quintet, J=7Hz,2H), 1.69(quintet, J=7Hz, 2H), 1.51 (sextet, J=7Hz, 2H), 1.01(t, J=7Hz, 3H) |

-continued

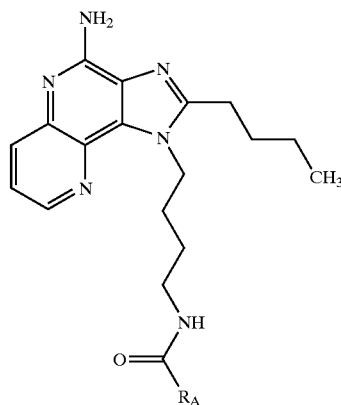

| Example # | R_A Fragment | $^1$H NMR (500 MHz, solvent indicated) |
|---|---|---|
| 158 | [nonanoate/methyl branched chain with C(=O)O-CH3] | (d$_6$-DMSO at 29° C.) δ 8.50(dd, J=4.4, 1.5Hz, 1H), 7.91(dd, J=8, 1.5Hz, 1H), 7.71(t, J=6Hz, 1H), 7.43(dd, J=8.4, 4,4Hz, 1H), 6.80 (br s, 2H), 4.79(t, J=6Hz, 2H), 3.57(s, 3H), 3.05(q, J=6Hz, 2H), 2.28(q, J=7Hz, 4H), 2.20(t, J=7Hz, 2H), 1.98(t, J=7Hz, 2H), 1.80(m, 4H), 1.6–1.1(m, 14H), 0.96(t, J=7Hz, 3H) |
| 159 | [long chain terminal alkene =CH2] | (d$_6$-DMSO at 29° C.) δ 8.51(dd, J=4.4, 1.5Hz, 1H), 7.92(dd, J=8.5, 4.4Hz, 1H), 7.72(t, J=6Hz, 1H), 7.43(dd, J=8.5, 4.4Hz, 1H), 6.86 (br s, 2H), 5.77(m, 1H), 4.98(dd, J=2Hz, 1H), 4.92(m, 1H), 4.79(t, J=6Hz, 2H), 3.08 (q, J=6Hz, 2H), 2.94(t, J=7Hz, 2H), 1.98 (quintet, J=7Hz, 2H), 1.80(m, 2H), 1.55–1.1 (m, 20H), 0.96(t, J=7Hz, 3H) |
| 160 | [cyclopentylmethyl] | (d$_6$-DMSO at 29° C.) δ 8.49(dd, J=4.4, 1.5Hz, 1H), 7.90(dd, J=8.2, 1.5Hz, 1H), 7.71(t, J=6Hz, 1H), 7.42(dd, J=8.2, 4.4Hz, 1H), 6.74 (br s, 2H), 4.79(t, J=6Hz, 2H), 3.06(q, J=6Hz, 2H), 2.92(t, J=7Hz, 2H), 2.04(m, 1H), 1.96(m, 2H), 1.82(m, 4H), 1.6–1.3(m, 10H), 1.04(m, 2H), 0.96(t, J=7Hz, 3H) |
| 161 | [3,5-bis(trifluoromethyl)phenyl] | (d$_6$-DMSO at 29° C.) δ 8.95(t, J=6Hz, 1H), 8.44(m, 3H), 8.31(s, 1H), 7.88(dd, J=8.5, 1.5Hz, 1H), 7.37(dd, J=8.5, 4.4Hz, 1H), 6.76(s, 2H), 4.82(t, J=6Hz, 2H), 3.38(m, 2H), 2.91(t, J=7Hz, 2H), 1.90(m, 2H), 1.76 (m, 2H), 1.64(m, 2H), 1.39(m, 2H), 0.86(t, J=7Hz, 3H) |
| 162 | [3,4,5-trimethoxyphenyl] | (d$_6$-DMSO at 29° C.) δ 8.44(dd, J=4.4, 1.5Hz, 1H), 8.39(t, J=6Hz, 1H), 7.89.(dd, J=8.2, 1.51Hz, 1H), 7.39(dd, J=8.2, 4.4Hz, 1H), 7.12 (s, 2H), 6.75(br s, 2H), 4.81(t, J=6Hz, 2H), 3.78(s, 6H), 3.68(s, 3H), 3.32(m, 2H), 2.92 (m, 2H), 1.90(m, 2H), 1.80(m, 2H), 1.60(m, 2H), 1.40(sextet, J=7Hz, 2H), 0.91(t, J=7Hz, 3H) |
| 163 | [pentafluorophenyl] | (d$_6$-DMSO at 29° C.) δ 8.89(t, J=6Hz, 1H), 8.51(dd, J=4.4, 1.5Hz, 1H), 7.93(d, J=8.5Hz, 1H), 7.44(dd, J=8.5, 4.4Hz, 1H), 6.95 (br s, 2H), 4.83(t, J=6Hz, 2H), 3.34(m, 2H), 2.95(t, J=7Hz, 2H), 2.90(m, 2H), 2.85(m, 2H), 1.60(quintet, J=7Hz, 2H), 1.45(m, 2H), 0.96(t, J=7Hz, 3H) |

-continued

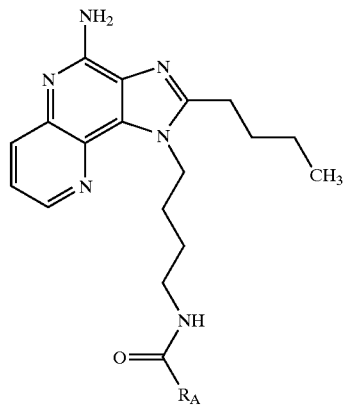

| Example # | R_A Fragment | $^1$H NMR (500 MHz, solvent indicated) |
|---|---|---|
| 164 | 2-chlorophenyl | (d$_6$-DMSO at 29° C.) δ 8.50(dd, J=4.3, 1.5Hz, 1H), 8.38(t, J=6Hz, 1H), 7.91(dd, J=8.4, 1.5Hz, 1H), 7.44(dd, J=8, 1Hz, 1H), 7.39(dt, J=8Hz, 1H), 7.43(dd, J=8.4, 4.3Hz, 1H), 7.31(dt (J=8, 1Hz, 1H), 7.27(dd, J=8, 1Hz, 1H), 6.74(s, 2H), 4.83(t, J=6Hz, 2H), 3.26 (q, J=6Hz, 2H), 2.94(t, J=7Hz, 2H), 1.95 (m, 2H), 1.83(m, 2H), 1.60(quintet, J=7Hz, 2H), 1.45 m, 2H), 0.95(t, J=7Hz, 3H) |
| 165 | 2,4-dichlorophenyl | (d$_6$-DMSO at 29° C.) δ 8.49(dd, J=4.3, 1.5Hz, 1H), 8.44(t, J=6Hz, 1H), 7.91(dd, J=8.2, 1.5Hz, 1H), 7.64(d, J=2Hz, 1H), 7.43(dd, J=8.2, 4.3Hz, 1H), 7.42(dd, J=8, 2Hz, 1H), 7.30(d, J=8Hz, 1H), 6.75(br s, 2H), 4.82(t, J=6Hz, 2H), 3.25(q, J=6Hz, 2H), 2.93(t, J=7Hz, 2H), 1.90(m, 2H), 1.82(m, 2H), 1.60 (m, 2H), 1.45(sextet, J=7Hz, 2H), 0.95(t, J=7Hz, 3H) |
| 166 | 4-fluorophenyl | (d$_6$-DMSO at 29° C.) δ 8.46(dd, J=4.3, 1.5Hz, 1H), 8.46(m, 1H), 7.89(dd, J=8.5, 1.5Hz, 1H), 7.84(dd, J=8, 5Hz, 2H), 7.40(dd, J=8.5, 4.3Hz, 1H), 7.26(t, J=9Hz, 2H), 6.74 (br s, 2H), 4.81(t, J=6Hz, 2H), 3.31(q, J=6Hz, 2H), 2.91(t, J=7Hz, 2H), 1.88(m, 2H), 1.79(m, 2H), 1.60(quintet, J=7Hz, 2H), 1.45 (m, 2H), 0.91(t, J=7Hz, 3H) |
| 167 | 4-chlorophenyl | (d$_6$-DMSO at 29° C.) δ 8.53(t, J=6Hz, 1H), 8.46(dd, J=4.4, 1.5Hz, 1H), 7.89(dd, J=8.5, 1.5Hz, 1H), 7.79(d, J=8Hz, 2H), 7.50(d, J=8.5Hz, 2H), 7.40(dd, J=8.5, 4.3Hz, 1H), 6.74(s, 2H), 4.81(t, J=6Hz, 2H), 3.30(q, J=6Hz, 2H), 2.91(t, J=7Hz, 2H), 1.92(m, 2H), 1.78(quintet, J=7Hz, 2H), 1.60(quintet, J=7Hz, 2H), 1.40(sextet, J=7Hz, 2H), 0.90 (t, J=7Hz, 3H) |
| 168 | 4-methoxyphenyl | (d$_6$-DMSO at 29° C.) δ 8.47(dd, J=4.3, 1.5Hz, 1H), 8.29(t, J=6Hz, 1H), 7.89(dd, J=8.5, 1.5Hz, 1H), 7.76(d, J=8Hz, 2H), 7.40(dd, J=8.5, 4.3Hz, 1H), 6.96(d, J=8Hz, 2H), 6.74(s, 2H), 4.81(t, J=6Hz, 2H), 3.79(s, 3H), 3.39(q, J=6Hz, 2H), 2.91(t, J=7Hz, 2H), 1.86(m, 2H), 1.79(quintet, J=7Hz, 2H), 1.60(quintet, J=7Hz, 2H), 1.41(sextet, J=7Hz, 2H), 0.91(t, J=7Hz, 3H) |
| 169 | 4-(trifluoromethyl)phenyl | (d$_6$-DMSO at 29° C.) δ 8.67(t, J=6Hz, 1H), 8.46(dd, J=4.0, 1.5Hz, 1H), 7.97(d, J=8Hz, 2H), 7.89(dd, J=8, 1.5Hz, 1H), 7.39(dd, J=8, 1.5Hz, 1H), 7.38(d, J=8Hz, 2H), 6.74 (s, 2H), 4.82(t, J=6Hz, 2H), 3.32(m, 2H), 2.91(t, J=7Hz, 2H), 1.89(m, 2H), 1.78 (quintet, J=7Hz, 2H), 1.62(quintet, J=7Hz, 2H), 1.40(sextet, J=7Hz, 2H), 0.89(t, J=7Hz, 3H) |

-continued

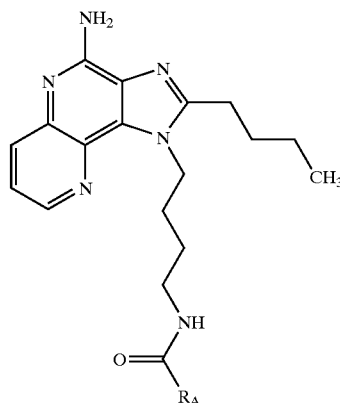

| Example # | R_A Fragment | ¹H NMR (500 MHz, solvent indicated) |
|---|---|---|
| 170 | 4-(2-methyl-2-propyl)phenyl (isopropyl with three CH₃) | (d₆-DMSO at 29° C.) δ 8.46(dd, J=4.0Hz, 1.5H), 1H), 8.35(t, J=6Hz, 1H), 7.89(dd, J=8.5, 1.5Hz, 1H), 7.71(d, J=8Hz, 2H), 7.43(d, J=8Hz, 2H), 7.40(dd, J=8, 4.0Hz, 1H), 6.73(s, 2H), 4.80(t, J=6Hz, 2H), 3.30(q, J=6Hz, 2H), 2.91(t, J=7Hz, 2H), 1.88(quintet, J=7Hz, 2H), 2.80(quintet, J=7Hz, 2H), 1.60(m, 2H), 1.39(sextet, J=7Hz, 2H), 1.29(s, 9H), 0.90(t, J=7Hz, 3H) |
| 171 | 4-methylphenyl | (d₆-DMSO at 29° C.) δ 8.47(dd, J=4.0, 1.5Hz, 1H), 8.35(t, J=6Hz, 1H), 7.89(dd, J=8.0, 1.5Hz, 1H), 7.69(d, J=8Hz, 2H), 7.40(dd, J=8.0, 4.0Hz, 1H), 7.23(d, J=8Hz, 2H), 6.74(s, 2H), 4.81(t, J=6Hz, 2H), 3.28(q, J=6Hz, 2H), 2.91(t, J=7Hz, 2H), 2.34(s, 3H), 2.90(m, 2H), 1.79(quintet, J=7Hz, 2H), 1.60(quintet, J=7Hz, 2H), 1.41(sextet, J=7Hz, 2H), 0.91(t, J=7Hz, 3H) |
| 172 | tert-butyl-CH₂ (neopentyl) | (d₆-DMSO at 29° C.) δ 8.49(dd, J=4.5, 1.5Hz, 1H), 7.90(dd, J=8.5, 1.5Hz, 1H), 7.67(t, J=6Hz, 1H), 7.42(dd, J=8.5, 4.5Hz, 1H), 6.74 (s, 2H), 4.79(t, J=6Hz, 2H), 3.06(q, J=6Hz, 2H), 2.91(t, J=7Hz, 2H), 1.87(s, 2H), 1.82 (quintet, J=7Hz, 4H), 1.46(sextet, J=7Hz, 4H), 0.96(t, J=7Hz, 3H), 0.86(s, 9H) |
| 173 | cyclopropyl | (d₆-DMSO at 29° C.) δ 8.50(dd, J=4.5, 1.5Hz, 1H), 8.00(t, J=6Hz, 1H), 7.90(dd, J=8.5, 1.5Hz, 1H), 7.43(dd, J=8.5, 4.5Hz, 1H), 6.75 (s, 2H), 4.79(t, J=6Hz, 2H), 3.10(q, J=6Hz, 2H), 2.92(t, J=7Hz, 2H), 1.82(m, 4H), 1.45 (m, 5H), 0.94(t, J=7Hz, 3H), 0.60(m, 4H) |
| 174 | cyclopentyl | (d₆-DMSO at 29° C.) δ 8.49(dd, J=4.3, 1.5Hz, 1H), 7.90(dd, J=8.4, 1.5Hz, 1H), 7.68(t, J=6Hz, 1H), 7.42(dd, J=8.4, 4.3Hz, 1H), 6.73 (br s, 2H), 4.80(t, J=6Hz, 2H), 3.06(q, J=6Hz, 2H), 2.92(t, J=7Hz, 2H), 2.44(m, 1H), 1.81(m, 4H), 1.70–1.30(m, 12H), 0.96(t, J=7Hz, 3H) |
| 175 | 2-cyclopentylethyl | (d₆-DMSO at 29° C.) δ 8.50(dd, J=4.5, 1.5Hz, 1H), 7.90(dd, J=8.0, 1.5Hz, 1H), 7.73(t, J=6Hz, 1H), 7.42(dd, J=8.0, 4.5Hz, 1H), 6.75 (s, 2H), 4.78(t, J=6Hz, 2H), 3.06(q, J=6Hz, 2H), 2.92(t, J=7Hz, 2H), 1.99(t, J=7Hz, 2H), 1.81(m, 4H), 1.63(m, 3H), 1.6–1.3(m, 10H), 1.00(m, 2H), 0.97(t, J=7Hz, 3H) |
| 176 | 4-cyanophenyl | (d₆-DMSO at 29° C.) δ 8.69(t, J=6Hz, 1H), 8.45(dd, J=4.3, 1.5Hz, 1H), 7.91(m, 4H), 7.89(dd, J=8.3, 1.5Hz, 1H), 7.40(dd, J=8.3, 4.3Hz, 1H), 6.74(s, 2H), 4.81(t, J=6Hz, 2H), 3.31(m, 2H), 2.91(t, J=7Hz, 2H), 1.90 (m, 2H), 1.79(quintet, J=7Hz, 2H), 1.60(m, 2H), 1.40(sextet, J=7Hz, 2H), 0.90(t, J=7Hz, 3H) |

-continued

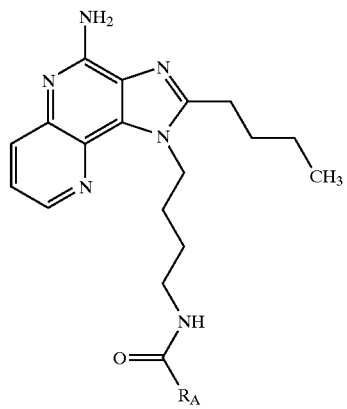

| Example # | R<sub>A</sub> Fragment | ¹H NMR (500 MHz, solvent indicated) |
|---|---|---|
| 177 | 2-methylthiophene (2-thienyl) | (d<sub>6</sub>-DMSO at 29° C.) δ 8.46(dd, J=4.3, 1.5Hz, 1H), 8.45(t, J=6Hz, 1H), 7.89(dd, J=8.4, 1.5Hz, 1H), 7.72(dd, J=5, 1Hz, 1H), 7.67(dd, J=3, 1Hz, 1H), 7.40(dd, J=8.4, 4.3Hz, 1H), 7.11(dd, J=5, 3Hz, 1H), 6.74(s, 2H), 4.82(t, J=6Hz, 2H), 3.28(q, J=6Hz, 2H), 2.92(t, J=7Hz, 2H), 1.87(m, 2H), 1.79(quintet, J=7Hz, 2H), 1.60(quintet, J=7Hz, 2H), 1.42(sextet, J=7Hz, 2H), 0.91(t, J=7Hz, 3H) |
| 178 | 2-ethylthiophene | (d<sub>6</sub>-DMSO at 29° C.) δ 8.49(dd, J=4.3, 1.5Hz, 1H), 8.05(t, J=6Hz, 1H), 7.91(dd, J=8.2, 1.5Hz, 1H), 7.43(dd, J=8.2, 4.3Hz, 1H), 7.29 (dd, J=5, 1Hz, 1H), 6.89(dd, J=5, 3Hz, 1H), 6.82(dd, J=3, 1Hz, 1H), 6.77(br s, 2H), 4.79 (t, J=6Hz, 2H), 3.56(s, 2H), 3.09(q, J=6Hz, 2H), 2.90(t, J=7Hz, 2H), 1.75(m, 4H), 1.45 (m, 4H), 0.95(t, J=7Hz, 3H) |
| 179 | 4-nitrophenyl | (d<sub>6</sub>-DMSO at 29° C.) δ 8.77(t, J=6Hz, 1H), 8.46(dd, J=4.4, 1.5Hz, 1H), 8.28(dd, J=8.5, 2.5Hz, 2H), 8.00(dd, J=8.5, 2.5Hz, 2H), 7.89(dd, J=8.3, 1.5Hz, 1H), 7.39(dd, J=8.3, 4.4Hz, 1H), 6.75(s, 2H), 4.82(t, J=6Hz, 2H), 3.32(m, 2H), 2.92(t, J=7Hz, 2H), 1.90 (m, 2H), 1.79(quintet, J=7Hz, 2H), 1.63(m, 2H), 1.42(sextet, J=7Hz, 2H), 0.91(t, J=7Hz, 3H) |
| 180 | 2,4,6-trimethylphenyl | (d<sub>6</sub>-DMSO at 29° C.) δ 8.48(dd, J=4.3, 1.5Hz, 1H), 8.14(t, J=6Hz, 1H), 7.91(dd, J=8.4, 1.5Hz, 1H), 7.42(dd, J=8.4, 4.3Hz, 1H), 6.78 (s, 2H), 6.75(br s, 2H), 4.82(t, J=6Hz, 2H), 3.22(q, J=6Hz, 2H), 2.92(t, J=7Hz, 2H), 2.50(s, 3H), 2.03(s, 6H), 1.90(m, 2H), 1.85 (quintet, J=7Hz, 2H), 1.58(m, 2H), 1.45 (sextet, J=7Hz, 2H), 0.96(t, J=7Hz, 3H) |
| 181 | perfluoroheptyl | (d<sub>6</sub>-DMSO at 29° C.) δ 9.48(t, J=6Hz, 1H), 8.52(d, J=4.3Hz, 1H), 7.94(d, J=8Hz, 1H), 7.45(dd, J=8.0, 4.3Hz, 1H), 7.09(br s, 2H), 4.80(t, J=6Hz, 2H), 3.25(q, J=6Hz, 2H), 2.92(t, J=7Hz, 2H), 1.81(m, 4H), 1.58(m, 2H), 1.45(sextet, J=7Hz, 2H), 0.95(t, J=7Hz, 3H) |
| 182 | methyl hexanoate ester linker | (d<sub>6</sub>-DMSO at 29° C.) δ 8.50(dd, J=4.3, 1.5Hz, 1H), 7.90(dd, J=8.0, 1.5Hz, 1H), 7.75(t, J=6Hz, 1H), 7.42(dd, J=8.0, 4.3Hz, 1H), 6.77 (br s, 2H), 4.78(t, J=6Hz, 2H), 3.56(s, 3H), 3.06(q, J=6Hz, 2H), 2.90(t, J=7Hz, 2H), 2.25(m, 2H), 2.00(m, 2H), 1.81(m, 4H), 1.44(m, 8H), 0.96(t, J=7Hz, 3H) |

-continued

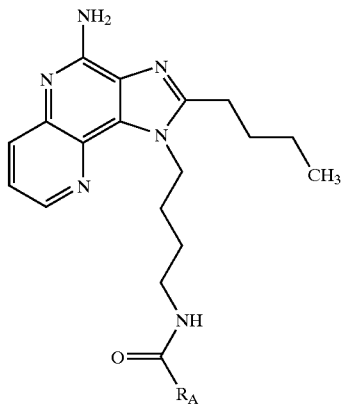

| Example # | R_A Fragment | $^1$H NMR (500 MHz, solvent indicated) |
|---|---|---|
| 183 | 2-chloro-3-pyridyl (Cl on pyridine, attached at 3-position) | (d$_6$-DMSO at 29° C.) δ 8.55(t, J=6Hz, 1H), 8.50(dd, J=4.3, 1.5Hz, 1H), 8.43(dd, J=5, 2Hz, 1H), 7.91(dd, J=8.4, 1.5Hz, 1H), 7.74 (d, J=8.0, 2Hz, 1H), 7.43(dd, J=8, 4.3Hz, 1H), 7.42(dd, J=8, 5Hz, 1H), 6.75(brs, 2H), 4.83(t, J=6Hz, 2H), 3.27(q, J=6Hz, 2H), 2.94(t, J=7Hz, 2H), 1.92(m, 2H), 1.83 (quintet, J=7Hz, 2H), 1.60(m, 2H), 1.46 (sextet, J=7Hz, 2H), 0.95(t, J=7Hz, 3H) |
| 184 | 6-chloro-3-pyridyl methyl | (d$_6$-DMSO at 29° C.) δ 8.77(dd, J=2.5, 0.5Hz, 1H), 8.70(t, J=6Hz, 1H), 8.46(dd, J=4.3, 1.5Hz, 1H), 8.16(dd, J=8, 3Hz, 1H), 7.91(dd, J=8.4, 1.5Hz, 1H), 7.62(dd, J=8, 0.5Hz, 1H), 7.43(dd, J=8.4, 1.5Hz, 1H), 6.76(br s, 2H), 4.81(t, J=6Hz, 2H), 3.31(m, 2H), 2.92 (t, J=7Hz, 2H), 1.89(m, 2H), 1.79(quintet, J=7Hz, 2H), 1.61(quintet, J=7Hz, 2H), 1.40 (sextet, J=7Hz, 2H), 0.91(t, J=7Hz, 3H) |
| 185 | 4-(trifluoromethoxy)phenyl methyl | (d$_6$-DMSO at 29° C.) δ 8.55(t, J=6Hz, 1H), 8.45(dd, J=4.3, 1.5Hz, 1H), 7.90(d, J=8Hz, 2H), 7.89(dd, J=8, 1.5Hz, 1H), 7.43(d, J=8Hz, 2H), 7.39(dd, J=8, 4.3Hz, 1H), 6.74(br s, 2H), 4.81(t, J=6Hz, 2H), 3.30(m, 2H), 2.91(t, J=7Hz, 2H), 1.88(m, 2H), 1.78 (quintet, J=7Hz, 2H), 1.63(m, 2H), 1.34 (sextet, J=7Hz, 2H), 0.89(t, J=7Hz, 3H) |
| 186 | 2,4,6-trichlorophenyl methyl | (d$_6$-DMSO at 29° C.) δ 8.64(t, J=6Hz, 1H), 8.49(dd, J=4.4, 1.5Hz, 1H), 7.90(dd, J=8.5, 1.5Hz, 1H), 7.69(s, 2H), 7.42(dd, J=8.5, 4.3Hz, 1H), 6.74(s, 2H), 4.84(t, J=6Hz, 2H), 3.26(q, J=6Hz, 2H), 2.93(t, J=7Hz, 2H), 1.90(m, 2H), 1.83(quintet, J=7Hz, 2H), 1.60 (m, 2H), 1.46(sextet, J=7Hz, 2H), 0.96(t, J=7Hz, 3H) |
| 187 | 4-methoxyphenyl ethyl | (d$_6$-DMSO at 29° C.) δ 8.49(dd, J=4.3, 1.5Hz, 1H), 7.92(t, J=6Hz, 1H), 7.90(dd, J=8.5, 1.5Hz, 1H), 7.42(dd, J=8.5, 4.3Hz, 1H), 7.07 (d, J=8Hz, 2H), 6.76(d, J=8Hz, 2H), 6.74 (br s, 2H), 4.79(t, J=6Hz, 2H), 3.70(s, 3H), 3.25(s, 2H), 3.08(q, J=6Hz, 2H), 2.89(t, J=7Hz, 2H), 1.80(m, 4H), 1.46(m, 2H), 1.44 (sextet, J=7Hz, 2H), 0.95(t, J=7Hz, 3H) |

-continued

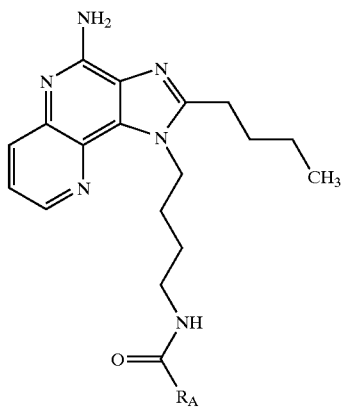

| Example # | R_A Fragment | $^1$H NMR (500 MHz, solvent indicated) |
|---|---|---|
| 188 | ![2-methoxyphenyl] | (d$_6$-DMSO at 29° C.) δ 8.47(dd, J=4.3, 1.5Hz, 1H), 8.15(t, J=6Hz, 1H), 7.90(dd, J=8.4, 1.5Hz, 1H), 7.64(dd, J=8, 2Hz, 1H), 7.41(dt, J=8, 2Hz, 1H), 7.40(dd, J=8.4, 4.3Hz, 1H), 7.06(d, J=8Hz, 1H), 6.98(dt, J=8, 2Hz, 1H), 6.74(s, 2H), 4.82(t, J=6Hz, 2H), 3.70 (s, 3H), 3.33(m, 2H), 2.92(t, J=7Hz, 2H), 1.90(m, 2H), 1.80(quintet, J=7Hz, 2H), 1.60 (m, 2H), 1.43(sextet, J=7Hz, 2H), 0.92(t, J=7Hz, 3H) |
| 189 | ![3-chlorophenyl] | (d$_6$-DMSO at 29° C.) δ 8.56(t, J=6Hz, 1H), 8.46(dd, J=4.4, 1.5Hz, 1H), 7.89(dd, J=8.4, 1.5Hz, 1H), 7.82(t, J=2Hz, 1H), 7.74(td, J=8, 2Hz, 1H), 7.58(td, J=8, 2Hz, 1H), 7.47 (t, J=8Hz, 1H), 7.39(dd, J=8.4, 4.4Hz, 1H), 6.74(s, 2H), 4.81(t, J=6Hz, 2H), 3.31(q, J=6Hz, 2H), 2.91(t, J=7Hz, 2H), 1.88(m, 2H), 1.79(quintet, J=7Hz, 2H), 1.61(m, 2H), 1.36(sextet, J=7Hz, 2H), 0.90(t, J=7Hz, 3H) |
| 190 | ![4-(hexyloxy)phenyl] | (d$_6$-DMSO at 29° C.) δ 8.46(dd, J=4.3, 1.5Hz, 1H), 8.27(t, J=6Hz, 1H), 7.89(dd, J=8.5, 1.5Hz, 1H), 7.75(d, J=8Hz, 2H), 7.40(dd, J=8.5, 4.3Hz, 1H), 6.94(d, J=8Hz, 2H), 6.73(s, 2H), 4.81(t, J=6Hz, 2H), 4.00(t, J=7Hz, 2H), 3.28(q, J=6Hz, 2H), 2.91(t, J=7Hz, 2H), 1.87(m, 2H), 1.78(quintet, J=7Hz, 2H), 1.71(quintet, J=7Hz, 2H), 1.60(m, 2H), 1.38(sextet, J=7Hz, 4H), 1.32(m, 2H), 1.28 (m, 4H), 0.91(t, J=7Hz, 3H), 0.87(t, J=7Hz, 3H) |

EXAMPLES 191–212

Compounds of Formula I

The compounds of Examples 191–212 shown in the table below were prepared according to the following method. 4-(4-Amino-2-butyl-1H-imidazo[4,5-c][1,5]naphthyridin-1-yl)ethaneamine (50 μmol) was dissolved in 5 mL of dichloromethane in a screw-capped test tube and a carboxylic acid (50 μmol) of formula R$^A$COOH was added at ambient temperature. Within 3 minutes a light suspension typically formed. The coupling agent, 1-(3-dimethylaminopropyl)-3-ethyl carbodiimide hydrochloride (~10.5 mg, 55 μmol) was added and the mixture was vortexed at 400 rpm for 1–2 h at ambient temperature, giving a clear solution in most cases. The mixture was applied to a short column (3×1 cm ) of silica gel conditioned with dichloromethane. The product was eluted with 10:1 dichloromethane:methanol, collecting ~2 mL fractions. Thin layer chromatography of the fractions was performed, and fractions with the product spot were pooled and stripped to dryness in a Savant SpeedVac. Purity was checked by reversed phase-HPLC (HPLC conditions refer to using a Hewlett Packard HP 1090 system fitted with a C18 Rainin Microsorb MV column, 4.6×50 mm, particle size=3 microns, pore size=100 Angstroms. Gradient elution: linear gradient from 100% water+0.1% trifluoroacetic acid to 100% acetonitrile+0.1% trifluoroacetic acid over 5 min. at 1 mL per minute. Detection is at 220 nm and 254 nm). APCI-mass spectral data confirmed presence of the expected molecular ion, and proton nmr data supported the expected structure.

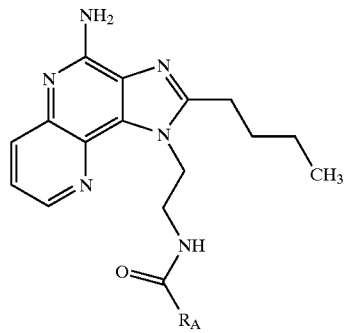

| Example # | R_A Fragment | $^1$H NMR (500 MHz, solvent indicated) |
|---|---|---|
| 191 | 3-ethylthiophene | (CDCl$_3$)δ 8.47(dd, J=4.4, 1.5Hz, 1H), 8.10 (dd, J=8.5, 1.5Hz, 1H), 7.45(dd, J=8.5, 4.4 Hz, 1H), 7.15(dd, J=5.0, 3.0Hz, 1H), 6.75 (d, J=3Hz, 1H), 6.64(dd, J=5.0, 1.2Hz, 1H), 6.61(br t, 1H), 6.3(br s, 2H), 4.94(t, J=6Hz, 2H), 3.30(s, 2H), 2.81(q, J=6Hz, 2H), 2.89(t, J=7Hz, 2H), 1.88(quintet, J=7 Hz, 2H), 1.50(sextet, J=7Hz, 2H), 1.00(t, J=7Hz, 3H) |
| 192 | 2-bromobenzyl | (CDCl$_3$)δ 8.41(dd, J=4.4, 1.5Hz, 1H), 8.04 (dd, J=8.5, 1.5Hz, 1H), 7.40(dd, J=8.5, 4.4 Hz, 1H), 7.34(dd, J=8, 1.2Hz, 1H), 7.07(dt, J=8, 2Hz, 1H), 7.00(dt, J=8, 2Hz, 1H), 6.96(dt, J=8, 2Hz, 1H), 6.78(br t, 1H), 5.72 (br s, 2H), 4.95(t, J=6Hz, 2H), 3.85(q, J=6 Hz, 2H), 3.42(s, 2H), 2.89(t, J=7Hz, 2H), 1.83(quintet, J=7H, 2H), 1.50(sextet, J=7 Hz, 2H), 1.00(t, J=7Hz, 3H) |
| 193 | 2,4-dichlorobenzyl | (CDCl$_3$)δ 8.40(dd, J=4.4, 1.5Hz, 1H), 8.07 (dd, J=8.5, 1.5Hz, 1H), 7.43(dd, J=8.5, 4.5 Hz, 1H), 7.14(d, J=2Hz, 1H), 7.06(br t, 1H), 6.98(dd, J=8, 2Hz, 1H), 6.85(d, J=8 Hz, 1H), 5.75(br s, 2H), 4.96(t, J=6Hz, 2H), 3.86(q, J=6Hz, 2H), 3.31(s, 2H), 2.89 (t, J=7Hz, 2H), 1.89(quintet, J=7Hz, 2H), 1.50(sextet, J=7Hz, 2H), 1.00(t, J=7Hz, 3H) |
| 194 | 4-chlorobutyl | (CDCl$_3$)δ 8.59(dd, J=4.5, 1.8Hz, 1H), 8.09 (dd, J=8.5, 1.8Hz, 1H), 7.47(dd, J=8.5, 4.5 Hz, 1H), 7.19(bt, 1H), 5.79(bs, 2H), 4.96(t, J=6Hz, 2H), 3.82(q, J=6Hz, 2H), 3.36(t, J=6Hz, 2H), 2.92(t, J=7Hz, 2H), 1.91(q, J=7Hz, 2H), 1.87(q, J=7Hz, 2H), 1.50(m, 6H), 1.01(t, J=7Hz, 3H) |
| 195 | 3-(4-nitrophenyl)propyl | (CDCl$_3$)δ 8.51(dd, J=4.5, 1.8Hz, 1H), 8.07 (m, 3H), 7.42(dd, J=4.5, 8.5), 1H), 7.31(br t, 1H), 7.14(d, J=8Hz, 2H), 5.8(s, 2H), 4.95 (t, J=6Hz, 2H), 4.257(t, J=7Hz, 2H), 3.80 (q, J=6Hz, 2H), 2.94(t, J=7Hz, 2H), 1.90 (quintet, J=7Hz, 2H), 1.83(quintet, J=7Hz, 2H), 1.50(sextet, J=7Hz, 2H), 1.34(quintet, J=7Hz, 2H), 1.01(t, J=7Hz, 3H) |
| 196 | 5-nitropentyl | (CDCl$_3$)δ 8.60(dd, J=4.5, 1.5Hz, 1H), 8.11 (dd, J=8.5, 1.5Hz, 1H), 7.49(dd, J=8.5, 4.5 Hz, 1H), 7.24(br s, 1H), 6.0(br s, 2H), 4.95 (t, J=6Hz, 2H), 4.26(t, J=7Hz, 2H), 3.82(q, J=6Hz, 2H), 2.93(t, J=7Hz, 2H), 1.91 (quintet, J=7Hz, 2H), 1.83(m, 4H), 1.50 (sextet, J=7Hz, 2H), 1.35(quintet, J=7Hz, 2H), 1.05(m, 2H), 1.01(t, J=7Hz, 3H) |

-continued

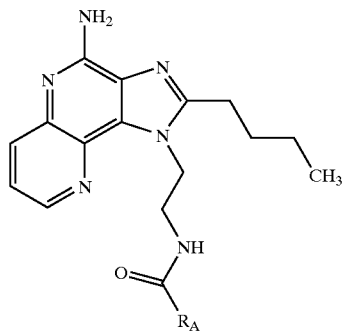

| Example # | R_A Fragment | $^1$H NMR (500 MHz, solvent indicated) |
|---|---|---|
| 197 | 4-(methylthio)benzyl | (CDCl$_3$)δ 8.60(dd, J=4.5, 1.5, 1H), 8.11 (dd, J=8.5, 1.5, 1H), 7.49(dd, J=8.5, 4.5Hz, 1H), 7.01(d, J=8Hz, 2H), 6.76(d, J=8Hz, 2H), 6.59(br s, 1H), 5.69(br s, 2H), 4.93(t, J=6Hz, 2H), 3.80(q, J=6Hz, 2H), 3.20(s, 2H), 2.89(t, J=7Hz, 2H), 2.44(s, 3H), 1.90 (quintet, J=7Hz, 2H), 1.51(sextet, J=7Hz, 2H), 1.01(t, J=7Hz, 3H) |
| 198 | camphor-derived | (CDCl$_3$)δ 8.58(dd, J=4.4, 1.5Hz, 1H), 8.09 (dd, J=8.3, 1.5Hz, 1H), 7.48(dd, J=8.3, 4.4 Hz, 1H), 7.30(br t, 1H), 5.69(br s, 2H), 5.01 (m, 3H), 3.85(q, J=6Hz, 2H), 2.92(t, J=7 Hz, 2H), 1.91(quintet, J=7Hz, 2H), 1.85(m, 1H), 1.79(m, 1H), 1.60(m, 2H), 1.52 (sextet, J=7Hz, 2H), 1.38(d, J=9Hz, 1H), 1.27(t, J=6Hz, 1H), 1.00(t, J=7Hz, 3H) |
| 199 | 4,4,4-trifluorobutyl | (CDCl$_3$)δ 8.59(dd, J=4.5, 1.5Hz, 1H), 8.11 (dd, J=8.5, 1.5Hz, 1H), 7.48(dd, J=8.5, 4.4 Hz, 1H), 7.48(brs, 1H), 6.11(brs, 2H), 4.94(t, J=6Hz, 2H), 3.83(q, J=6Hz, 2H), 2.92(t, J=7Hz, 2H), 2.28(m, 2H), 2.08(t, J=7Hz, 2H), 1.99(quintet, J=7Hz, 2H), 1.52(sextet, J=7Hz, 2H), 1.01(t, J=7Hz, 3H) |
| 200 | 4-chlorophenethyl | (CDCl$_3$)δ 8.54(dd, J=4.4, 1.5Hz, 1H), 8.10 (dd, J=8.4, 1.5Hz, 1H), 7.46(dd, J=8.4, 4.4 Hz, 1H), 7.19(br t, 1H), 7.12(d, J=8Hz, 2H), 6.88(d, J=8Hz, 2H), 5.94(br s, 2H), 4.91(t, J=6Hz, 2H), 3.78(q, J=6Hz, 2H), 2.90(t, J=7Hz, 2H), 2.65(t, J=7Hz, 2H), 2.12(t, J=7Hz, 2H), 1.86(quintet, J=7Hz, 2H), 1.52(sextet, J=7Hz, 2H), 1.02(t, J=7 Hz, 3H) |
| 201 | long-chain alkyl CH$_3$ | (CDCl$_3$)δ 8.60(dd, J=4.4, 1.5Hz, 1H), 8.12 (dd, J=8, 1.5Hz, 1H), 7.47(dd, J=8.0, 4.4 Hz, 1H), 6.86(br s, 1H), 6.20(br s, 2H), 4.96(t, J=6Hz, 2H), 3.81(q, J=6Hz, 2H), 2.92(t, J=7Hz, 2H), 1.90(m, 4H), 1.51 (sextet, J=7Hz, 2H), 1.33(quintet, J=7Hz, 2H), 1.23(m, 16H), 1.01(t, J=7Hz, 3H), 0.87(t, J=7Hz, 3H) |
| 202 | N-ethyl t-butyl carbamate | (CDCl$_3$)δ 8.58(dd, J=4.3, 1.5Hz, 1H), 8.04 (dd, J=8.0, 1.5Hz, 1H), 7.56(br s, 1H), 7.43 (dd, J=8.0, 4.3Hz, 1H), 5.84(br s, 2H), 4.94 (t, J=6Hz, 2H), 4.89(br s, 1H), 3.85(q, J=6 Hz, 2H), 3.54(d, J=6Hz, 2H), 2.92(t, J=7 Hz, 2H), 1.89(quintet, J=7Hz, 2H), 1.51 (sextet, J=7Hz, 2H), 1.41(s, 9H), 1.00(t, J=7Hz, 3H) |

-continued

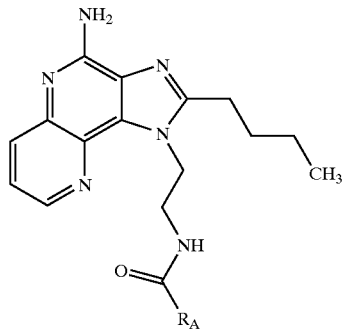

| Example # | R_A Fragment | $^1$H NMR (500 MHz, solvent indicated) |
|---|---|---|
| 203 | H₃C—CH(CH₃)—NH—C(=O)—O—C(CH₃)₃ | (CDCl₃)δ 8.60(d, J=4.4Hz, 1H), 8.07(dd, J=8.0, 1.5Hz, 1H), 7.59(br s, 1H), 7.45(dd, J=8.5, 4.4Hz, 1H), 5.88(br s, 2H), 4.94(m, 2H), 4.77(s, 1H), 3.93(m, 1H), 3.84(m, 2H), 2.94(t, J=7Hz, 2H), 1.89(quintet, J=7 Hz, 2H), 1.52(sextet, J=7Hz, 2H), 1.40(s, 9H), 1.01(d, J=7Hz, 3H), 0.99(t, J=7Hz, 3H) |
| 204 | 5-bromo-2-methylthiophene | (d₆-DMSO at 80° C.)δ 8.53(dd, J=4.4, 1.5 Hz, 1H), 8.53(t, J=6Hz, 1H), 7.96(dd, J=8.3, 1.5Hz, 1H), 7.45(dd, J=8.3, 4.4Hz, 1H), 7.32(d, J=4Hz, 1H), 7.16(d, J=4Hz, 1H), 6.81(br s, 2H), 4.91(t, J=6Hz, 2H), 3.78(q, J=6Hz, 2H), 2.85(t, J=7Hz, 2H), 1.77(quintet, J=7Hz, 2H), 1.37(sextet,J=7 Hz, 2H), 0.87(t, J=7Hz, 3H) |
| 205 | 2,5-dimethylpyrazine | (CDCl₃)δ 9.16(d, J=1.4Hz, 1H), 8.66(dd, J=4.4, 1.5Hz, 1H), 8.44(t, J=6Hz, 1H), 8.11(d, J=1.4Hz, 1H), 8.09(dd, J=8.4, 1.5 Hz, 1H), 7.47(dd, J=8.5, 4.4Hz, 1H), 6.10 (br s, 2H), 5.11(t, J=6Hz, 2H), 4.05(q, J=6 Hz, 2H), 2.92(t, J=7Hz, 2H), 2.59(s, 3H), 1.87(quintet, J=7Hz, 2H), 1.46(sextet, J=7 Hz, 2H), 0.95(t, J=7Hz, 3H) |
| 206 | 3-bromo-5-methylfuran | (CDCl₃)δ 8.73(dd, J=4.4, 1.5Hz, 1H), 8.12 (dd, J=8.4, 1.5Hz, 1H), 7.95(br s, 1H), 7.52 (dd, J=8.4, 4.4Hz, 1H), 6.91(d, J=3.4Hz, 1H), 6.31(d, J=3.4Hz, 1H), 6.04(br s, 2H), 5.07(t, J=6Hz, 2H), 3.99(q, J=6Hz, 2H), 2.93(t, J=7Hz, 2H), 1.91(quintet, J=7Hz, 2H), 1.50(sextet, J=7Hz, 2H), 0.99(t, J=7 Hz, 3H) |
| 207 | 3-ethylpyridine | (CDCl₃)δ 8.50(dd, J=4.4, 1.5Hz, 1H), 8.42 (d, J=4Hz, 1H), 8.19(d, J=1.5Hz, 1H), 8.09 (dd, J=8.2, 1.5Hz, 1H), 7.47(dd, J=8.3, 4.4 Hz, 1H), 7.26(br s, 1H), 7.23(d, J=8Hz, 1H), 7.07(dd, J=8.5, 5Hz, 1H), 6.06(br s, 2H), 3.95(t, J=6Hz, 2H), 3.84(q, J=6Hz 2H), 3.21(s, 2H), 2.87(t, J=7Hz, 2H),1.88 (quintet, J=7Hz, 2H), 1.50(sextet, J=7Hz, 2H), 1.00(t, J=7Hz, 3H) |

-continued

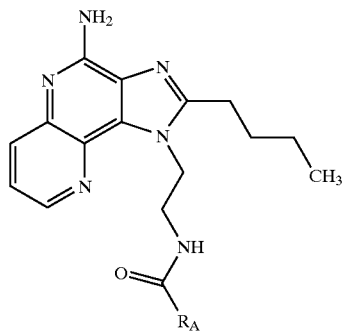

| Example # | R_A Fragment | $^1$H NMR (500 MHz, solvent indicated) |
|---|---|---|
| 208 | 3-pyridyl-CH2CH2- | (CDCl$_3$)δ 8.54(dd, J=4.4, 1.5Hz, 1H), 8.37 (d, J=4Hz, 1H), 8.24(br s, 1H), 8.09(dd, J=8.5, 1.5Hz, 1H), 7.46(dd, J=8.5, 4.4Hz, 1H), 7.35(br t, 1H), 7.27(td, J=8, 2Hz, 1H), 7.08(dd, J=8, 5Hz, 1H), 5.98(br s, 2H), 4.91(t, J=6Hz, 2H), 3.79(q, J=6Hz, 2H), 2.90(t, J=7Hz, 2H), 2.69(t, J=7Hz, 2H), 2.14(t, J=7Hz, 2H), 1.90(quintet, J=7Hz, 2H), 1.52(sextet, J=7Hz, 2H), 1.01(t, J=7 Hz, 3H) |
| 209 | 2-methyl-4-nitro-1-propylimidazol-5-yl | (d$_6$-DMSO)δ 8.52(d, J=8.3Hz, 1H), 8.37 (m, 2H), 7.96(d, J=8.3Hz, 1H), 7.48(dd, J=8.3, 4.5Hz, 1H), 7.14(br s, 2H), 4.72(t, J=6Hz, 2H), 4.12(t, J=6Hz, 2H), 3.56(q, J=6Hz, 2H), 2.81(t, J=7Hz, 2H), 2.52(m, 2H), 2.33(s, 3H), 1.75(quintet, J=7Hz, 2H), 1.40(sextet, J=7Hz, 2H), 0.94(t, J=7Hz, 3H) |
| 210 | 1-(4-chlorobenzyl)-4-methyl-2-pyrrolidinone | (CDCl$_3$)δ 8.52(dd, J=4.4, 1.5Hz, 1H), 8.05 (dd, J=8.4, 1.5Hz, 1H), 7.76(t, J=6Hz, 1H), 7.43(dd, J=8.5, 4.4Hz, 1H), 7.27(d, J=8 Hz, 2H), 7.06(d, J=8Hz, 2H), 5.82(br s, 2H), 5.06 & 4.83(m, 2H), 3.88 & 3.79(m, 2H), 3.03(m, 1H), 2.89(t, J=7Hz, 2H), 2.79 (m, 1H), 2.5(m, 3H), 2.25(m, 1H), 1.90 (quintet, J=7Hz, 2H), 1.51(sextet, J=7Hz, 2H), 1.00(t, J=7Hz, 3H) |
| 211 | N-propylphthalimide | (d$_6$-DMSO)δ 8.53(dd, J=4.4, 1.5Hz, 1H), 8.24(t, J=6Hz, 1H), 7.96(dd, J=8.4, 1.5Hz, 1H), 7.84(m, 4H), 7.48(dd, J=4.4, 8.4Hz, 1H), 7.18(br s, 2H), 4.75(t, J=6Hz, 2H), 3.73(t, J=7Hz, 2H), 3.52(q, J=6Hz, 2H), 2.86(t, J=7Hz, 2H), 2.34(t, J=7Hz, 2H), 1.79(quintet, J=7Hz, 2H), 1.40(sextet, J=7 Hz, 2H), 0.92(t, J=7Hz, 3H) |

-continued

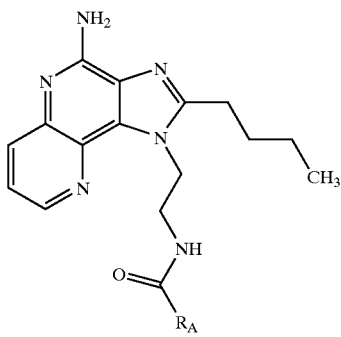

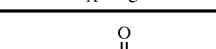

| Example # | R$_A$ Fragment | $^1$H NMR (500 MHz, solvent indicated) |
|---|---|---|
| 212 | (thiophene butyryl structure) | (CDCl$_3$)δ 8.60(dd, J=4.4, 1.5Hz, 1H), 8.04 (dd, J=8.5, 1.5Hz, 1H), 7.68(dd, J=3.5, 1.2 Hz, 1H), 7.61(dd, J=3.5, 1.2Hz, 1H), 7.43 (dd, J=8.5, 4.4Hz, 1H), 7.39(t, J=6Hz, 1H), 7.10(dd, J=5, 3.5Hz, 1H), 5.79(br s, 2H), 4.93(t, J=6Hz, 2H), 3.82(q, J=6Hz, 2H), 3.12(t, J=7Hz, 2H), 2.92(t, J=7Hz, 2H), 2.32(t, J=7Hz, 2H), 1.89(quintet, J=7Hz, 2H), 1.49(sextet, J=7Hz, 2H), 0.99(t, J=7 Hz, 3H) |

EXAMPLE 213

Compound of formula II

N-[2-(4-Amino-2-butyl-1H-imidazo[4,5-c][1,5] naphthyridin-1-yl)ethyl]-5-oxo-2-pyrrolinecarboxamide

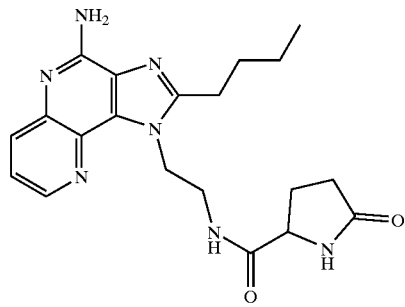

Using the general method of Example 97 L-pyroglutamic acid (0.23 g, 1.7 mmole) was reacted with 2-(4-amino-2-butyl-1H-imidazo[4,5-c][1,5]naphthyridin-1-yl) ethaneamine (0.5 g, 1.7 mmole) to provide 0.10 g of N-[2-(4-amino-2-butyl-1H-imidazo[4,5-c][1,5] naphthyridin-1-yl)ethyl]-5-oxo-2-pyrrolinecarboxamide as a white powder, m.p. 135–138° C. Analysis: Calculated for C$_{20}$H$_{25}$N$_7$O$_2$·½CH$_3$CN: %C, 60.63; %H, 6.42; %N, 25.25; Found: %C, 60.14; %H, 6.41; %N, 25.20. HRMS (EI) calcd for C$_{20}$H$_{25}$N$_7$O$_2$(M+) 396.2103 found 396.2112

TEST METHODS

Cytokine Induction in Human Cells

An in vitro human blood cell system was used to assess cytokine induction by compounds of the invention. Activity is based on the measurement of interferon and tumor necrosis factor (α) (IFN and TNF, respectively) secreted into culture media as described by Testerman et. al. In "Cytokine Induction by the Immunomodulators Imiquimod and S-27609", *Journal of Leukocyte Biology*, 58, 365–372 (September, 1995).

Blood Cell Preparation for Culture

Whole blood is collected by venipuncture into EDTA vacutainer tubes from healthy human donors. Peripheral blood mononuclear cells (PBMCs) are separated from whole blood by Histopaqueg®-1077 (Sigma Chemicals, St. Louis, Mo.) density gradient centrifugation. The PBMCs are suspended at 1.5–2×10$^6$ cells/mL in RPMI 1640 medium containing 10% fetal bovine serum, 2 mM L-glutamine and 1% penicillin/streptomycin solution (RPMI complete). 1 mL portions of PBMC suspension are added to 24 well flat bottom sterile tissue culture plates.

Compound Preparation

The compounds are solubilized in dimethyl sulfoxide (DMSO). The DMSO concentration should not exceed a final concentration of 1% for addition to the culture wells. The compounds are generally tested in a concentration range of from 0.1 to 100 μM.

Incubation

The solution of test compound is added to the wells containing 1 mL of PBMCs in media. The plates are covered with plastic lids, mixed gently and then incubated for 18 to 24 hours at 37° C. with a 5% carbon dioxide atmosphere.

Separation

Following incubation the plates are centrifuged for 5–10 minutes at 1000 rpm (~200×g) at 4° C. The cell culture supernatant is removed with a sterile polypropylene pipet and transferred to a 2 mL sterile cryotube. Samples are maintained at −70° C. until analysis.

Interferon Analysis/Calculation

Interferon is determined by bioassay using A549 human lung carcinoma cells challenged with encephalomyocarditis.

The details of the bioassay method have been described by G. L. Brennan and L. H. Kronenberg in "Automated Bioassay of Interferons in Micro-test Plates", Biotechniques, Jun./Jul., 78, 1983, incorporated herein by reference. Briefly stated the method is as follows: A549 cells are incubated with samples and standard interferon dilutions at 37° C. for 24 hours. The incubated cells are then infected with an inoculum of encephalomyocarditis virus. The infected cells are incubated for an additional 24 hours at 37° C. before quantifying for viral cytopathic effect. The viral cytopathic effect is quantified by staining followed by visual scoring of the plates. Results are expressed as alpha reference units/mL based on the value obtained for NIH Human Leukocyte IFN standard.

Tumor Necrosis Factor(α) Analysis

Tumor necrosis factor (α) (TNF)concentration is determined using an ELISA kit available from Genzyme, Cambridge, Mass. The results are expressed as pg/mL.

In the table below, a "+" indicates that the compound induced the indicated cytokine at that particular concentration, a "−" indicates that the compound did not induce the indicated cytokine at that particular concentration, and a "±" indicates that the results were equivocal at that particular concentration.

| | Cytokine Induction in Human Cells | | | | | | | |
|---|---|---|---|---|---|---|---|---|
| | IFN Dose Concentration ($\mu$M) | | | | TNF Dose Concentration ($\mu$M) | | | |
| Example | 0.1 | 1.0 | 10.0 | 100.0 | 0.1 | 1.0 | 10.0 | 100.0 |
| 9 | ± | − | + | − | − | − | − | − |
| 10 | + | + | + | + | − | − | − | + |
| 12 | Not run | + | + | + | Not run | + | + | + |
| 13 | Not run | + | + | + | Not run | + | + | + |
| 22 | Not run | − | − | − | Not run | − | ± | + |
| 23 | Not run | + | + | − | Not run | − | ± | − |
| 25 | Not run | − | + | + | Not run | − | ± | − |
| 26 | Not run | + | − | + | Not run | + | ± | − |
| 27 | Not run | + | + | + | Not run | + | + | + |
| 28 | Not run | + | + | + | Not run | − | + | + |
| 32 | Not run | + | + | + | Not run | − | − | − |
| 33 | Not run | + | + | + | Not run | − | − | − |
| 36 | Not run | + | + | + | Not run | − | + | − |
| 39 | Not run | + | + | − | Not run | + | + | − |
| 40 | Not run | + | + | ± | Not run | + | + | + |
| 45 | + | + | + | − | − | + | + | − |
| 46 | + | + | + | + | + | + | + | + |
| 46 | Not run | + | + | ± | Not run | + | + | + |
| 47 | − | + | + | ± | − | + | + | + |
| 48 | + | + | + | − | − | + | + | − |
| 49 | + | + | + | + | − | + | + | + |
| 50 | Not run | + | + | − | Not run | + | + | − |
| 51 | Not run | + | + | + | Not run | + | + | − |
| 52 | Not run | + | + | − | Not run | + | + | − |
| 53 | + | + | + | + | − | + | + | + |
| 54 | Not run | + | + | + | Not run | + | + | + |
| 55 | Not run | + | + | + | Not run | + | + | − |
| 56 | − | + | + | − | − | − | − | − |
| 57 | − | + | + | + | − | − | + | + |
| 58 | + | + | + | − | − | + | + | − |
| 62 | + | + | + | + | + | + | + | + |
| 65 | + | + | + | + | − | + | + | + |
| 70 | + | + | + | + | − | + | + | − |
| 75 | − | + | + | + | − | − | + | − |
| 80 | − | + | + | − | − | − | + | − |
| 85 | + | + | + | − | − | + | + | − |
| 90 | ± | + | + | + | − | − | + | + |
| 91 | + | + | + | + | + | + | + | + |

-continued

| | Cytokine Induction in Human Cells | | | | | | | |
|---|---|---|---|---|---|---|---|---|
| | IFN Dose Concentration ($\mu$M) | | | | TNF Dose Concentration ($\mu$M) | | | |
| Example | 0.1 | 1.0 | 10.0 | 100.0 | 0.1 | 1.0 | 10.0 | 100.0 |
| 92 | ± | + | + | + | − | + | + | + |
| 93 | − | + | + | + | − | + | + | + |
| 94 | − | + | + | + | − | + | + | + |
| 95 | ± | + | + | + | − | − | + | + |
| 96 | − | ± | + | + | − | − | + | + |
| 97 | − | − | + | + | − | − | + | + |
| 98 | − | + | + | + | − | + | + | + |
| 99 | − | + | + | + | − | − | + | + |
| 100 | − | − | + | + | − | − | + | + |
| 101 | − | − | + | + | − | − | + | + |
| 101 | − | − | + | + | − | − | − | + |
| 102 | + | + | + | + | + | + | + | + |
| 103 | − | − | + | + | − | − | + | + |
| 104 | − | + | + | − | − | − | + | − |
| 105 | + | + | + | + | − | − | + | + |
| 106 | + | + | + | − | − | + | + | − |
| 107 | + | + | + | − | − | + | + | − |
| 108 | + | + | + | + | ± | − | + | + |
| 109 | + | + | + | + | − | ± | + | + |
| 110 | + | + | + | + | − | + | + | + |
| 111 | − | − | + | + | − | − | + | + |
| 112 | + | + | + | ± | + | + | − | − |
| 113 | − | + | + | + | − | + | + | + |
| 114 | − | − | + | + | − | − | + | + |
| 115 | − | − | + | + | − | − | + | + |
| 116 | − | + | + | + | − | + | + | + |
| 117 | − | − | + | + | − | − | + | + |
| 118 | Not run | − | + | + | Not run | − | + | + |
| 119 | Not run | − | − | − | Not run | − | − | − |
| 120 | Not run | + | + | + | Not run | − | + | + |
| 121 | Not run | + | + | + | Not run | + | + | + |
| 122 | Not run | − | + | + | Not run | − | + | + |
| 123 | Not run | ± | − | − | Not run | − | ± | − |
| 124 | Not run | + | + | + | Not run | − | + | + |
| 125 | Not run | + | + | + | Not run | − | + | + |
| 126 | Not run | + | + | + | Not run | − | + | + |
| 127 | Not run | + | + | + | Not run | − | + | + |
| 128 | Not run | ± | + | + | Not run | − | ± | + |
| 129 | Not run | + | + | + | Not run | + | + | + |
| 130 | Not run | + | + | + | Not run | + | + | + |
| 131 | Not run | + | + | + | Not run | + | + | + |
| 132 | Not run | + | + | + | Not run | + | + | + |
| 133 | Not run | + | + | + | Not run | + | + | + |
| 134 | Not run | + | + | + | Not run | + | + | + |
| 135 | Not run | − | + | + | Not run | − | + | + |
| 136 | Not run | + | + | + | Not run | − | + | + |
| 137 | Not run | + | + | + | Not run | − | ± | + |
| 138 | Not run | + | + | + | Not run | + | + | + |
| 139 | Not run | + | + | + | Not run | − | + | + |
| 140 | Not run | + | + | + | Not run | + | + | + |
| 141 | Not run | + | + | + | Not run | − | + | + |
| 142 | Not run | + | + | + | Not run | − | + | + |
| 143 | Not run | − | + | + | Not run | − | ± | − |
| 144 | + | + | + | + | − | + | + | + |
| 145 | − | − | + | + | − | + | + | + |
| 146 | + | + | + | − | + | + | + | + |
| 147 | ± | + | + | + | − | − | + | + |
| 148 | − | + | + | + | − | − | + | + |
| 149 | − | − | − | − | − | − | − | − |
| 150 | − | − | + | + | − | − | + | + |
| 151 | − | − | + | − | − | − | + | − |
| 152 | − | − | + | + | − | − | + | + |
| 153 | − | + | + | − | − | + | + | − |
| 155 | − | + | + | − | − | − | + | − |
| 156 | + | + | + | + | − | + | + | − |
| 157 | + | + | + | − | − | − | + | − |
| 158 | − | + | + | − | − | − | + | − |
| 159 | + | + | + | − | + | + | + | + |
| 160 | + | + | + | − | − | + | + | − |
| 161 | ± | + | + | + | − | − | + | + |
| 162 | + | + | + | + | − | + | + | + |
| 163 | + | + | + | + | − | + | + | − |

Cytokine Induction in Human Cells

| Example | IFN Dose Concentration (μM) | | | | TNF Dose Concentration (μM) | | | |
|---|---|---|---|---|---|---|---|---|
| | 0.1 | 1.0 | 10.0 | 100.0 | 0.1 | 1.0 | 10.0 | 100.0 |
| 164 | + | + | + | − | − | + | + | − |
| 165 | + | + | + | + | − | + | + | + |
| 166 | − | + | + | − | − | + | + | − |
| 167 | − | + | + | − | − | − | + | − |
| 168 | − | + | + | + | − | + | + | − |
| 169 | − | + | + | + | − | − | + | + |
| 170 | − | + | + | + | − | − | + | + |
| 171 | + | + | + | ± | − | + | + | − |
| 172 | + | + | + | + | − | + | + | + |
| 173 | + | + | + | + | − | + | + | + |
| 174 | + | + | + | + | + | + | + | − |
| 175 | − | + | + | − | − | + | + | − |
| 176 | − | + | + | + | − | − | + | + |
| 177 | − | − | + | − | − | − | + | − |
| 178 | + | + | + | + | + | − | + | − |
| 179 | − | + | + | + | − | + | + | − |
| 180 | + | + | + | + | ± | + | + | + |
| 181 | − | − | ± | + | − | − | − | + |
| 182 | − | + | + | + | − | + | + | − |
| 183 | − | − | − | − | − | − | − | − |
| 183 | | | | | + | + | + | − |
| 184 | + | + | + | − | + | + | + | − |
| 185 | − | + | + | ± | − | ± | + | − |
| 186 | + | + | + | + | − | + | + | + |
| 187 | − | + | + | + | − | + | + | − |
| 188 | + | + | + | − | − | + | + | − |
| 189 | − | + | + | − | − | ± | + | − |
| 190 | + | + | + | − | − | + | + | − |
| 191 | Not run | + | + | + | Not run | − | + | + |
| 192 | − | − | + | + | − | − | + | + |
| 193 | − | − | + | + | − | − | + | + |
| 194 | − | + | + | + | − | + | + | + |
| 195 | − | − | + | − | − | + | + | + |
| 196 | − | − | + | + | − | − | + | + |
| 197 | − | − | + | + | − | − | + | + |
| 198 | − | − | + | + | − | + | + | + |
| 199 | + | − | + | + | − | − | + | + |
| 200 | − | − | + | + | − | − | + | + |
| 201 | − | − | − | − | − | − | − | + |
| 202 | − | − | + | + | − | − | + | + |
| 203 | − | − | + | + | − | − | + | + |
| 204 | + | + | + | + | − | + | + | + |
| 205 | + | + | + | + | − | + | + | + |
| 206 | + | + | + | + | − | + | + | + |
| 207 | − | − | + | + | − | − | + | + |
| 208 | − | − | + | + | − | − | − | − |
| 208 | | | | | − | ± | + | + |
| 209 | − | − | + | + | − | − | + | + |
| 210 | − | − | + | + | + | + | + | + |
| 211 | − | − | + | + | − | − | + | + |
| 212 | − | + | + | + | − | + | + | + |

Interferon (α) Induction in Human Cells

An in vitro human blood cell system was used to assess interferon induction by compounds of the invention. Activity is based on the measurement of interferon secreted into culture media. Interferon is measured by bioassay.

Blood Cell Preparation for Culture

Whole blood was collected by venipuncture into EDTA vacutainer tubes. Peripheral blood mononuclear cells (PBM's) were separated from whole blood by using either LeucoPREP™ Brand Cell Separation Tubes (available from Becton Dickinson) or Ficoll-Paque® solution (available from Pharmacia LKB Biotechnology Inc, Piscataway, N.J.). The PBM's were suspended at $1 \times 10^6$/mL in RPMI 1640 media (available from GIBCO, Grand Island, N.Y.) containing 25 mM HEPES (N-2-hydroxyethylpiperazine-N'-2-ethanesulfonic acid) and L-glutamine (1% penicillin-streptomycin solution added) with 10% heat inactivated (56° C. for 30 minutes) autologous serum added. 200 μL portions of PBM suspension were added to 96 well (flat bottom) MicroTest III sterile tissue culture plates.

Compound Preparation

The compounds were solubilized in ethanol, dimethyl sulfoxide or tissue culture water then diluted with tissue culture water, 0.01N sodium hydroxide or 0.01N hydrochloric acid (The choice of solvent will depend on the chemical characteristics of the compound being tested.). Ethanol or DMSO concentration should not exceed a final concentration of 1% for addition to the culture wells. Compounds were initially tested in a concentration range of from about 0.1 μg/mL to about 5 μg/mL. Compounds which show induction at a concentration of 0.5 μg/mL were then tested in a wider concentration range.

Incubation

The solution of test compound was added in a volume (less than or equal to 50 μL) to the wells containing 200 μL of diluted whole blood or of PBM's in media. Solvent and/or media was added to control wells (wells with no test compound) and as needed to adjust the final volume of each well to 250 μL. The plates were covered with plastic lids, vortexed gently and then incubated for 48 hours at 37° C. with a 5% carbon dioxide atmosphere.

Separation

Followin, incubation, the plates were covered with parafilm and then centrifuaed at 1000 rpm for 10 to 15 minutes at 4° C. in a Damon IEC Model CRU-5000 centrifuge. Media (about 200 μL) was removed from 4 to 8 wells and pooled into 2 mL sterile freezing vials. Samples were maintained at −70° C. until analysis.

Interferon Analvsiss/Calculation

Interferon was determined by bioassay using A549 human lung carcinoma cells challenged with encephalomyocarditis. The details of the bioassay method have been described by G. L. Brennan and L. H. Kronenberg in "Automated Bioassay of Interferons in Micro-test Plates", *Biotechniques*, Jun./Jul., 78, 1983, incorporated herein by reference. Briefly stated the method is as follows: interferon dilutions and A549 cells are incubated at 37° C. for 12 to 24 hours. The incubated cells are infected with an inoculum of encephalomyocarditis virus. The infected cells are incubated for an additional period at 37° C. before quantizing for viral cytopathic effect. The viral cytopathic effect is quantified by staining followed by spectrophotometric absorbance measurements. Results are expressed as alpha reference units/mL based on the value obtained for NIH HU IF-L standard. The interferon was identified as essentially all interferon alpha by testing in checkerboard neutralization assays against rabbit anti-human interferon (beta) and goat anti-human interferon (alpha) using A549 cell monolayers challenged with encephalomyocarditis virus.

In the table below, a "+" indicates that the compound induced interferon ct at that particular concentration, a "−" indicates that the compound did not induce interferon α at that particular concentration, and a "±" indicates that the results were equivocal at that particular concentration.

Interferon (α) Induction in Human Cells

| Example | Dose Concentration (μg/mL) | | | | | | | | |
|---|---|---|---|---|---|---|---|---|---|
| | 0.01 | 0.05 | 0.10 | 0.50 | 1.0 | 5.0 | 10.0 | 25.0 | 50.0 |
| 9 | − | − | − | − | − | − | − | − | − |
| 10 | − | − | − | − | + | + | + | + | + |
| 12 | − | − | + | + | + | + | + | + | + |
| 13 | − | + | + | + | + | + | + | + | + |
| 22 | not run | not run | not run | not run | − | − | − | + | not run |
| 23 | not run | not run | not run | not run | − | − | − | − | not run |
| 25 | − | − | − | − | − | + | + | + | not run |
| 26 | − | − | − | − | − | ± | + | + | not run |
| 27 | − | − | + | + | + | + | + | + | not run |
| 28 | − | ± | + | + | + | + | + | + | not run |
| 32 | − | − | − | − | + | + | + | + | + |
| 33 | − | − | − | − | − | + | + | + | + |
| 36 | − | + | + | + | + | + | + | + | + |
| 39 | − | − | + | + | + | + | + | + | + |
| 40 | − | + | + | + | + | + | + | + | + |

The present invention has been described with reference to several embodiments thereof. The foregoing detailed description and examples have been provided for clarity of understanding only, and no unnecessary limitations are to be understood therefrom. It will be apparent to those skilled in the art that many changes can be made to the described embodiments without departing from the spirit and scope of the invention. Thus, the scope of the invention should not be limited to the exact details of the compositions and structures described herein, but rather by the language of the claims that follow.

What is claimed is:

1. A compound of the formula II:

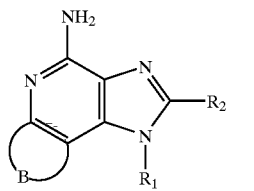

II wherein

B is —NR—C(R)$_2$—C(R)$_2$—C(R)$_2$—; —C(R)$_2$—NR—C(R)$_2$—C(R)$_2$—; —C(R)$_2$—C(R)$_2$—NR—C(R)$_2$— or —C(R)$_2$—C(R)$_2$—C(R)$_2$—NR—;

$R_1$ is selected from the group consisting of:
-hydrogen;
—$C_{1-20}$ alkyl or $C_{2-20}$ alkenyl that is unsubstituted or substituted by one or more substituents selected from the group consisting of:
-aryl;
-heteroaryl;
-heterocyclyl;
—O—$C_{1-20}$ alkyl,
—O—($C_{1-20}$ alkyl)$_{0-1}$-aryl;
—O—($C_{1-20}$ alkyl)$_{0-1}$-heteroaryl;
—O—($C_{1-20}$ alkyl)$_{0-1}$-heterocyclyl;
—$C_{1-20}$ alkoxycarbonyl;
—S(O)$_{0-2}$—$C_{1-20}$ alkyl;
—S(O)$_{0-2}$—($C_{1-20}$ alkyl)$_{0-1}$-aryl;
—S(O)$_{0-2}$—($C_{1-20}$ alkyl)$_{0-1}$-heteroaryl;
—S(O)$_{0-2}$—($C_{1-20}$ alkyl)$_{0-1}$heterocyclyl;
—N(R$_3$)$_2$;
—N$_3$;
oxo;
-halogen;
—NO$_2$;
—OH; and
—SH; and
—$C_{1-20}$ alkyl-NR$_3$—Q—X—R$_4$ or —$C_{2-20}$ alkenyl-NR$_3$—CO—X—R$_4$ wherein Q is —CO— or —SO$_2$—; X is a bond, —O— or —NR$_3$— and R$_4$ is aryl; heteroaryl; heterocyclyl; or —$C_{1-20}$ alkyl or $C_{2-20}$ alkenyl that is unsubstituted or substituted by one or more substituents selected from the group consisting of:
-aryl;
-heteroaryl;
-heterocyclyl;
—O—$C_{1-20}$ alkyl,
—O—($C_{1-20}$ alkyl)$_{0-1}$-aryl;
—O—($C_{1-20}$ alkyl)$_{0-1}$-heteroaryl;
—O—($C_{1-20}$ alkyl)$_{0-1}$-heterocyclyl;
—$C_{1-20}$ alkoxycarbonyl;
—S(O)$_{0-2}$—$C_{1-20}$ alkyl;
—S(O)$_{0-2}$—($C_{1-20}$ alkyl)$_{0-1}$-aryl;
—S(O)$_{0-2}$—($C_{1-20}$ alkyl)$_{0-1}$-heteroaryl;
—S(O)$_{0-2}$—($C_{1-20}$ alkyl)$_{0-1}$-heterocyclyl;
—N(R$_3$)$_2$;
—NR$_3$—CO—O—$C_{1-20}$ alkyl;
—N$_3$;
oxo;
-halogen;
—NO$_2$;
—OH; and —SH; or R$_4$ is

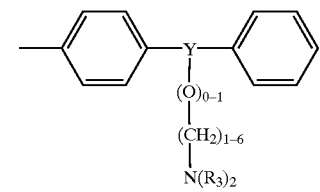

wherein Y is —N— or —CR—;
$R_2$ is selected from the group consisting of:
-hydrogen;
—$C_{1-10}$ alkyl;

—$C_{1-10}$ alkenyl;
-aryl;
—$C_{1-10}$ alkyl—O—$C_{1-10}$-alkyl;
—$C_{1-10}$ alkyl—O—$C_{2-10}$ alkenyl; and
—$C_{1-10}$ alkyl or $C_{2-10}$ alkenyl substituted by one or more substituents selected from the group consisting of:
—OH;
-halogen;
—$N(R_3)_2$;
—CO—$N(R_3)_2$;
—CO—$C_{1-10}$ alkyl;
—$N_3$;
-aryl;
-heteroaryl;
-heterocyclyl;
—CO-aryl; and
—CO-heteroaryl;

each $R_3$ is independently selected from the group consisting of hydrogen and $C_{1-10}$ alkyl; and each R is independently selected from the group consisting of hydrogen, $C_{1-10}$ alkyl, $C_{1-10}$ alkoxy, halogen and trifluoromethyl, or a pharmaceutically acceptable salt thereof.

2. A compound according to claim 1 wherein $R_1$ is selected from the group consisting of $C_{1-6}$ alkyl and $C_{1-6}$ hydroxyalkyl.

3. A compound according to claim 2 wherein $R_1$ is selected from the group consisting of n-butyl, 2-hydroxy-2-methylpropyl, and 2-methylpropyl.

4. A compound according to claim 1 wherein $R_2$ is selected from the group consisting of methyl, n-butyl, benzyl, ethoxymethyl, and methoxyethyl.

5. A compound according to claim 1 wherein each R is hydrogen.

6. A pharmaceutical composition comprising a pharmaceutically effective amount of a compound according to claim 1 and a pharmaceutically acceptable carrier.

7. A method of inducing cytokine biosynthesis in an animal comprising administering an effective amount of a compound according to claim 1 to the animal.

8. A method of treating a viral infection in an animal comprising administering an effective amount of a compounds according to claim 1 to the animal.

9. A compound of the formula I:

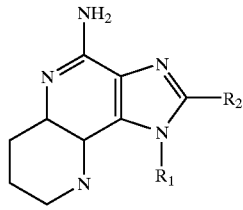

wherein
$R_1$ is selected from the group consisting of:
-hydrogen;
—$C_{1-20}$ alkyl or $C_{2-20}$ alkenyl that is unsubstituted or substituted by one or more substituents selected from the group consisting of:
-aryl;
—O—$C_{1-20}$ alkyl,
—O—($C_{1-20}$ alkyl)$_{0-1}$-aryl;
—$C_{1-20}$ alkoxycarbonyl;
—$S(O)_{0-2}$—$C_{1-20}$ alkyl;
—$S(O)_{0-2}$—($C_{1-20}$ alkyl)$_{0-1}$-aryl;
—$N(R_3)_2$;
—$N_3$;
oxo;
-halogen;
—$NO_2$;
—OH; and
—SH; and
—$C_{1-20}$ alkyl-$NR_3$—Q—X—$R_4$ or —$C_{2-20}$ alkenyl-$NR_3$—Q—X—$R_4$ wherein Q is —CO— or —$SO_2$—; X is a bond, —O— or —$NR_3$— and $R_4$ is aryl; or —$C_{1-20}$ alkyl or $C_{2-20}$ alkenyl that is unsubstituted or substituted by one or more substituents selected from the group consisiting of:
-aryl;
—O—$C_{1-20}$ alkyl,
—O—($C_{1-20}$ alkyl)$_{0-1}$-aryl;
—$C_{1-20}$ alkoxycarbonyl;
—$S(O)_{0-2}$-$C_{1-20}$ alkyl;
—$S(O)_{0-2}$-($C_{1-20}$ alkyl)$_{0-1}$-aryl;
—$N(R_3)_2$;
—$NR_3$—CO—O—$C_{1-20}$ alkyl;
—$N_3$;
-oxo;
-halogen;
—$NO_2$;
—OH; and
—SH; or $R_4$ is

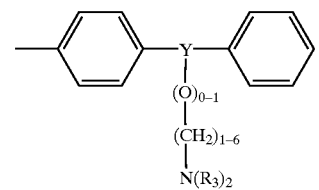

wherein Y is —N— or —CR—;
$R_2$ is selected from the group consisting of:
-hydrogen;
—$C_{1-10}$ alkyl;
—$C_{2-10}$ alkenyl;
-aryl;
—$C_{1-10}$ alkyl-O—$C_{1-10}$-alkyl;
—$C_{1-10}$ alkyl-O—$C_{2-10}$ alkenyl; and
—$C_{1-10}$ alkyl or $C_{2-10}$ alkenyl substituted by one or more substituents selected from the group consisting of:
—OH;
-halogen;
—$N(R_3)_2$;
—CO—$N(R_3)_2$;
—CO—$C_{1-10}$ alkyl;
—$N_3$;
-aryl; and
—CO-aryl;

each $R_3$ is independently selected from the group consisting of hydrogen and $C_{1-10}$ alkyl; and each R is independently selected from the group consisting of hydrogen, $C_{1-10}$ alkyl, $C_{1-10}$ alkoxy, halogen and trifluoromethyl, or a pharmaceutically acceptable salt thereof.

10. A compound according to claim 9 wherein $R_1$ is selected from the group consisting of $C_{1-6}$ alkyl and $C_{1-6}$ hydroxyalkyl.

11. A compound according to claim 10 wherein $R_1$ is selected from the group consisting of n-butyl, 2-hydroxy-2-methylpropyl, and 2-methylpropyl.

12. A compound according to claim 9 wherein $R_2$ is selected from the group consisting of methyl, n-butyl, benzyl, ethoxymethyl, and methoxyethyl.

13. A compound according to claim 9 wherein each R is hydrogen.

14. A pharmaceutical composition comprising a pharmaceutically effective amount of a compound according to claim 9 and a pharmaceutically acceptable carrier.

15. A method of inducing cytokine biosynthesis in an animal comprising administering an effective amount of a compound according to claim 9 to the animal.

16. A method of treating a viral infection in an animal comprising administering an effective amount of a compounds according to claim 9 to the animal.

* * * * *

UNITED STATES PATENT AND TRADEMARK OFFICE
CERTIFICATE OF CORRECTION

PATENT NO. : 6,514,985 B1
DATED : February 4, 2003
INVENTOR(S) : Gerster, John F.

It is certified that error appears in the above-identified patent and that said Letters Patent is hereby corrected as shown below:

Column 6,
Reaction Scheme I, delete and insert in place thereof

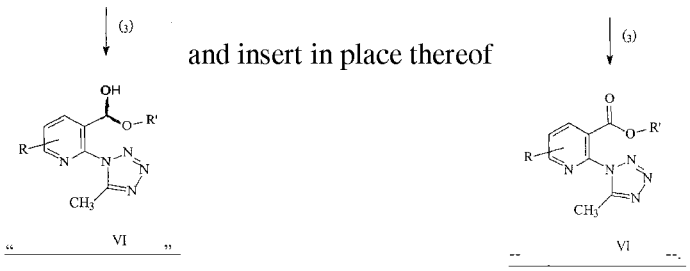

Column 23,
Line 66, delete "[(0.6 g, 1.8mmole)" and insert in place thereof -- [1,5-a]imidazo[4,5-c][1,8]naphthyridine (0.6 g, 1.8 mmole) --.

Column 24,
Line 56, delete "$C_{17}H_{27}N_530½H_2O$" and insert in place thereof -- $C_{17}H_{27}N_5+½H_2O$ --.
Line 57, delete "%H,.9.15;" and insert in place thereof -- %H, 9.15; --.

Column 26,
Line 30, delete "$N^3$" and insert in place thereof -- $N^5$ --.

Column 34,
Line 30, delete "rude" and insert in place thereof -- crude --.

Column 40,
Line 41, insert --.-- following "22.83".

Column 41,
Line 3, insert -- 8.5, -- following "J=".
Line 4, insert -- 2H), -- following "J=7.8 Hz,".
Line 7, insert -- 1.0-1.2 (m, 2 H), -- following "(m2H),".

Column 44,
Line 12, insert -- 7.9 Hz, -- following "apparent t, J=".
Line 15, delete "(m⁺)" and insert in place thereof -- (M⁺) --.

Column 48,
Line 20, delete "ethano" and insert in place thereof -- ethanol --.

Column 57,
Line 65, delete "$C_{15}H_{19}N^5O_4$" and insert in place thereof -- $C_{15}H_{19}N_5O_4$ --.

UNITED STATES PATENT AND TRADEMARK OFFICE
CERTIFICATE OF CORRECTION

PATENT NO.      : 6,514,985 B1
DATED           : February 4, 2003
INVENTOR(S)     : Gerster, John F.

It is certified that error appears in the above-identified patent and that said Letters Patent is hereby corrected as shown below:

Column 58,
Line 67, delete "pro" and insert in place thereof -- pro- --.

Column 59,
Line 48, insert --.-- following "384.2273".

Column 60,
Line 67, insert --.-- following "326.1846".

Column 61,
Line 34, insert --.-- following "352.1996".

Column 62,
Line 44, insert --.-- following "516.3226".

Column 63,
Line 67, insert --.-- following "396.1905".

Column 67,
Line 9, insert --.-- following "407.2068".

Column 69,
Line 27, delete [1,5-c]" and insert in place thereof -- [1,5] --.

Column 74,
Line 63, delete "6" and insert in place thereof -- =8.49 --.

Column 82,
Example 131, delete "J=6Hz," and insert in place thereof -- J≈6Hz, --.

Column 90,
Table Heading, delete "$^{1}$H" and insert in place thereof -- $\underline{1}$H --.

Column 94,
Example 164, delete "J=8Hz, 1 H)," and insert in place thereof -- J=8, 1 Hz, 1 H), --.

Column 111,
Line 60, insert --.-- following "396.2112".

UNITED STATES PATENT AND TRADEMARK OFFICE
CERTIFICATE OF CORRECTION

PATENT NO. : 6,514,985 B1
DATED : February 4, 2003
INVENTOR(S) : Gerster, John F.

It is certified that error appears in the above-identified patent and that said Letters Patent is hereby corrected as shown below:

Column 116,
Line 32, delete "Followin" and insert in place thereof -- Following --.
Line 64, delete "ct" and insert in place thereof -- $\alpha$ --.

Column 119,
Line 1, delete "$C_{1-10}$" and insert in place thereof -- $C_{2-10}$ --.
Lines 47-55, insert -- I -- under structure.

Signed and Sealed this

Seventeenth Day of August, 2004

JON W. DUDAS
*Acting Director of the United States Patent and Trademark Office*